US012611467B2

(12) United States Patent
Crystal et al.

(10) Patent No.: US 12,611,467 B2
(45) Date of Patent: Apr. 28, 2026

(54) APOE GENE THERAPY

(71) Applicant: Cornell University, Ithaca, NY (US)

(72) Inventors: Ronald G. Crystal, New York, NY (US); Stephen M. Kaminsky, Bronx, NY (US); Katie M Stiles, Bronx, NY (US); Dolan Sondhi, New York, NY (US)

(73) Assignee: Cornell University, Ithaca, NY (US)

( * ) Notice: Subject to any disclaimer, the term of this patent is extended or adjusted under 35 U.S.C. 154(b) by 828 days.

(21) Appl. No.: 17/779,812

(22) PCT Filed: Nov. 25, 2020

(86) PCT No.: PCT/US2020/070822

§ 371 (c)(1),
(2) Date: May 25, 2022

(87) PCT Pub. No.: WO2021/108809

PCT Pub. Date: Jun. 3, 2021

(65) Prior Publication Data

US 2023/0044351 A1      Feb. 9, 2023

Related U.S. Application Data

(60) Provisional application No. 62/939,999, filed on Nov. 25, 2019.

(51) Int. Cl.

| | |
|---|---|
| *A61K 48/00* | (2006.01) |
| *A61P 25/28* | (2006.01) |
| *C07K 14/775* | (2006.01) |
| *C12N 15/113* | (2010.01) |
| *C12N 15/86* | (2006.01) |

(52) U.S. Cl.
CPC ........ *A61K 48/005* (2013.01); *A61K 48/0075* (2013.01); *A61P 25/28* (2018.01); *C07K 14/775* (2013.01); *C12N 15/113* (2013.01); *C12N 15/86* (2013.01); *C12N 2310/141* (2013.01)

(58) Field of Classification Search
None
See application file for complete search history.

(56) References Cited

U.S. PATENT DOCUMENTS

| | | | |
|---|---|---|---|
| 4,861,719 A | 8/1989 | Miller |
| 5,278,056 A | 1/1994 | Bank et al. |
| 5,882,877 A | 3/1999 | Gregory et al. |
| 6,013,516 A | 1/2000 | Verma et al. |
| 7,687,616 B1 | 3/2010 | Bentwich et al. |
| 8,741,298 B2 | 6/2014 | Schenk et al. |
| 2002/0107213 A1 | 8/2002 | Verlinden et al. |
| 2007/0036761 A1 | 2/2007 | Bales et al. |
| 2016/0186171 A1 | 6/2016 | Naar et al. |
| 2017/0165377 A1 | 6/2017 | Gao et al. |

| | | | |
|---|---|---|---|
| 2019/0185544 A1 | 6/2019 | Sawmiller et al. |
| 2019/0231899 A1 | 8/2019 | Millette et al. |
| 2020/0024617 A1 | 1/2020 | Gao et al. |
| 2020/0046853 A1 | 2/2020 | Offen et al. |
| 2020/0181646 A1 | 6/2020 | Esteves et al. |
| 2020/0263199 A1 | 8/2020 | Sah et al. |
| 2022/0202932 A1 | 6/2022 | Micol et al. |
| 2023/0405148 A1 | 12/2023 | Crystal et al. |

FOREIGN PATENT DOCUMENTS

| | | |
|---|---|---|
| AU | 2020367437 B2 | 2/2025 |
| AU | 2020391518 B2 | 5/2025 |
| CN | 101652063 A | 2/2010 |
| CN | 106890315 A | 6/2017 |
| CN | 109776665 A | 5/2019 |
| CN | 110121356 A | 8/2019 |
| CN | 111471716 A | 7/2020 |
| CN | 114250235 A | 3/2022 |
| CN | 114761569 | 7/2022 |
| CN | 114829390 | 7/2022 |
| CN | 116574760 A | 8/2023 |
| EP | 0716591 A1 | 6/1996 |
| JP | 2009531299 A | 9/2009 |
| JP | 2023500793 A | 1/2023 |
| JP | 2023502515 | 1/2023 |
| JP | 2025163078 A | 10/2025 |
| MX | 2025012376 | 12/2025 |
| WO | WO-9419478 A1 | 9/1994 |
| WO | WO-9514785 A1 | 6/1995 |

(Continued)

OTHER PUBLICATIONS

Vitek, et al. (2020) "Translational animal models for Alzheimer's disease: An Alzheimer's Association Business Consortium Think Tank", Translational Research Clinical Interventions, e12114 (12 pages). (Year: 2020).*
"Australian Application Serial No. 2020367437, First Examination Report mailed Mar. 6, 2024", 4 pgs.
"Australian Application Serial No. 2020367437, Response filed Sep. 16, 2024 to First Examination Report mailed Mar. 6, 2024", 15 pgs.
"Australian Application Serial No. 2020391518, Response filed Nov. 29, 2024 to First Examination Report mailed Mar. 4, 2024", w/ claims, 14 pgs.

(Continued)

*Primary Examiner* — Robert M Kelly
(74) *Attorney, Agent, or Firm* — Schwegman Lundberg & Woessner, P.A.

(57) ABSTRACT

A gene therapy vector comprising an expression cassette coding for a mammalian apolipoprotein E that has a residue other than arginine at at least one of positions 112, 136, or 158, but is not a mammalian apolipoprotein E that has R112, R136 and R158 or a mammalian apolipoprotein E that has C112, R136 and C158, or coding for an antibody that binds to APOE4 or disrupts the binding of APOE to heparan sulfate proteoglycans, and methods of using the vector, are provided.

6 Claims, 24 Drawing Sheets

Specification includes a Sequence Listing.

(56)                References Cited

FOREIGN PATENT DOCUMENTS

| WO | WO-9622378 A1 | 7/1996 |
|----|----|----|
| WO | WO-9716458 A1 | 5/1997 |
| WO | WO-2005116204 A1 | 12/2005 |
| WO | 2013172964 | 11/2013 |
| WO | WO-2013181618 A2 | 12/2013 |
| WO | 2015077473 | 5/2015 |
| WO | 2018045347 | 3/2018 |
| WO | WO-2018226887 A1 | 12/2018 |
| WO | WO-2019028306 A2 | 2/2019 |
| WO | WO-2019217483 A1 | 11/2019 |
| WO | WO-2019222329 A1 | 11/2019 |
| WO | WO-2020077165 A1 | 4/2020 |
| WO | 2020112802 | 6/2020 |
| WO | WO-2020190768 A1 | 9/2020 |
| WO | WO-2020243346 A1 | 12/2020 |
| WO | 2021076941 | 4/2021 |
| WO | WO-2021108809 A1 | 6/2021 |
| WO | WO-2022115535 A1 | 6/2022 |
| WO | WO-2022233880 A1 | 11/2022 |
| WO | WO-2023198745 A1 | 10/2023 |
| WO | WO-2023201354 A2 | 10/2023 |
| WO | WO-2024011237 A1 | 1/2024 |
| WO | WO-2024220722 A1 | 10/2024 |
| WO | WO-2024220726 A1 | 10/2024 |
| WO | WO-2024220726 A9 | 8/2025 |
| WO | WO-2025213111 A2 | 10/2025 |
| WO | 2025213111 | 12/2025 |

OTHER PUBLICATIONS

"Australian Application Serial No. 2025200812, Voluntary Amendment filed Apr. 8, 2025", w/ claims, 11 pgs.

"Canadian Application Serial No. 3,157,864, Office Action mailed Nov. 25, 2022", 2 pgs.

"Canadian Application Serial No. 3,157,864, Response Filed Nov. 30, 2022 to Office Action mailed Nov. 25, 2022", 2 pgs.

"Canadian Application Serial No. 3,157,864, Voluntary Amendment filed Oct. 16, 2024", 10 pgs.

"Chinese Application Serial No. 202080073402.8, Office Action mailed Jan. 27, 2025", W/ English Claims, 8 pgs.

"Chinese Application Serial No. 202080073402.8, Office Action mailed Jun. 8, 2024", w/ English translation, 21 pgs.

"Chinese Application Serial No. 202080073402.8, Office Action mailed Jun. 16, 2025", W/English Translation, 17 pgs.

"Chinese Application Serial No. 202080073402.8, Response filed May 27, 2025 to Office Action mailed Jan. 27, 2025", w/ english claims, 25 pgs.

"Chinese Application Serial No. 202080073402.8, Response Filed Oct. 8, 2024 to Office Action mailed Jun. 8, 2024", W/ English Claims, 17 pgs.

"Chinese Application Serial No. 202080073402.8, Response Filed Jun. 14, 2022 to Notification to (Make Rectification mailed May 13, 2022", 5 pgs.

"Chinese Application Serial No. 202080081724.7, Decision of Rejection mailed Mar. 29, 2025", w/ English translation, 13 pgs.

"Chinese Application Serial No. 202080081724.7, Office Action mailed May 31, 2024", w/ English Translation, 16 pgs.

"Chinese Application Serial No. 202080081724.7, Request for Reexamination filed Jun. 7, 2025", W/English Claims, 11 pgs.

"Chinese Application Serial No. 202080081724.7, Response filed Dec. 2, 2024 to Office Action mailed May 31, 2024", w/ english claims, 13 pgs.

"European Application Serial No. 20804387.7, Communication Pursuant to Article 94(3) EPC mailed Nov. 6, 2023", 6 pgs.

"European Application Serial No. 20804387.7, Response filed May 23, 2024 to Communication Pursuant to Article 94(3) EPC mailed Nov. 6, 2023", 9 pgs.

"European Application Serial No. 3,162,761 Voluntary Amendment Filed Nov. 21, 2024", w/ claims, 9 pgs.

"International Application Serial No. PCT/US2024/025285, International Search Report mailed Sep. 10, 2024", 5 pgs.

"International Application Serial No. PCT/US2024/025285, Written Opinion mailed Sep. 10, 2024", 10 pgs.

"International Application Serial No. PCT/US2024/025290, International Search Report mailed Aug. 16, 2024", 5 pgs.

"International Application Serial No. PCT/US2024/025290, Written Opinion mailed Aug. 16, 2024", 5 pgs.

"Japanese Application Serial No. 2022-522814, Notification of Reasons for Refusal mailed Mar. 11, 2025", w/ English Translation, 6 pgs.

"Japanese Application Serial No. 2022-522814, Notification of Reasons for Refusal mailed Sep. 26, 2024", w/ English Translation, 13 pgs.

"Japanese Application Serial No. 2022-522814, Response filed Jun. 6, 2025 to Notification of Reasons for Refusal mailed Mar. 11, 2025", w/ english claims, 12 pgs.

"Japanese Application Serial No. 2022-522814, Response filed Dec. 25, 2024 to Notification of Reasons for Refusal mailed Sep. 26, 2024", w/ english claims, 11 pgs.

"Japanese Application Serial No. 2022-522814, Voluntary Amendment mailed Oct. 13, 2023", W/ English Claims, 13 pgs.

"Japanese Application Serial No. 2022-530164, Examiners Decision of Final Refusal mailed Mar. 27, 2025", W/ English Translation, 8 pgs.

"Japanese Application Serial No. 2022-530164, Notification of Reasons for Refusal mailed Sep. 26, 2024", w/ English Translation, 10 pgs.

"Japanese Application Serial No. 2022-530164, Response filed Feb. 5, 2025 to Notification of Reasons for Refusal mailed Sep. 26, 2024", w/ english claims, 11 pgs.

"Korean Application Serial No. 10-2022-7016247, Voluntary Amendment mailed Oct. 16, 2023", W/ English Claims, 2 pgs.

"Korean Application Serial No. 10-2022-7021579, Notice of Preliminary Rejection mailed Nov. 28, 2024", w/ English Claims, 5 pgs.

"Korean Application Serial No. 10-2022-7021579, Response filed Feb. 18, 2025 to Notice of Preliminary Rejection mailed Nov. 28, 2024", w/ english claims, 12 pgs.

"New Zealand Application Serial No. 789753, First Examination Report mailed Feb. 13, 2025", 2 pgs.

"Rare Luck: Two Copies of ApoE2 Shield Against Alzheimer's", Alzforum, 2019., (Aug. 8, 2019), 7 pgs.

"Singapore Application Serial No. 11202203722P, Written Opinion mailed Jun. 20, 2025", 8 pgs.

"Singaporean Application Serial No. 11202203722P, Voluntary Amendment Filed Oct. 14, 2022", W/ English Claims, 13 pgs.

"South African Application Serial No. 2022/05344, Voluntary Amendment Filed Dec. 19, 2022", 16 pgs.

"South African Application Serial No. 2022/07061, Voluntary Amendment filed May 30, 2024", W/ English Claims, 7 pgs.

Bandiera, Simonetta, et al., "miR-122—A key factor and therapeutic target in liver disease", Journal of Hepatology 2015 vol. 62 j 448-457, (Oct. 17, 2014), 10 pgs.

Bose, Abhishek, et al., "Comparison of Cardiac Specific Promoters to Liver-Specific miRNA Targets to Maximize Cardiac vs Liver Expression Following Intravenous AAVrh.10-Mediated Cardiac Gene Therapy", Molecular Therapy vol. 31 No. 4S1, Apr. 2023, p. 715, (May 16, 2023), 1 pg.

Casey, CS, et al., "Apolipoprotein E Inhibits Cerebrovascular Pericyte Mobility through a Rho A Protein-mediated Pathway", The Journal of Biological Chemistry, vol. 290, No. 22, (2015), 14208-14217.

Chang, Yi-Ming, et al., "Loss of hepatic miR-194 promotes liver regeneration and protects from acetaminophen-induced acute liver injury", Biochemical Pharmacology, vol. 195, Jan. 2022, 114862., Abstract Only, (Jan. 2022), 1 pg.

Cheng, Li, et al., "MicroRNA-148a deficiency promotes hepatic lipid metabolism and hepatocarcinogenesis in mice", Cell Death and Disease (2017) 8, e2916; doi:10.1038/cddis.2017.309; Jul. 13, 2017, (Jul. 13, 2017), 7 pgs.

(56)                    References Cited

OTHER PUBLICATIONS

Domenger, Claire, et al., "Next-generation AAV vectors—do not judge a virus (only) by its cover", Human Molecular Genetics, vol. 28, No. R1, (Oct. 1, 2019), R3-R14.

Geisler, A, et al., "microRNA122—regulated transgene expression increases specificity of cardiac gene transfer upon intravenous delivery of AAV9 vectors", Gene Therapy, vol. 18, No. 2, (Feb. 1, 2011), 199-209.

Geng, L., et al., "MicroRNA-192 Suppresses Liver Metastasis of Colon Cancer", Oncogene. Nov. 13, 2014; 33(46): 5332-5340. doi:10.1038/onc.2013.478., (Nov. 13, 2014), 22 pgs.

Günaydin, Caner, et al., "AAVrh. 10 delivery of novel APOe2—Christchurch variant suppresses amyloid and tau pathology in Alzheimer's disease mice", Molecular Therapy vol. 32 No. 12 Dec. 2024, The American Society of Gene and Cell Therapy, (2024), 4303-4318.

Hubacek, J. A, et al., "Rare Variant of Apolipoprotein E (Argl36->Ser) in Two Normolipidemic Individuals", Physiol. Res., vol. 54, (2005), 573-575.

Kraszewska, Izabela, et al., "Variability in Cardiac miRNA-122 Level Determines Therapeutic Potential of miRNA-Regulated AAV Vectors", Molecular Therapy—Methods & Clinical Development, vol. 17, (Jun. 1, 2020), 1190-1201.

Meng, Z., et al., "miR-194 Is a Marker of Hepatic Epithelial Cells and Suppresses Metastasis of Liver Cancer Cells in Mice", American Association for the Study of Liver Diseases, 2010., (Aug. 3, 2010), 10 pgs.

Wardell, R. Mark, et al., "Apolipoprotein E2—Christchurch (136 Arg -> Ser)", J Clin Invest, vol. 80, (1987), 483-490.

Yu-Wen, Alvin Huang, "ApoE2, ApoE3 and ApoE4 Differentially Stimulate APP Transcription and Aβ Secretion", Cell Press, vol. 168, (Jan. 26, 2017), 427-441.

Zhao, Lingzhi, et al., "Intracerebral adena-associated virus gene delivery of apolipoprotein E2 markedly reduces brain amyloid pathology in Alzheimer's disease mouse models", Neurobiology Of Aging. Tarrytown. NY. US. vol. 44 (Abstract Only), (Apr. 30, 2016), 8 pgs.

"International Application Serial No. PCT US2020 056051, International Search Report mailed Feb. 3, 2021", 6 pgs.

"International Application Serial No. PCT US2020 056051, Written Opinion mailed Feb. 3, 2021", 6 pgs.

"International Application Serial No. PCT US2020 056051, International Preliminary Report on Patentability mailed Apr. 28, 2022", 8 pgs.

"Mexican Application Serial No. MX a 2022 004524, Office Action mailed Apr. 28, 2022", w Machine English translation, 6 pgs.

"Chinese Application Serial No. 202080073402.8, Notification to Make Rectification mailed May 13, 2022", W English Translation, 5 pgs.

"International Application Serial No. PCT US2020 070822, International Preliminary Report on Patentability mailed Jun. 9, 2022", 8 pgs.

"Japanese Application Serial No. 2022-522814, Voluntary Amendment filed Jun. 28, 2022", 16 pgs.

"Canadian Application Serial No. 3,157,864, Office Action mailed Jul. 13, 2022", 2 pgs.

"Mexican Application Serial No. MX a 2022 004524, Response Filed Jun. 30, 2022 to Office Action mailed Apr. 28, 2022", 66 pgs.

"Mexican Application Serial No. MX a 2022 004524, Voluntary Amendment mailed Jul. 7, 2022", W English Claims, 21 pgs.

"Japanese Application Serial No. 2022-530164, Voluntary Amendment Filed Jul. 26, 2022", W English Claims, 26 pgs.

"Canadian Application Serial No. 3,157,864, Response Filed Aug. 25, 2022 to Office Action mailed Jul. 13, 2022", 16 pgs.

"Israel Application Serial No. 292148, Notification Prior to Examination mailed Sep. 28, 2022", w Machine English translation, 4 pgs.

"South African Application Serial No. 2022 07061, Voluntary Amendment Filed Nov. 17, 2022", 11 pgs.

"Chinese Application Serial No. 202080081724.7, Voluntary Amendment Filed Dec. 21, 2022", W English Claims, 11 pgs.

"Israel Application Serial No. 293116, Notification Prior to Examination mailed Dec. 27, 2022", 7 pgs.

"European Application Serial No. 20828741.7, Response Filed Jan. 13, 2023 to Communication Pursuant to Rules 161(1) and 162 EPC mailed Jul. 7, 2022", 10 pgs.

"South African Application Serial No. 202207061, Voluntary Amendment Filed May 25, 2023", W English Claims, 10 pgs.

"Japanese Application Serial No. 2022-530164, Voluntary Amendment Filed Nov. 17, 2023", W English Claims, 15 pgs.

"Brazilian Application Serial No. BR112022010065-5, Voluntary Amendment Filed Nov. 23, 2023", W English Claims, 6 pgs.

"Mexican Application Serial No. MX a 2022 006364, Voluntary Amendment Filed Jan. 30, 2024", w English Claims.

"Australian Application Serial No. 2020391518, First Examination Report mailed Mar. 4, 2024", 4 pgs.

"New Zealand Application Serial No. 789753, Voluntary Amendment Filed Feb. 22, 2024", 137 pgs.

Chernick, Dustin, "Peripheral versus central nervous system APOE in Alzheimer's", Neuroscience Letters, Elsevier, Amsterdam, NL, vol. 708, (Jun. 7, 2019).

Daniel, Fowler K, "Improved knockdown from artificial microRNAs in an enhanced miR-155 backbone: a designer's guide to potent multi-target RNAi", Nucleic Acids Research, vol. 44 No. 5, (Nov. 17, 2015), e48-e48.

Hudry, E, "Gene Transfer of Human Apoe Isoforms Results in Differential Modulation of Amyloid Deposition and Neurotoxicity in Mouse Brain", Science Translational Medicine, vol. 5, No. 212, (Nov. 20, 2013), 212ral61-212ral61.

Ladu, Mary Jo, "Association of Human, Rat and Rabbit Apolipoprotein E with beta amyloid", J. Neurosci Res., 49(1), (1997), 10 pgs.

Long, Wu, "Human ApoE Isoforms Differentially Modulate Brain Glucose and Ketone Body Metabolism: Implications for Alzheimer's Disease Risk Reduction and Early Intervention", The Journal Of Neuroscience, vol. 38, No. 30, (Jul. 2, 2018), 6665-6681.

Mirna, Safieh, "ApoE4: an emerging therapeutic target for Alzheimer's disease", BMC Medicine, vol. 17, No. 1, (Mar. 20, 2019).

Munoz, Sonia Sanz, "Understanding the Role of ApoE Fragments in Alzheimer's Disease", Neurochemical Research, Plenum Press, New York, US, vol. 44, No. 6, (Sep. 17, 2018), 1297-1305.

Zhao, Lingzhi, "Intracerebral adeno-associated virus gene delivery of apolipoprotein E2 markedly reduces brain amyloid pathology in Alzheimer's disease mouse models", Neurobiology Of Aging, Tarrytown, NY, US, vol. 44, (Apr. 30, 2016), 159-172.

"International Application Serial No. PCT/US2020/070822, International Search Report mailed Mar. 30, 2021", 4 pgs.

"International Application Serial No. PCT/US2020/070822, Written Opinion mailed Mar. 30, 2021", 6 pgs.

Arboleda-Velasquez, Joseph F., et al., "Resistance to autosomal dominant Alzheimer's disease in an APOE3 Christchurch homozygote: a case report", Nature Medicine, 25, (2019), 15 pgs.

Ladu, Mary Jo, et al., "Association of Human, Rat and Rabbit Apolipoprotein E with beta amyloid", J. Neurosci Res., 49(1), (1997), 9-18.

Lanfranco, Marie Fe, et al., "ApoE Lipidation as a Therapeutic Target in Alzheimer's Disease", Int. J. Mol. Sci., 21(17), (2020), 19 pgs.

Reiman, Eric M., et al., "Exceptionally Low Likelihood of Alzheimer's Dementia in Apoe2 Homozygotes", medRxiv preprint first posted online Nov. 2, 2019 ; doi: http://dx.doi.org/10.1101/19011015 ., The copyright holder for this preprint (which was not peer-reviewed) is the author/funder, who has granted medRxiv a license to display the preprint in perpetuity. It is made available under a CC-BY-NC-ND 4.0 International license., (2019), 1-26.

Tagalakis, Aristides D., et al., "Gene Correction of the Apolipoprotein (Apo) E2 Phenotype to Wild-type ApoE3 by in Situ Chimeraplasty", Journal of Biological Chemistry, 276(16), (2000), 13226-13230.

"ApoE4—an emerging therapeutic target for Alzheimer's disease", BMC Medicine, vol. 17, No. 1, 2019., (Mar. 20, 2019), 18 pgs.

"U.S. Appl. No. 17/769,255, Restriction Requirement mailed Oct. 1, 2025", 10 pgs.

"Chinese Application Serial No. 202080073402.8, Decision of Rejection mailed Nov. 1, 2025", w/o English Translation, 6 pgs.

(56)                References Cited

OTHER PUBLICATIONS

"Chinese Application Serial No. 202080073402.8, Response filed Oct. 16, 2025 to Office Action mailed Jun. 16, 2025", w/ english claims, 15.

"Colombian Application Serial No. NC2022/0006367, Office Action mailed Aug. 27, 2025", w/ Machine English Translation, 32 pgs.

"European Application Serial No. 20804387.7, Communication Pursuant to Article 94(3) EPC mailed Aug. 28, 2025", 6 pgs.

"International Application Serial No. PCT/US2024/025285, International Preliminary Report on Patentability mailed Oct. 30, 2025", 12 pgs.

"International Application Serial No. PCT/US2024/025290, International Preliminary Report on Patentability mailed Oct. 30, 2025", 7 pgs.

"International Application Serial No. PCT/US2025/023280, International Search Report mailed Nov. 5, 2025", 7 pgs.

"International Application Serial No. PCT/US2025/023280, Invitation to Pay Additional Fees mailed Sep. 15, 2025", 6 pgs.

"International Application Serial No. PCT/US2025/023280, Written Opinion mailed Nov. 5, 2025", 12 pgs.

"Japanese Application Serial No. 2022-522814, Examiners Decision of Final Refusal mailed Aug. 7, 2025", W/English Translation, 6 pgs.

"Japanese Application Serial No. 2022-530164, Response filed Sep. 17, 2025 Examiners Decision of Final Refusal mailed Mar. 27, 2025", w/ claims, 10 pgs.

"Korean Application Serial No. 10-2022-7016247, Notice of Preliminary Rejection mailed Oct. 17, 2025", w/ English Translation, 6 pgs.

"Korean Application Serial No. 10-2022-7021579, Notice of Preliminary Rejection mailed Sep. 1, 2025", w/ English Translation, 6 pgs.

"Mexican Application Serial No. MX/a/2025/012376, Office Action mailed Oct. 22, 2025", W/O English Translation, 4 pgs.

"New Sealand Application Serial No. 788166, Voluntary Amendment filed Oct. 15, 2025", w/ claims, 4 pgs.

"New Zealand Application Serial No. 789753, Response filed Jul. 30, 2025 to First Examination Report mailed Feb. 13, 2025", w/ claims, 4 pgs.

"New Zealand Application Serial No. 789753, Subsequent Examiners Report mailed Aug. 4, 2025", 2 pgs.

"Singapore Application Serial No. 11202205460Y, Search Report and Written Opinion mailed Jun. 27, 2025", 9 pgs.

Ferguson, Chantal M, et al., "A combinatorial approach for achieving CNS-selective RNAi", Nucleic Acids Research, vol. 52, No. 9, pp. 5273-5284, [Online]. Retrieved from the Internet: <https://academic.oup.com/nar/article-pdf/52/9/5273/57807952/gkael00.pdf>, (Feb. 13, 2024), 12 pgs.

Ferguson, Chantal M, et al., "Silencing Apoe with divalent-siRNAs improves amyloid burden and activates immune response pathways in Alzheimer's disease", Alzheimer's and Dementia, vol. 20, No. 4, pp. 2632-2652, (Feb. 20, 2024), 21 pgs.

Karan, Kalpita R., et al., "Suppression of CNS APOE4 Expression by miRNAs Delivered by the S2 AAVrh. 10 Capsid-Modified AAV Vector", Human Gene Therapy, vol. 35, Nos. 21 and 22, (2024), 13 pgs.

Pencheva, Nora, et al., "Convergent multi-miRNA targeting of ApoE drives LRP1/LRP8-dependent melanoma metastasis and angiogenesis", Cell, vol. 151, No. 5, pp. 1068-1082, (Nov. 8, 2012), 15 pgs.

"U.S. Appl. No. 17/769,255, Response filed Dec. 1, 2025 to Restriction Requirement mailed Oct. 1, 2025", 6 pgs.

"Mexican Application Serial No. MX a 2025 012376, Response filed Nov. 18, 2025 to Office Action mailed Oct. 22, 2025", w o english claims, 4 pgs.

* cited by examiner

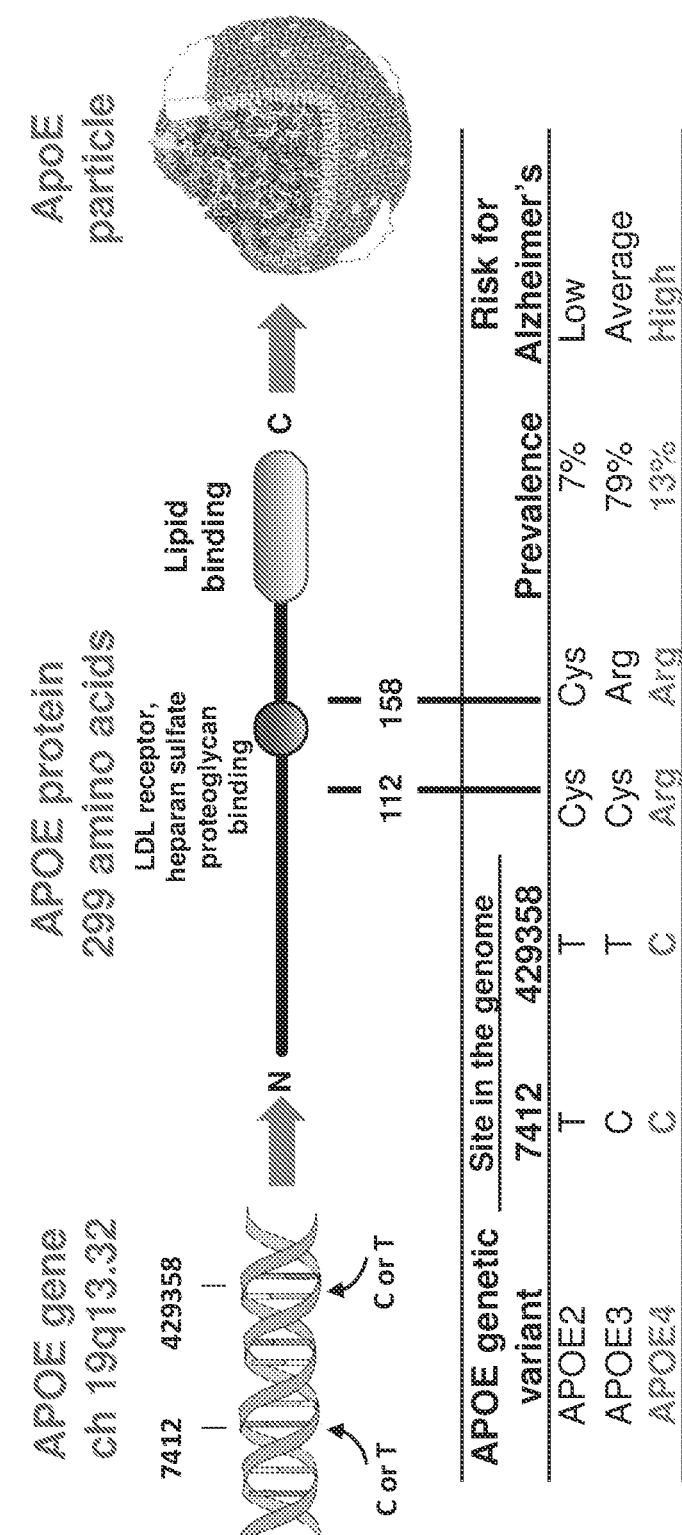
Figure 1. APOE4 Gene, Protein and Risk for Alzheimer's Disease

Figure 2. APOE2 Gene Therapy to Convert the APOE4 Brain to APOE2E4

Adeno-associated virus (AAV) gene therapy vector coding for the human APOE2 gene Brain

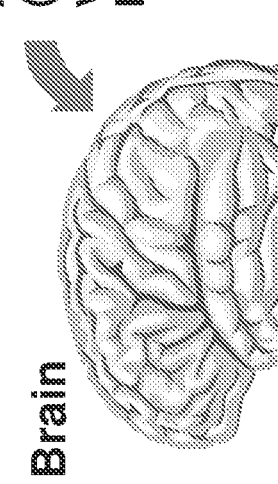

APOE4 homozygote
*High risk for Alzheimer's*

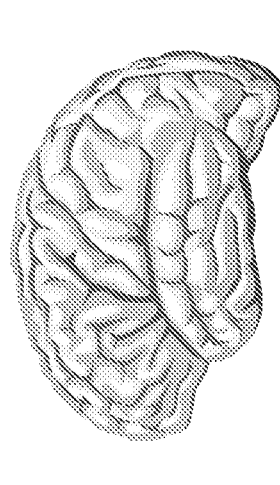

APOE2-APOE4 heterozygote
*Reduced risk for Alzheimer's*

• Adeno-associated virus delivery of the APOE2 gene to the CNS will genetically convert the E4 brain into an E2/E4 brain, thus reducing or preventing the pathology of Alzheimer's disease in APOE4 homozygotes Figure 3. AAVrh.10APOE2 Is Administered by the Intracisternal Route Directly to Brain Cerebral Spinal Fluid
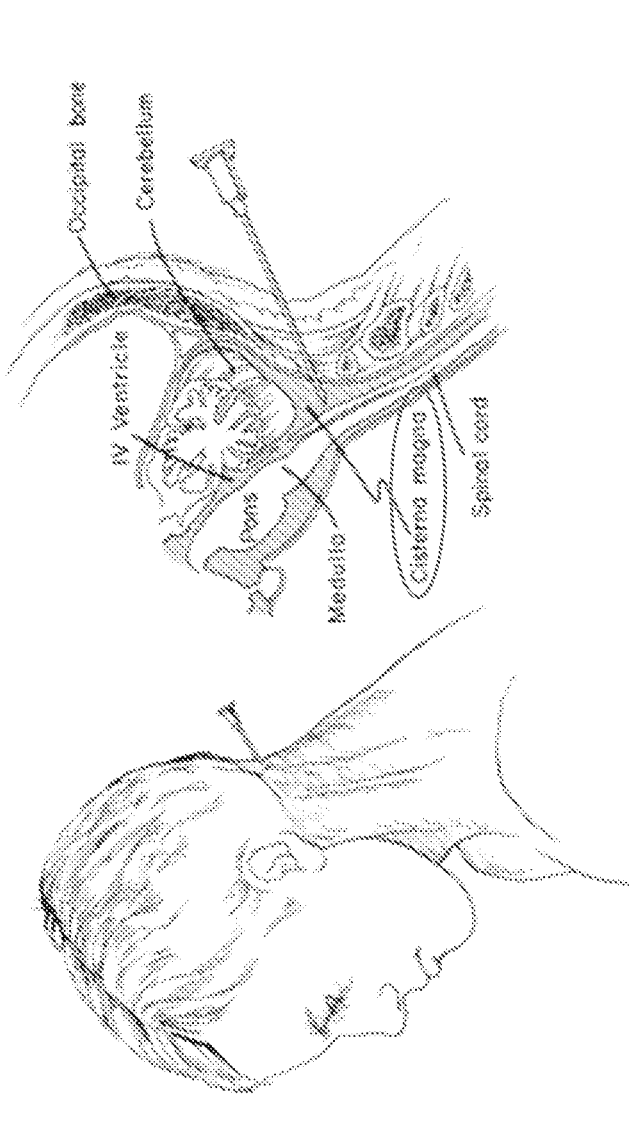
• Administration to the cisterna magna is an outpatient procedure

Figure 4. APOE3 ChristChurch Alzheimer's Disease-Protective APOE mutation

| APOE genetic variant | Amino acid 112 | 136 | 158 | Prevalence | Risk for Alzheimer's |
|---|---|---|---|---|---|
| APOE2 | Cys | Arg | Cys | 7% | Low |
| APOE3 | Cys | Arg | Arg | 79% | Average |
| APOE3Chc | Cys | Ser | Arg | Very low | Low |
| APOE4 | Arg | Arg | Arg | 13% | High |

Arboleda-Velasquez et al 2019 Resistance to autosomal dominant Alzheimer's disease in an APOE3 Christchurch homozygote: a case report. Nature Medicine
Zaiocusky et al 2019 An Alzheimer's-disease-protective APOE mutation, Nature Medicine
Reiman et al 2019 Exceptionally low likelihood of Alzheimer's dementia in APOE2 homozygotes. medRxiv Figure 5. APOE3ChristChurch Gene and Protein

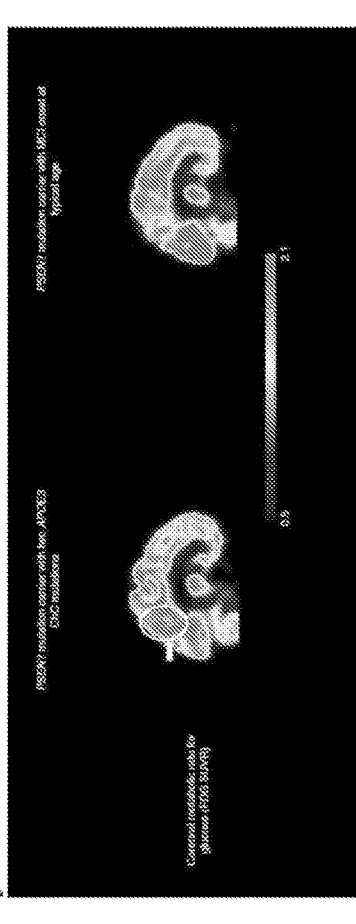
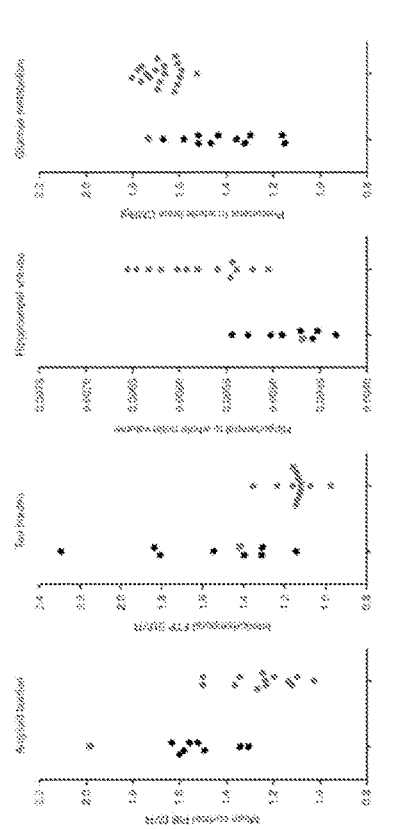

Figure 6. APOE3ch Mutation

* Case of Colombian woman with the autosomal-dominant _E280A_ mutation in presenilin 1 (Paisa mutation)

* Cognitively well for decades (age 70) past this mutation's typical age of disease onset (40 yr)

* This mutation causes Aβ overproduction, associated with neurodegeneration and cognitive decline

* At age 70 she has short-term memory but remains independent

* Amyloid PET scanning revealed a massive buildup of amyloid plaques in her brain, far higher than those seen in young mutation carriers who are cognitively impaired

* Very little tau pathology, mostly confined to the medial temporal lobe, brain glucose metabolism is almost normal

* It's as if the chain of pathogenic events is broken after amyloid formation

* Independent of the mechanism, can this mutation be used to treat APOE4 homozygotes?

Figure 7:
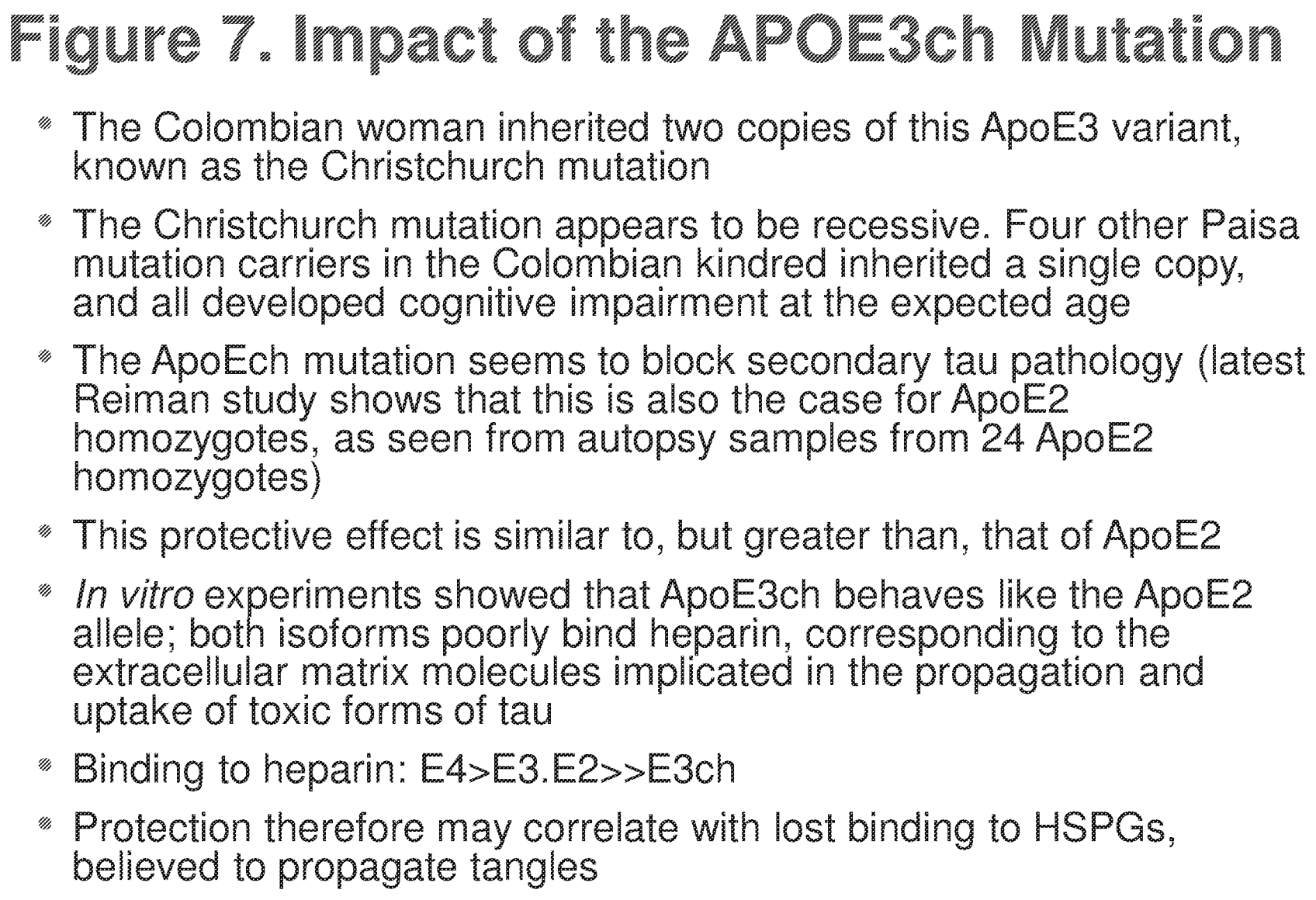

Figure 7. Impact of the APOE3ch Mutation

* The Colombian woman inherited two copies of this ApoE3 variant, known as the Christchurch mutation

* The Christchurch mutation appears to be recessive. Four other Paisa mutation carriers in the Colombian kindred inherited a single copy, and all developed cognitive impairment at the expected age

* The ApoEch mutation seems to block secondary tau pathology (latest Reiman study shows that this is also the case for ApoE2 homozygotes, as seen from autopsy samples from 24 ApoE2 homozygotes)

* This protective effect is similar to, but greater than, that of ApoE2

* *In vitro* experiments showed that ApoE3ch behaves like the ApoE2 allele; both isoforms poorly bind heparin, corresponding to the extracellular matrix molecules implicated in the propagation and uptake of toxic forms of tau

* Binding to heparin: E4>E3.E2>>E3ch

* Protection therefore may correlate with lost binding to HSPGs, believed to propagate tangles

Figure 8. Low Affinity of APOE3ch Binding to Heparin

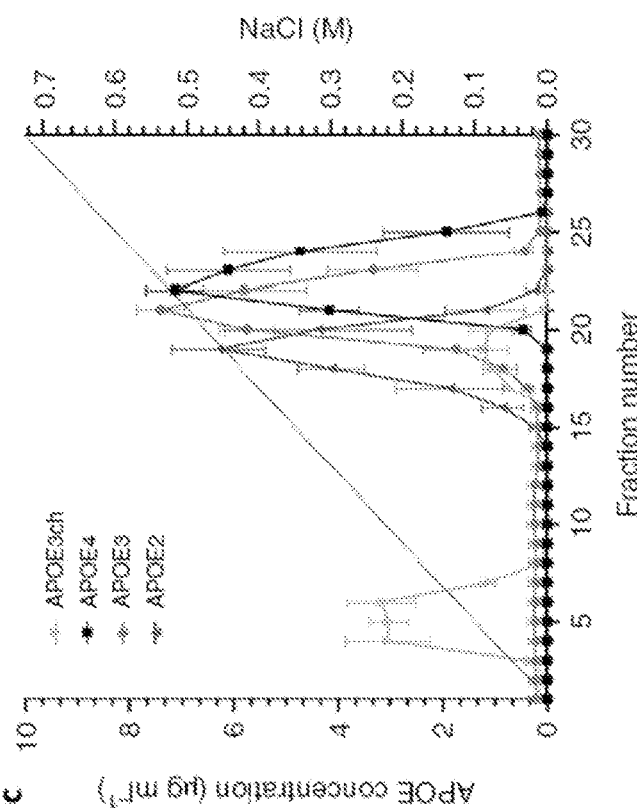

- HSPGs have been implicated in the buildup of amyloid plaques, as well as in promoting the microglial response to amyloid

- HSPGs have also been linked to tau pathology and suggested that these sticky receptors allow tau fibrils to get attached to neurons, facilitating uptake and propagation

- ApoE3 bound with an Ab to the aa 130–143 (which includes the region of the Christchurch mutation) converts ApoE3 to ApoEch as measured by heparin binding ApoE3ch was eluted from the heparin column with the lowest NaCl concentration, revealing impaired heparin binding compared to other ApoE isoforms.

Figure 9

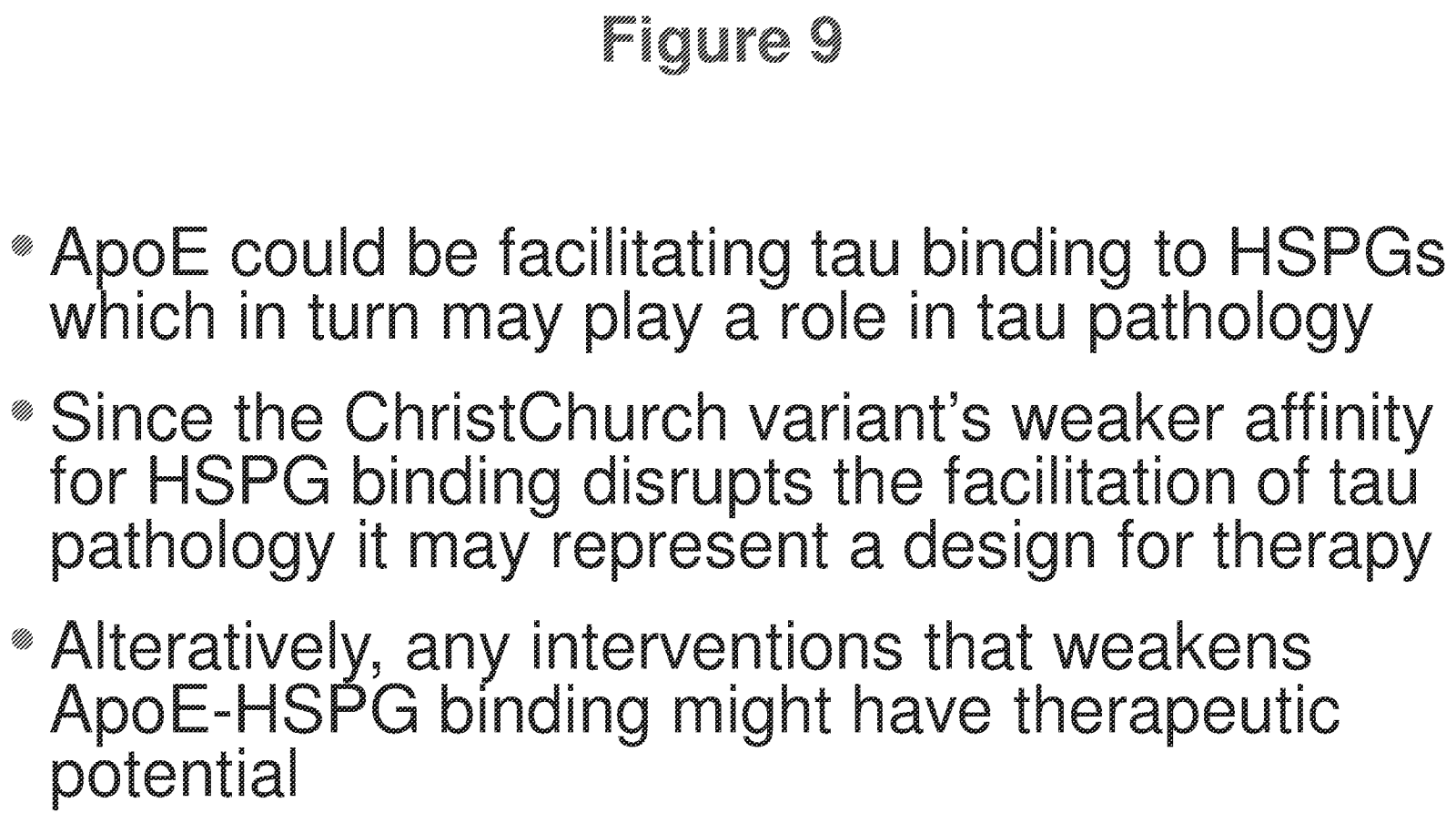

- ApoE could be facilitating tau binding to HSPGs which in turn may play a role in tau pathology

- Since the ChristChurch variant's weaker affinity for HSPG binding disrupts the facilitation of tau pathology it may represent a design for therapy

- Alteratively, any interventions that weakens ApoE-HSPG binding might have therapeutic potential

Figure 10

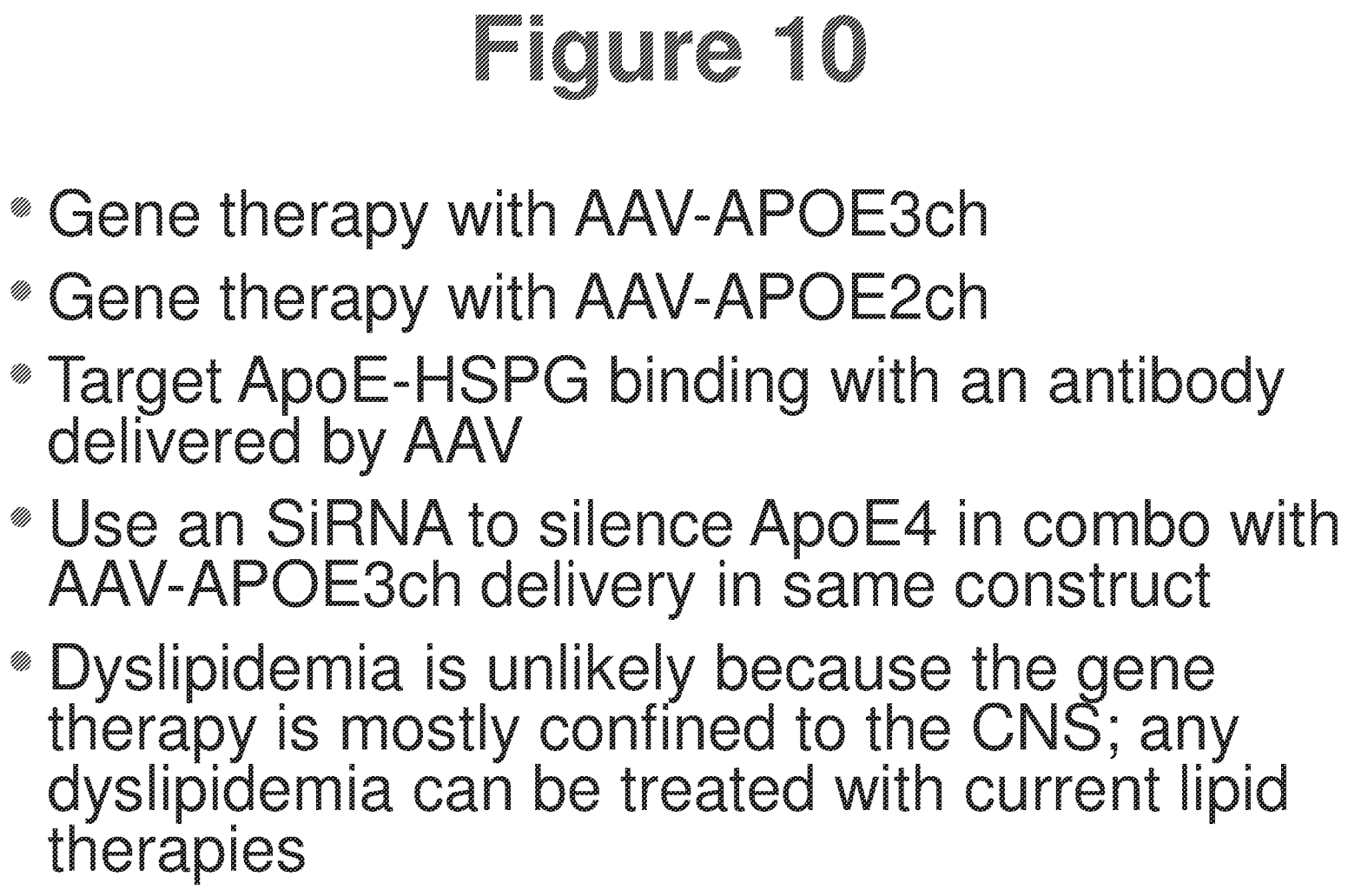

- Gene therapy with AAV-APOE3ch

- Gene therapy with AAV-APOE2ch

- Target ApoE-HSPG binding with an antibody delivered by AAV

- Use an SiRNA to silence ApoE4 in combo with AAV-APOE3ch delivery in same construct

- Dyslipidemia is unlikely because the gene therapy is mostly confined to the CNS; any dyslipidemia can be treated with current lipid therapies Figure 11. ApoE Protein Mutations that Result in Lipid Disorders May Alter Alzheimer's Predilection AAVrh.10hAPOE2 vector AAVrh.10hAPOE2

A. Human ApoE2 protein in brain sections
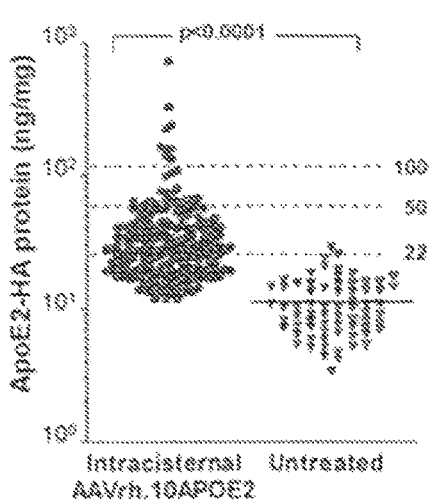
B. Human hAPOE2 protein in cerebral spinal fluid
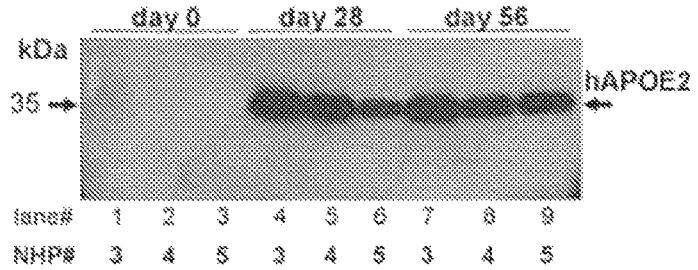
Figure 18
A. Aβ1-42
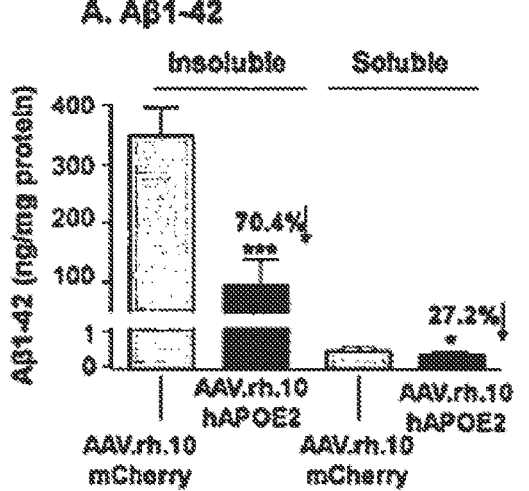
B. Aβ1-40
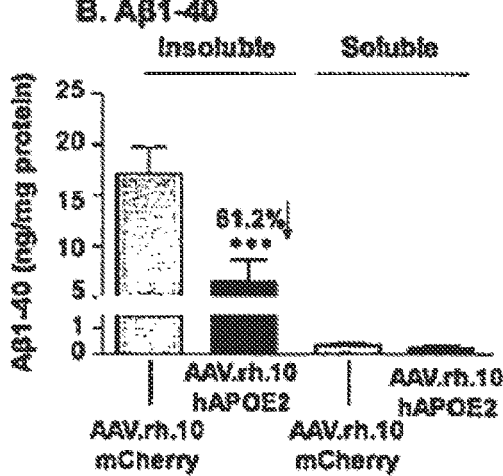
Figure 19

Figure 24. 293T Transfection

Transfection Scheme

- Co-transfect pAAVcag-miRAPOE4 with pmirGLO containing target sites or the vector alone

- Target 1
  - miRNA in the intron
  - miRNA in the polyA
  - New controls
- Null vector
  - miRNA in the intron
  - miRNA in the polyA
  - New controls

- This experiment tests the knockdown efficiency of miRs located in the intron and polyA

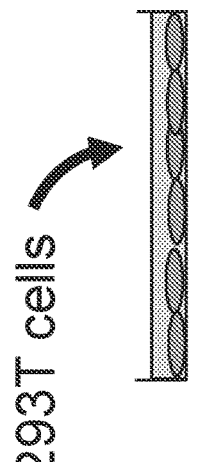
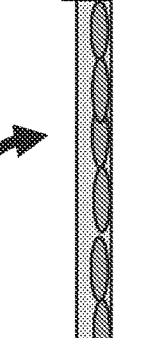
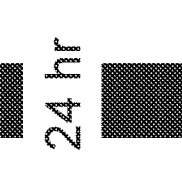
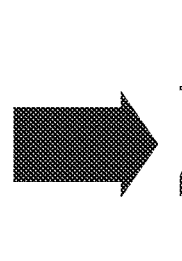

HEK293T cells 24 hr

Co-transfect for 24 or 72 hr

Read

Figure 25. Luciferase Results
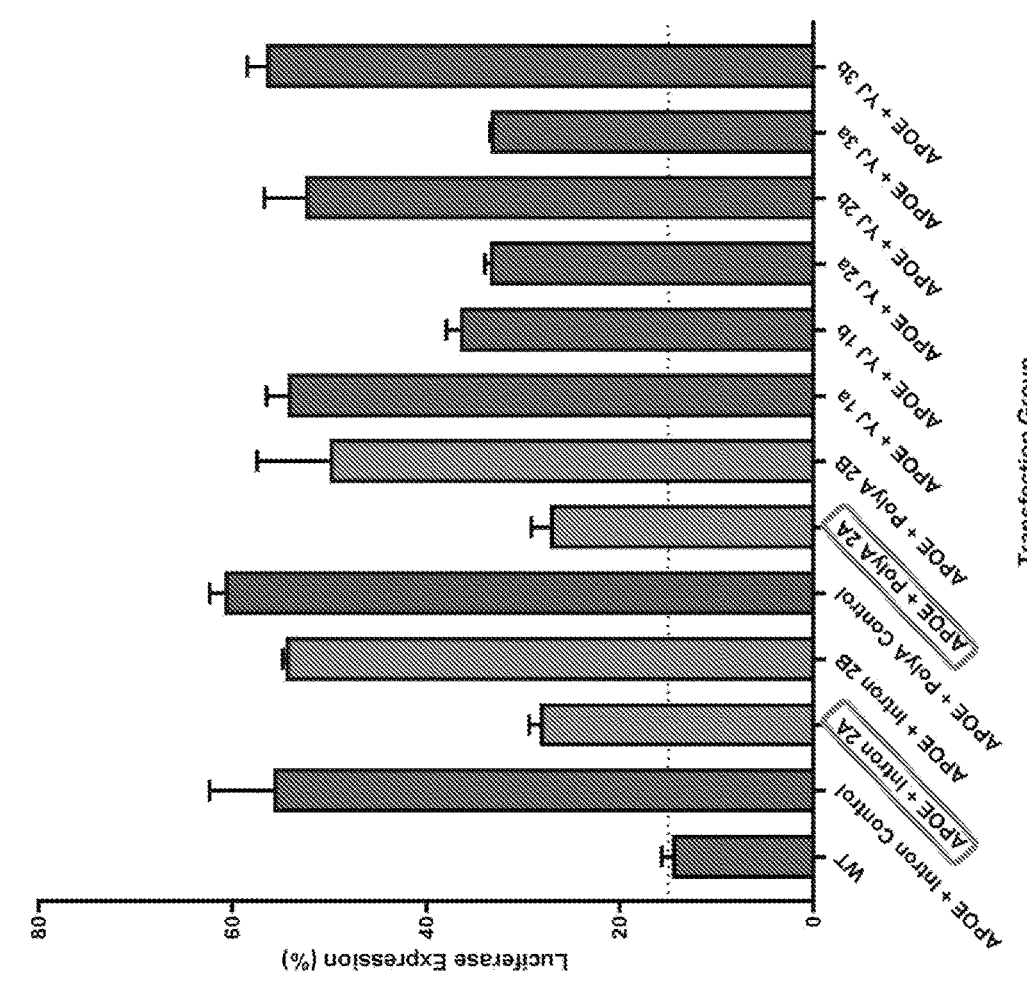
Conclusions
- miR2A in the intron or polyA appears to exhibit greater knockdown as compared to miR2B
Comments on Controls
- The empty vector controls were removed since the target site may decrease luciferase expression
- Another assay was set up to test luciferase expression with the pmirGLO containing target site, alone.

Figure 26. Testing APOE Target Site Only Control

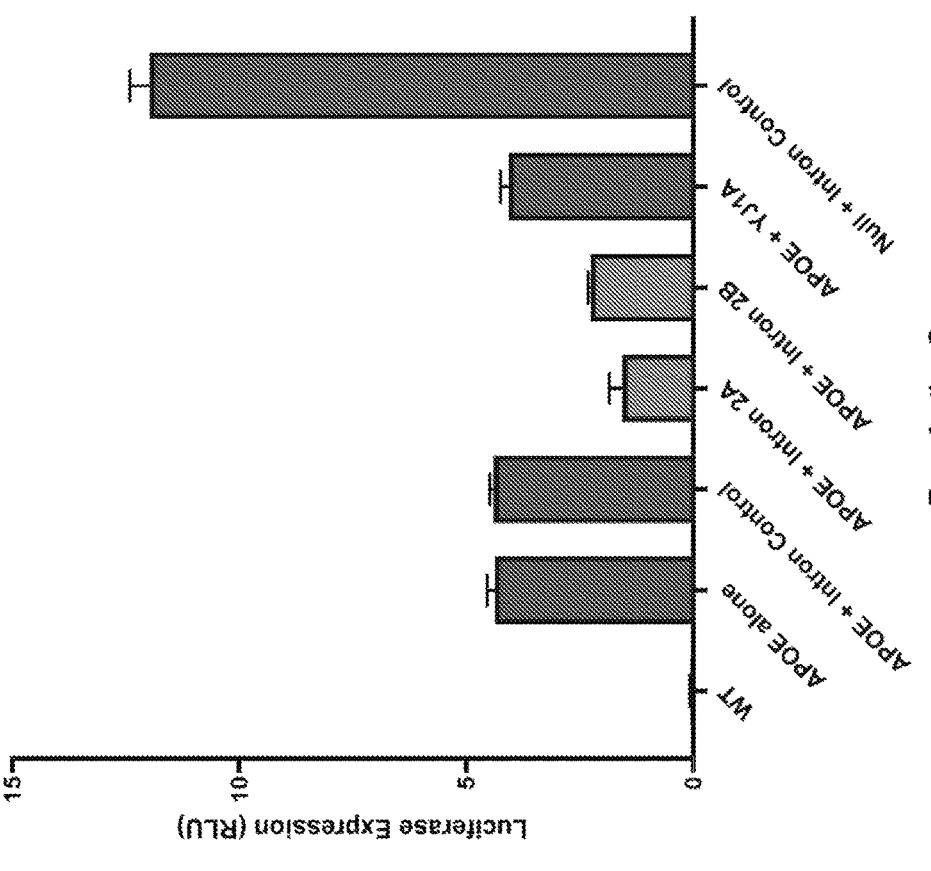

Rationale

- If the control pmirGLO containing target site alone decreases luciferase expression, then pmirGLOluc (null) vector cannot be used as a negative control.

- The target site may affect the stability of the mRNA, may contain cryptic binding site or may interact with translation machinery.

Conclusions

- miR2A in the intron or polyA appears to exhibit greater knockdown as compared to miR2B

Figure 27:
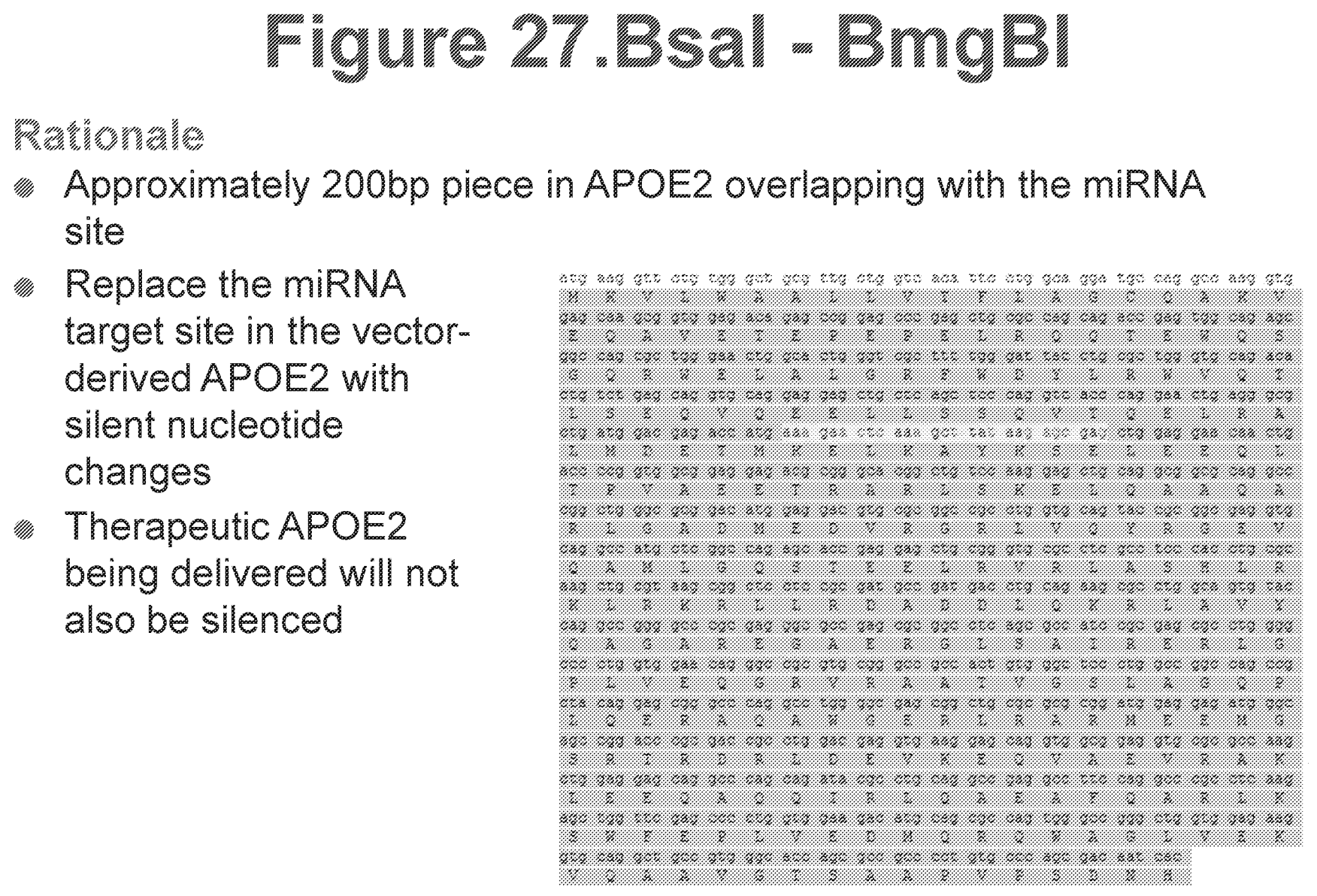

Figure 27.BsaI - BmgBI

Rationale

• Approximately 200bp piece in APOE2 overlapping with the miRNA site

• Replace the miRNA target site in the vector-derived APOE2 with silent nucleotide changes

• Therapeutic APOE2 being delivered will not also be silenced

Figure 28. Insertion of hApoE2-HA
*Strategy for Generating pAAV-miRNA-APOE-HA*
- Clone APOE2 into the pAAV with miRAPOE4
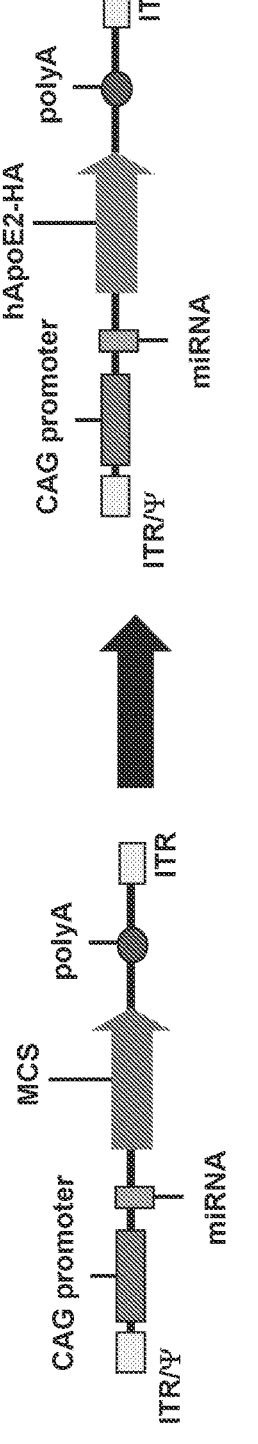
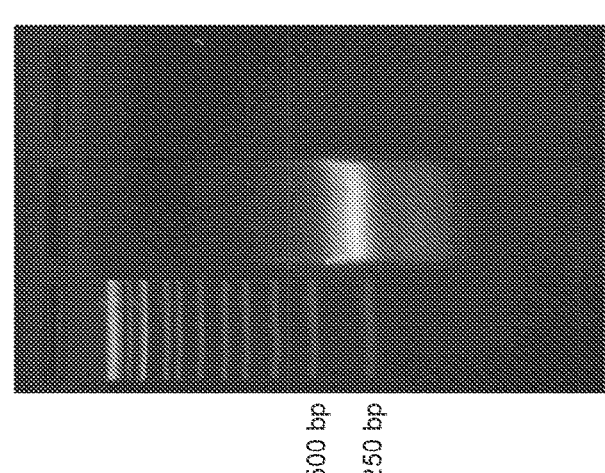
- BsaI-BmgBI fragment successfully PCR amplified (~250 bp)
- BsaI-BmgBI is cloned into the pAAV-miRNA with the strongest knockdown

Figure 29. *In Vivo Studies*

- Breeding P301S (Jax) mice with TRE4 mice
- AAV9 preparation with confirmed miRs Table I. Mouse Proof of Principle Study

| Mouse model (genotype)[2] | Vector | Administration dose and route | Parameters to be evaluated |
|---|---|---|---|
| P301S/E4 | AAV9-hAPOE2 | $10^{11}$ gc, via intracisternal (IC) route | • Behavior and neurologic assessment (monthly)<br>• Brain expression of hAPOE4 and hAPOE2<br>• Soluble and insoluble Aβ levels<br>• Assessment of phosphorylated tau and total tau levels in brain homogenates<br>• CNS assessment of neurofibrillary tangles<br>• Microglial activation<br>• Pathology of hippocampus and cortex |
|  | AAV9-hAPOE2-mirAPOE4 |  |  |
|  | AAV9-mCherry-mirAPOE4 |  |  |
|  | AAV9-null |  |  |
|  | No therapy (PBS) | None (PBS, IC) |  |
| C57Bl/6 (controls) | No therapy (PBS) | None (PBS, IC) |  |
| 2 strains | 5 vectors | 1 route | Necropsy @ 3 and 9 months of age |

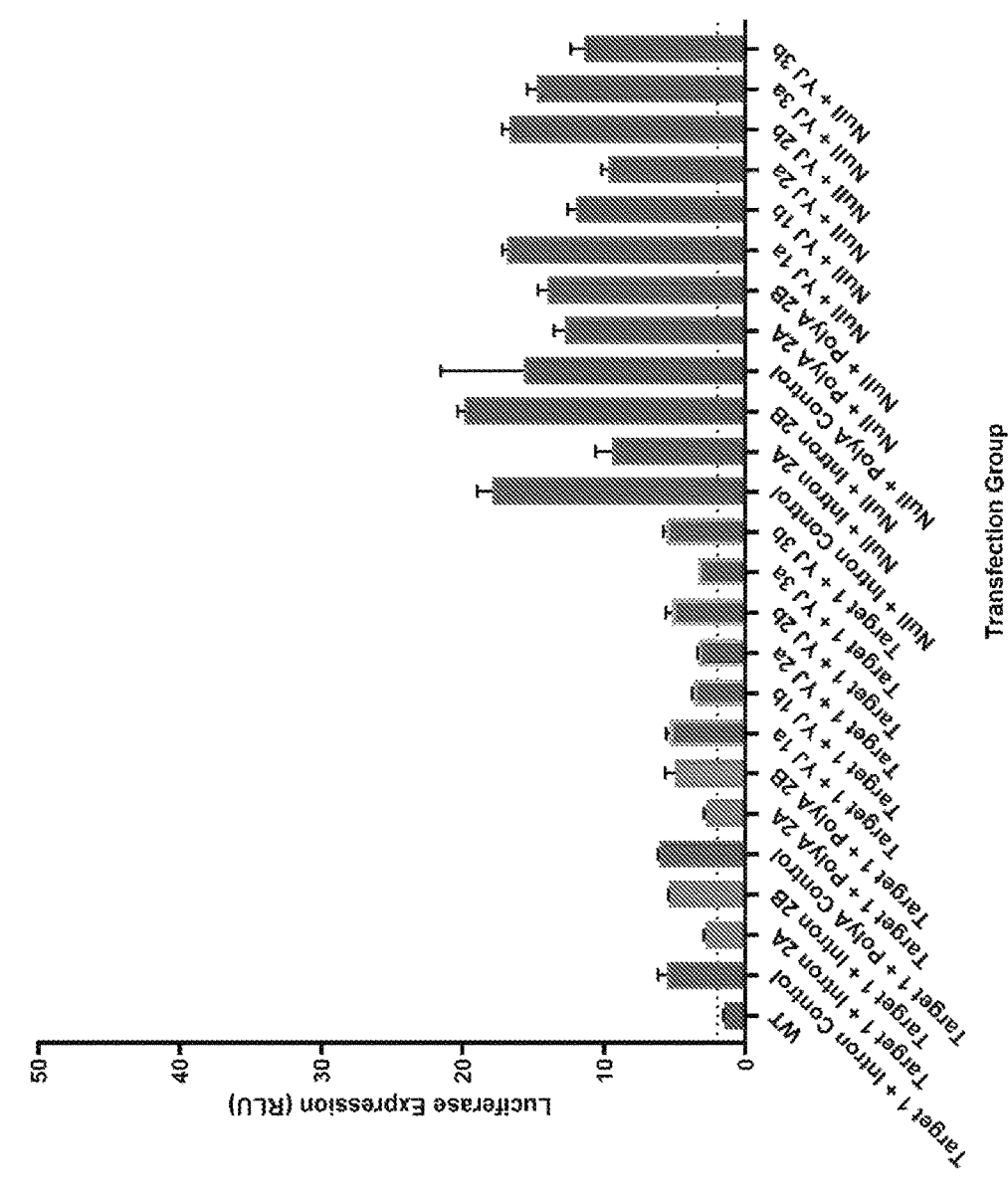
Figure 30. All Controls

SEQUENCE LISTING

<160> NUMBER OF SEQ ID NOS: 34

<210> SEQ ID NO 1
<211> LENGTH: 317
<212> TYPE: PRT
<213> ORGANISM: Homo sapiens

<400> SEQUENCE: 1

Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
            20                  25                  30

Arg Gln Gln Thr Glu Trp Gln Ser Gly Gln Arg Trp Glu Leu Ala Leu
        35                  40                  45

Gly Arg Phe Trp Asp Tyr Leu Arg Trp Val Gln Thr Leu Ser Glu Gln
    50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
                100                 105                 110

Lys Glu Leu Gln Ala Ala Gln Ala Arg Leu Gly Ala Asp Met Glu Asp
            115                 120                 125

Val Cys Gly Arg Leu Val Gln Tyr Arg Gly Glu Val Gln Ala Met Leu
    130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Asp Leu Gln Lys Arg
                165                 170                 175

Leu Ala Val Tyr Gln Ala Gly Ala Arg Glu Gly Ala Glu Arg Gly Leu
                180                 185                 190

Ser Ala Ile Arg Glu Arg Leu Gly Pro Leu Val Glu Gln Gly Arg Val
            195                 200                 205

Arg Ala Ala Thr Val Gly Ser Leu Ala Gly Gln Pro Leu Gln Glu Arg
    210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
                245                 250                 255

Val Arg Ala Lys Leu Glu Glu Gln Ala Gln Gln Ile Arg Leu Gln Ala
            260                 265                 270

Glu Ala Phe Gln Ala Arg Leu Lys Ser Trp Phe Glu Pro Leu Val Glu
            275                 280                 285

Asp Met Gln Arg Gln Trp Ala Gly Leu Val Glu Lys Val Gln Ala Ala
    290                 295                 300

Val Gly Thr Ser Ala Ala Pro Val Pro Ser Asp Asn His
305                 310                 315

<210> SEQ ID NO 2
<211> LENGTH: 1098
<212> TYPE: DNA
<213> ORGANISM: Homo sapiens

<400> SEQUENCE: 2
ggaacttgat gctcagagag gacaagtcat ttgcccaagg tcacacagct ggcaactggc      60

```
agagccagga ttcacgccct ggcaatttga ctccagaatc ctaaccttaa cccagaagca        120
cggcttcaag cccctggaaa ccacaatacc tgtggcagcc agggggaggt gctggaatct        180
catttcacat gtggggaggg ggctcccctg tgctcaaggt cacaaccaaa gaggaagctg        240
tgattaaaac ccaggtccca tttgcaaagc ctcgactttt agcaggtgca tcatactgtt        300
cccacccctc ccatcccact tctgtccagc cgcctagccc cactttcttt ttttttctttt      360 tttgagacag tctccctctt gctgaggctg gagtgcagtg gcgagatctc ggctcactgt        420
aacctccgcc tcccgggttc aagcgattct cctgcctcag cctcccaagt agctaggatt        480
acaggcgccc gccaccacgc ctggctaact tttgtatttt tagtagagat ggggtttcac        540
catgttggcc aggctggtct caaactcctg accttaagtg attcgcccac tgtggcctcc        600
caaagtgctg ggattacagg cgtgagctac cgcccccagc ccctcccatc ccacttctgt        660
ccagccccct agccctactt tctttctggg atccaggagt ccagatcccc agccccctct        720
ccagattaca ttcatccagg cacaggaaag gacagggtca ggaaaggagg actctgggcg        780
gcagcctcca cattcccctt ccacgcttgg cccccagaat ggaggagggt gtctggatta       840
ctgggcgagg tgtcctccct tcctggggac tgtggggggt ggtcaaaaga cctctatgcc        900
ccacctcctt cctccctctg ccctgctgtg cctggggcag ggggagaaca gcccacctcg        960
tgactggggg ctggcccagc ccgccctatc cctgggggag ggggcgggac aggggggagcc      1020 ctataattgg acaagtctgg gatccttgag tcctactcag ccccagcgga ggtgaaggac       1080
gtccttcccc aggagccg                                                      1098

<210> SEQ ID NO 3
<211> LENGTH: 1157
<212> TYPE: DNA
<213> ORGANISM: Homo sapiens

<400> SEQUENCE: 3
ccccagcgga ggtgaaggac gtccttcccc aggagccgac tggccaatca caggcaggaa         60
gatgaaggtt ctgtgggctg cgttgctggt cacattcctg gcaggatgcc aggccaaggt        120
ggagcaagcg gtggagacag agccggagcc cgagctgcgc cagcagaccg agtggcagag        180
cggccagcgc tgggaactgg cactgggtcg cttttgggat tacctgcgct gggtgcagac        240
actgtctgag caggtgcagg aggagctgct cagctcccaa gtcacccaag aactgagggc        300
gctgatggac gagaccatga aggagttgaa ggcctacaaa tcggaactgg aggaacaact        360
gaccccggta gcgaggagaa cgcgggcacg gctgtccaag gagctgcaga cggcgcaggc        420
ccggctgggc gcggacatgg aggacgtgtg cggccgcctg gtgcagtacc gcggcgaggt        480
gcaggccatg ctcggccaga caccgagga gctgcgggtg cgcctcgcct cccacctgcg        540
caagctgcgt aagcggctcc tccgcgatcc cgatgacctg cagaagcgcc tggcagtgta        600
ccaggccggg gcccgcgagg cgccgagcg cggcctcagc gccatccgcg agcgcctggg        660 gccccctggtg aacagggcc gcgtgcgggc cgccactgtg ggctccctgg ccggccagcc       720
gctacaggag cgggcccagg cctgggggcga gcggctgcgc gcgcggatgg aggagatggg       780
cagtcggacc cgcgaccgcc tggacgaggt gaaggagcag gtggcggagg tgcgcgccaa       840
gctggaggag caggcccagc agatacgcct gcaggccgag gccttccagg cccgcctcaa        900
gagctggttc gagcccctgg tggaagacat gcagcgccag tgggcccggc tggtggagaa       960
ggtgcaggct gccgtgggca ccagcgccgc ccctgtgccc agcgacaatc actgaacgcc       1020
```

-continued

```
gaagcctgca gccatgcgac cccacgccac cccgtgcctc ctgcctccgc gcagcctgca      1080
gcgggagacc ctgtccccgc cccagccgtc ctcctggggt ggaccctagt ttaataaaga      1140
ttcaccaagt ttcacgc                                                      1157
```

<210> SEQ ID NO 4
<211> LENGTH: 317
<212> TYPE: PRT
<213> ORGANISM: Homo sapiens

<400> SEQUENCE: 4

```
Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
                20                  25                  30

Arg Gln Gln Thr Glu Trp Gln Ser Gly Gln Arg Trp Glu Leu Ala Leu
            35                  40                  45

Gly Arg Phe Trp Asp Tyr Leu Arg Trp Val Gln Thr Leu Ser Glu Gln
        50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
                100                 105                 110

Lys Glu Leu Gln Thr Ala Gln Ala Arg Leu Gly Ala Asp Met Glu Asp
            115                 120                 125

Val Cys Gly Arg Leu Val Gln Tyr Arg Gly Glu Val Gln Ala Met Leu
        130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Pro Asp Asp Leu Gln Lys Arg
                165                 170                 175

Leu Ala Val Tyr Gln Ala Gly Ala Arg Glu Gly Ala Glu Arg Gly Leu
            180                 185                 190

Ser Ala Ile Arg Glu Arg Leu Gly Pro Leu Val Glu Gln Gly Arg Val
        195                 200                 205

Arg Ala Ala Thr Val Gly Ser Leu Ala Gly Gln Pro Leu Gln Glu Arg
        210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
                245                 250                 255

Val Arg Ala Lys Leu Glu Glu Gln Ala Gln Gln Ile Arg Leu Gln Ala
            260                 265                 270

Glu Ala Phe Gln Ala Arg Leu Lys Ser Trp Phe Glu Pro Leu Val Glu
            275                 280                 285

Asp Met Gln Arg Gln Trp Ala Gly Leu Val Glu Lys Val Gln Ala Ala
        290                 295                 300

Val Gly Thr Ser Ala Ala Pro Val Pro Ser Asp Asn His
305                 310                 315
```

<210> SEQ ID NO 5
<211> LENGTH: 317
<212> TYPE: PRT
<213> ORGANISM: Homo sapiens

```
<400> SEQUENCE: 5

Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
            20                  25                  30

Arg Gln Gln Thr Glu Trp Gln Ser Gly Gln Arg Trp Glu Leu Ala Leu
        35                  40                  45

Gly Arg Phe Trp Asp Tyr Leu Arg Trp Val Gln Thr Leu Ser Glu Gln
    50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
            100                 105                 110

Lys Glu Leu Gln Ala Ala Gln Ala Arg Leu Gly Ala Asp Met Glu Asp
        115                 120                 125

Val Cys Gly Arg Leu Val Gln Tyr Arg Gly Glu Val Gln Ala Met Leu
    130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Asp Leu Gln Lys Arg
                165                 170                 175

Leu Ala Val Tyr Gln Ala Gly Ala Arg Glu Gly Ala Glu Arg Gly Leu
            180                 185                 190

Ser Ala Ile Arg Glu Arg Leu Gly Pro Leu Val Glu Gln Gly Arg Val
        195                 200                 205

Arg Ala Ala Thr Val Gly Ser Leu Ala Gly Gln Pro Leu Gln Glu Arg
    210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
                245                 250                 255

Val Arg Ala Lys Leu Glu Glu Gln Ala Gln Gln Ile Arg Leu Gln Ala
            260                 265                 270

Glu Ala Phe Gln Ala Arg Leu Lys Ser Trp Phe Glu Pro Leu Val Glu
        275                 280                 285

Asp Met Gln Arg Gln Trp Ala Gly Leu Val Glu Lys Val Gln Ala Ala
    290                 295                 300

Val Gly Thr Ser Ala Ala Pro Val Pro Ser Asp Asn His
305                 310                 315

<210> SEQ ID NO 6
<211> LENGTH: 317
<212> TYPE: PRT
<213> ORGANISM: Homo sapiens

<400> SEQUENCE: 6

Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
            20                  25                  30

Arg Gln Gln Thr Glu Trp Gln Ser Gly Gln Arg Trp Glu Leu Ala Leu
        35                  40                  45
```

-continued

```
Gly Arg Phe Trp Asp Tyr Leu Arg Trp Val Gln Thr Leu Ser Glu Gln
    50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
                100                 105                 110

Lys Glu Leu Gln Ala Ala Gln Ala Arg Leu Gly Ala Asp Met Glu Asp
                115                 120                 125

Val Cys Gly Arg Leu Val Gln Tyr Arg Gly Glu Val Gln Ala Met Leu
        130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Asp Leu Gln Lys Arg
                165                 170                 175

Leu Ala Val Tyr Gln Ala Gly Ala Arg Glu Gly Ala Glu Arg Gly Leu
                180                 185                 190

Ser Ala Ile Arg Glu Arg Leu Gly Pro Leu Val Glu Gln Gly Arg Val
                195                 200                 205

Arg Ala Ala Thr Val Gly Ser Leu Ala Gly Gln Pro Leu Gln Glu Arg
        210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
                245                 250                 255

Val Arg Ala Lys Leu Glu Glu Gln Ala Gln Gln Ile Arg Leu Gln Ala
                260                 265                 270

Glu Ala Phe Gln Ala Arg Leu Lys Ser Trp Phe Glu Pro Leu Val Glu
                275                 280                 285

Asp Met Gln Arg Gln Trp Ala Gly Leu Val Glu Lys Val Gln Ala Ala
        290                 295                 300

Val Gly Thr Ser Ala Ala Pro Val Pro Ser Asp Asn His
305                 310                 315

<210> SEQ ID NO 7
<211> LENGTH: 317
<212> TYPE: PRT
<213> ORGANISM: Homo sapiens

<400> SEQUENCE: 7

Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
                20                  25                  30

Arg Gln Gln Thr Glu Trp Gln Ser Gly Gln Arg Trp Glu Leu Ala Leu
        35                  40                  45

Gly Arg Phe Trp Asp Tyr Leu Arg Trp Val Gln Thr Leu Ser Glu Gln
    50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
```

```
          100              105              110

Lys Glu Leu Gln Ala Ala Gln Ala Arg Leu Gly Ala Asp Met Glu Asp
        115              120              125

Val Cys Gly Arg Leu Val Gln Tyr Arg Gly Glu Val Gln Ala Met Leu
        130              135              140

Gly Gln Ser Thr Glu Glu Leu Arg Val Arg Leu Ala Ser His Leu Arg
145              150              155              160

Lys Leu Arg Lys Arg Leu Leu Arg Asp Ala Asp Asp Leu Gln Lys Arg
                165              170              175

Leu Ala Val Tyr Gln Ala Gly Ala Arg Glu Gly Ala Glu Arg Gly Leu
                180              185              190

Ser Ala Ile Arg Glu Arg Leu Gly Pro Leu Val Glu Gln Gly Arg Val
                195              200              205

Arg Ala Ala Thr Val Gly Ser Leu Ala Gly Gln Pro Leu Gln Glu Arg
        210              215              220

Ala Gln Ala Trp Gly Glu Arg Leu Arg Ala Arg Met Glu Glu Met Gly
225              230              235              240

Ser Arg Thr Arg Asp Arg Leu Asp Glu Val Lys Glu Gln Val Ala Glu
                245              250              255

Val Arg Ala Lys Leu Glu Glu Gln Ala Gln Gln Ile Arg Leu Gln Ala
                260              265              270

Glu Ala Phe Gln Ala Arg Leu Lys Ser Trp Phe Glu Pro Leu Val Glu
                275              280              285

Asp Met Gln Arg Gln Trp Ala Gly Leu Val Glu Lys Val Gln Ala Ala
        290              295              300

Val Gly Thr Ser Ala Ala Pro Val Pro Ser Asp Asn His
305              310              315
```

<210> SEQ ID NO 8

<400> SEQUENCE: 8

000

<210> SEQ ID NO 9

<400> SEQUENCE: 9

000

<210> SEQ ID NO 10
<211> LENGTH: 18
<212> TYPE: DNA
<213> ORGANISM: Artificial Sequence
<220> FEATURE:
<223> OTHER INFORMATION: A synthetic oligonucleotide sequence

<400> SEQUENCE: 10
gtggagaagg tgcaggct                                         18

<210> SEQ ID NO 11
<211> LENGTH: 21
<212> TYPE: DNA
<213> ORGANISM: Artificial Sequence
<220> FEATURE:
<223> OTHER INFORMATION: A synthetic oligonucleotide sequence

<400> SEQUENCE: 11
aagcgtaatc tggaacatcg t                                     21

-continued

```
<210> SEQ ID NO 12
<211> LENGTH: 20
<212> TYPE: DNA
<213> ORGANISM: Artificial Sequence
<220> FEATURE:
<223> OTHER INFORMATION: A synthetic oligonucleotide sequence

<400> SEQUENCE: 12
ccctgtgccc agcgacaatc                                                            20

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20
<211> LENGTH: 21
<212> TYPE: RNA
<213> ORGANISM: Artificial Sequence
<220> FEATURE:
<223> OTHER INFORMATION: A synthetic oligonucleotide sequence

<400> SEQUENCE: 20
gguggagcaa gcgguggagu u                                                          21

<210> SEQ ID NO 21
<211> LENGTH: 21
<212> TYPE: RNA
<213> ORGANISM: Artificial Sequence
<220> FEATURE:
```

-continued

```
<223> OTHER INFORMATION: A synthetic oligonucleotide sequence

<400> SEQUENCE: 21
ggaguugaag gccuacaaau u                                              21

<210> SEQ ID NO 22
<211> LENGTH: 21
<212> TYPE: RNA
<213> ORGANISM: Artificial Sequence
<220> FEATURE:
<223> OTHER INFORMATION: A synthetic oligonucleotide sequence

<400> SEQUENCE: 22
ggaagacaug cagcgccagu u                                              21

<210> SEQ ID NO 23
<211> LENGTH: 21
<212> TYPE: RNA
<213> ORGANISM: Artificial Sequence
<220> FEATURE:
<223> OTHER INFORMATION: A synthetic oligonucleotide sequence

<400> SEQUENCE: 23
gcgcgcggau ggaggagauu u                                              21

<210> SEQ ID NO 24
<211> LENGTH: 132
<212> TYPE: DNA
<213> ORGANISM: Artificial Sequence
<220> FEATURE:
<223> OTHER INFORMATION: A synthetic oligonucleotide sequence

<400> SEQUENCE: 24
ctggaggctt gctgaaggct gtatgctgat ttgtaggcct tcaactcctg ttttggccac    60
tgactgacag gagtgaggcc tacaaatcag gacacaaggc ctgttactag cactcacatg   120
gaacaaatgg cc                                                       132

<210> SEQ ID NO 25
<211> LENGTH: 150
<212> TYPE: DNA
<213> ORGANISM: Artificial Sequence
<220> FEATURE:
<223> OTHER INFORMATION: A synthetic oligonucleotide sequence

<400> SEQUENCE: 25
ctggaggctt gctttgggct gtatgctgat ttgtaggcct tcaactcctg ttttggccac    60
tgactgacag gagttgaagt cacaaatcag gacacaaggc cctttatcag cactcacatg   120
gaacaaatgg ccaccgtggg aggatgacaa                                    150

<210> SEQ ID NO 26
<211> LENGTH: 150
<212> TYPE: DNA
<213> ORGANISM: Artificial Sequence
<220> FEATURE:
<223> OTHER INFORMATION: A synthetic oligonucleotide sequence

<400> SEQUENCE: 26
ctggaggctt gctttgggct gtatgctgtt ccgatttgta ggccttcaag ttttggccac    60
tgactgactt gaagtcacaa atcggaacag gacacaaggc cctttatcag cactcacatg   120
gaacaaatgg ccaccgtggg aggatgacaa                                    150
```

-continued

```
<210> SEQ ID NO 27
<211> LENGTH: 951
<212> TYPE: DNA
<213> ORGANISM: Artificial Sequence
<220> FEATURE:
<223> OTHER INFORMATION: A synthetic oligonucleotide sequence

<400> SEQUENCE: 27
atgaaggttc tgtgggctgc gttgctggtc acattcctgg caggatgcca ggccaaggtg      60
gagcaagcgg tggagacaga gccggagccc gagctgcgcc agcagaccga gtggcagagc     120
ggccagcgct gggaactggc actgggtcgc ttttgggatt acctgcgctg ggtgcagaca     180
ctgtctgagc aggtgcagga ggagctgctc agctcccagg tcacccagga actgagggcg     240
ctgatggacg agaccatgaa agaacttaaa gcatataaga gtgagctgga ggaacaactg     300
accccggtgg cggaggagac gcgggcacgg ctgtccaagg agctgcaggc ggcgcaggcc     360
cggctgggcg cggacatgga ggacgtgtgc ggccgcctgg tgcagtaccg cggcgaggtg     420
caggccatgc tcggccagag caccgaggag ctgcgggtgc gcctcgcctc ccacctgcgc     480
aagctgcgta agcggctcct ccgcgatgcc gatgacctgc agaagtgcct ggcagtgtac     540
caggccgggg cccgcgaggg cgccgagcgc ggcctcagcg ccatccgcga gcgcctgggg     600
cccctggtgg aacagggccg cgtgcgggcc gccactgtgg gctccctggc cggccagccg     660
ctacaggagc gggcccaggc ctggggcgag cggctgcgcg cgcggatgga ggagatgggc     720
agccggaccc gcgaccgcct ggacgaggtg aaggagcagg tggcggaggt gcgcgccaag     780
ctggaggagc aggcccagca gatacgcctg caggccgagg ccttccaggc ccgcctcaag     840
agctggttcg agcccctggt ggaagacatg cagcgccagt gggccgggct ggtggagaag     900
gtgcaggctg ccgtgggcac cagcgccgcc cctgtgccca gcgacaatca c              951

<210> SEQ ID NO 28
<211> LENGTH: 951
<212> TYPE: DNA
<213> ORGANISM: Artificial Sequence
<220> FEATURE:
<223> OTHER INFORMATION: A synthetic oligonucleotide sequence

<400> SEQUENCE: 28
atgaaggttc tgtgggctgc gttgctggtc acattcctgg caggatgcca ggccaaggtg      60
gagcaagcgg tggagacaga gccggagccc gagctgcgcc agcagaccga gtggcagagc     120
ggccagcgct gggaactggc actgggtcgc ttttgggatt acctgcgctg ggtgcagaca     180
ctgtctgagc aggtgcagga ggagctgctc agctcccagg tcacccagga actgagggcg     240
ctgatggacg agaccatgaa agaactcaaa gcatataaga gtgagctgga ggaacaactg     300
accccggtgg cggaggagac gcgggcacgg ctgtccaagg agctgcaggc ggcgcaggcc     360
cggctgggcg cggacatgga ggacgtgtgc ggccgcctgg tgcagtaccg cggcgaggtg     420
caggccatgc tcggccagag caccgaggag ctgcgggtgc gcctcgcctc ccacctgcgc     480
aagctgcgta agcggctcct ccgcgatgcc gatgacctgc agaagtgcct ggcagtgtac     540
caggccgggg cccgcgaggg cgccgagcgc ggcctcagcg ccatccgcga gcgcctgggg     600
cccctggtgg aacagggccg cgtgcgggcc gccactgtgg gctccctggc cggccagccg     660
ctacaggagc gggcccaggc ctggggcgag cggctgcgcg cgcggatgga ggagatgggc     720
agccggaccc gcgaccgcct ggacgaggtg aaggagcagg tggcggaggt gcgcgccaag     780
ctggaggagc aggcccagca gatacgcctg caggccgagg ccttccaggc ccgcctcaag     840
```

-continued

```
agctggttcg agcccctggt ggaagacatg cagcgccagt gggccgggct ggtggagaag      900
gtgcaggctg ccgtgggcac cagcgccgcc cctgtgccca gcgacaatca c               951

<210> SEQ ID NO 29
<211> LENGTH: 951
<212> TYPE: DNA
<213> ORGANISM: Artificial Sequence
<220> FEATURE:
<223> OTHER INFORMATION: A synthetic oligonucleotide sequence

<400> SEQUENCE: 29
atgaaggttc tgtgggctgc gttgctggtc acattcctgg caggatgcca ggccaaggtg       60
gagcaagcgg tggagacaga gccggagccc gagctgcgcc agcagaccga gtggcagagc      120
ggccagcgct gggaactggc actgggtcgc ttttgggatt acctgcgctg ggtgcagaca      180
ctgtctgagc aggtgcagga ggagctgctc agctcccagg tcacccagga actgagggcg      240
ctgatggacg agaccatgaa agaacttaaa gcttataaga gtgagctgga ggaacaactg      300
accccggtgg cggaggagac gcgggcacgg ctgtccaagg agctgcaggc ggcgcaggcc      360
cggctgggcg cggacatgga ggacgtgtgc ggccgcctgg tgcagtaccg cggcgaggtg      420
caggccatgc tcggccagag caccgaggag ctgcgggtgc gcctcgcctc ccacctgcgc      480
aagctgcgta agcggctcct ccgcgatgcc gatgacctgc agaagtgcct ggcagtgtac      540
caggccgggg cccgcgaggg cgccgagcgc ggcctcagcg ccatccgcga gcgcctgggg      600
cccctggtgg aacagggccg cgtgcgggcc gccactgtgg gctccctggc cggccagccg      660
ctacaggagc gggcccaggc ctggggcgag cggctgcgcg cgcggatgga ggagatgggc      720
agccggaccc gcgaccgcct ggacgaggtg aaggagcagg tggcggaggt gcgcgccaag      780
ctggaggagc aggcccagca gatacgcctg caggccgagg ccttccaggc ccgcctcaag      840
agctggttcg agcccctggt ggaagacatg cagcgccagt gggccgggct ggtggagaag      900
gtgcaggctg ccgtgggcac cagcgccgcc cctgtgccca gcgacaatca c               951

<210> SEQ ID NO 30
<211> LENGTH: 951
<212> TYPE: DNA
<213> ORGANISM: Artificial Sequence
<220> FEATURE:
<223> OTHER INFORMATION: A synthetic oligonucleotide sequence

<400> SEQUENCE: 30
atgaaggttc tgtgggctgc gttgctggtc acattcctgg caggatgcca ggccaaggtg       60
gagcaagcgg tggagacaga gccggagccc gagctgcgcc agcagaccga gtggcagagc      120
ggccagcgct gggaactggc actgggtcgc ttttgggatt acctgcgctg ggtgcagaca      180
ctgtctgagc aggtgcagga ggagctgctc agctcccagg tcacccagga actgagggcg      240
ctgatggacg agaccatgaa agaacttaaa gcatataaga gcgagctgga ggaacaactg      300
accccggtgg cggaggagac gcgggcacgg ctgtccaagg agctgcaggc ggcgcaggcc      360
cggctgggcg cggacatgga ggacgtgtgc ggccgcctgg tgcagtaccg cggcgaggtg      420
caggccatgc tcggccagag caccgaggag ctgcgggtgc gcctcgcctc ccacctgcgc      480
aagctgcgta agcggctcct ccgcgatgcc gatgacctgc agaagtgcct ggcagtgtac      540
caggccgggg cccgcgaggg cgccgagcgc ggcctcagcg ccatccgcga gcgcctgggg      600
cccctggtgg aacagggccg cgtgcgggcc gccactgtgg gctccctggc cggccagccg      660
ctacaggagc gggcccaggc ctggggcgag cggctgcgcg cgcggatgga ggagatgggc      720
```

-continued

```
agccggaccc gcgaccgcct ggacgaggtg aaggagcagg tggcggaggt gcgcgccaag     780
ctggaggagc aggcccagca gatacgcctg caggccgagg ccttccaggc ccgcctcaag     840
agctggttcg agcccctggt ggaagacatg cagcgccagt gggccgggct ggtggagaag     900
gtgcaggctg ccgtgggcac cagcgccgcc cctgtgccca gcgacaatca c     951
```

```
<210> SEQ ID NO 31
<211> LENGTH: 951
<212> TYPE: DNA
<213> ORGANISM: Artificial Sequence
<220> FEATURE:
<223> OTHER INFORMATION: A synthetic oligonucleotide sequence

<400> SEQUENCE: 31
```

```
atgaaggttc tgtgggctgc gttgctggtc acattcctgg caggatgcca ggccaaggtg      60
gagcaagcgg tggagacaga gccggagccc gagctgcgcc agcagaccga gtggcagagc     120
ggccagcgct gggaactggc actgggtcgc ttttgggatt acctgcgctg ggtgcagaca     180
ctgtctgagc aggtgcagga ggagctgctc agctcccagg tcacccagga actgagggcg     240
ctgatggacg agaccatgaa agaactcaaa gcttataaga gtgagctgga ggaacaactg     300
accccggtgg cggaggagac gcgggcacgg ctgtccaagg agctgcaggc ggcgcaggcc     360
cggctgggcg cggacatgga ggacgtgtgc ggccgcctgg tgcagtaccg cggcgaggtg     420
caggccatgc tcggccagag caccgaggag ctgcgggtgc gcctcgcctc ccacctgcgc     480
aagctgcgta agcggctcct ccgcgatgcc gatgacctgc agaagtgcct ggcagtgtac     540
caggccgggg cccgcgaggg cgccgagcgc ggcctcagcg ccatccgcga gcgcctgggg     600
cccctggtgg aacagggccg cgtgcgggcc gccactgtgg gctccctggc cggccagccg     660
ctacaggagc gggcccaggc ctggggcgag cggctgcgcg cgcggatgga ggagatgggc     720
agccggaccc gcgaccgcct ggacgaggtg aaggagcagg tggcggaggt gcgcgccaag     780
ctggaggagc aggcccagca gatacgcctg caggccgagg ccttccaggc ccgcctcaag     840
agctggttcg agcccctggt ggaagacatg cagcgccagt gggccgggct ggtggagaag     900
gtgcaggctg ccgtgggcac cagcgccgcc cctgtgccca gcgacaatca c     951
```

```
<210> SEQ ID NO 32
<211> LENGTH: 951
<212> TYPE: DNA
<213> ORGANISM: Artificial Sequence
<220> FEATURE:
<223> OTHER INFORMATION: A synthetic oligonucleotide sequence

<400> SEQUENCE: 32
```

```
atgaaggttc tgtgggctgc gttgctggtc acattcctgg caggatgcca ggccaaggtg      60
gagcaagcgg tggagacaga gccggagccc gagctgcgcc agcagaccga gtggcagagc     120
ggccagcgct gggaactggc actgggtcgc ttttgggatt acctgcgctg ggtgcagaca     180
ctgtctgagc aggtgcagga ggagctgctc agctcccagg tcacccagga actgagggcg     240
ctgatggacg agaccatgaa agaactcaaa gcatataaga gcgagctgga ggaacaactg     300
accccggtgg cggaggagac gcgggcacgg ctgtccaagg agctgcaggc ggcgcaggcc     360
cggctgggcg cggacatgga ggacgtgtgc ggccgcctgg tgcagtaccg cggcgaggtg     420
caggccatgc tcggccagag caccgaggag ctgcgggtgc gcctcgcctc ccacctgcgc     480
aagctgcgta agcggctcct ccgcgatgcc gatgacctgc agaagtgcct ggcagtgtac     540
```

```
caggccgggg cccgcgaggg cgccgagcgc ggcctcagcg ccatccgcga gcgcctgggg        600
cccctggtgg aacagggccg cgtgcgggcc gccactgtgg gctccctggc cggccagccg        660
ctacaggagc gggcccaggc ctggggcgag cggctgcgcg cgcggatgga ggagatgggc        720
agccggaccc gcgaccgcct ggacgaggtg aaggagcagg tggcggaggt gcgcgccaag        780
ctggaggagc aggcccagca gatacgcctg caggccgagg ccttccaggc ccgcctcaag        840
agctggttcg agcccctggt ggaagacatg cagcgccagt gggccgggct ggtggagaag        900
gtgcaggctg ccgtgggcac cagcgccgcc cctgtgccca gcgacaatca c               951
```

```
<210> SEQ ID NO 33
<211> LENGTH: 951
<212> TYPE: DNA
<213> ORGANISM: Artificial Sequence
<220> FEATURE:
<223> OTHER INFORMATION: A synthetic oligonucleotide sequence

<400> SEQUENCE: 33
```

```
atgaaggttc tgtgggctgc gttgctggtc acattcctgg caggatgcca ggccaaggtg         60
gagcaagcgg tggagacaga gccggagccc gagctgcgcc agcagaccga gtggcagagc        120
ggccagcgct gggaactggc actgggtcgc ttttgggatt acctgcgctg ggtgcagaca        180
ctgtctgagc aggtgcagga ggagctgctc agctcccagg tcacccagga actgagggcg        240
ctgatggacg agaccatgaa agaacttaaa gcttataaga gcgagctgga ggaacaactg        300
accccggtgg cggaggagac gcgggcacgg ctgtccaagg agctgcaggc ggcgcaggcc        360
cggctgggcg cggacatgga ggacgtgtgc ggccgcctgg tgcagtaccg cggcgaggtg        420
caggccatgc tcggccagag caccgaggag ctgcgggtgc gcctcgcctc ccacctgcgc        480
aagctgcgta agcggctcct ccgcgatgcc gatgacctgc agaagtgcct ggcagtgtac        540
caggccgggg cccgcgaggg cgccgagcgc ggcctcagcg ccatccgcga gcgcctgggg        600
cccctggtgg aacagggccg cgtgcgggcc gccactgtgg gctccctggc cggccagccg        660
ctacaggagc gggcccaggc ctggggcgag cggctgcgcg cgcggatgga ggagatgggc        720
agccggaccc gcgaccgcct ggacgaggtg aaggagcagg tggcggaggt gcgcgccaag        780
ctggaggagc aggcccagca gatacgcctg caggccgagg ccttccaggc ccgcctcaag        840
agctggttcg agcccctggt ggaagacatg cagcgccagt gggccgggct ggtggagaag        900
gtgcaggctg ccgtgggcac cagcgccgcc cctgtgccca gcgacaatca c               951
```

```
<210> SEQ ID NO 34
<211> LENGTH: 951
<212> TYPE: DNA
<213> ORGANISM: Artificial Sequence
<220> FEATURE:
<223> OTHER INFORMATION: A synthetic oligonucleotide sequence

<400> SEQUENCE: 34
```

```
atgaaggttc tgtgggctgc gttgctggtc acattcctgg caggatgcca ggccaaggtg         60
gagcaagcgg tggagacaga gccggagccc gagctgcgcc agcagaccga gtggcagagc        120
ggccagcgct gggaactggc actgggtcgc ttttgggatt acctgcgctg ggtgcagaca        180
ctgtctgagc aggtgcagga ggagctgctc agctcccagg tcacccagga actgagggcg        240
ctgatggacg agaccatgaa agaactcaaa gcttataaga gcgagctgga ggaacaactg        300
accccggtgg cggaggagac gcgggcacgg ctgtccaagg agctgcaggc ggcgcaggcc        360
cggctgggcg cggacatgga ggacgtgtgc ggccgcctgg tgcagtaccg cggcgaggtg        420
```

-continued

```
caggccatgc tcggccagag caccgaggag ctgcgggtgc gcctcgcctc ccacctgcgc      480
aagctgcgta agcggctcct ccgcgatgcc gatgacctgc agaagtgcct ggcagtgtac      540
caggccgggg cccgcgaggg cgccgagcgc ggcctcagcg ccatccgcga gcgcctgggg      600
cccctggtgg aacagggccg cgtgcgggcc gccactgtgg gctccctggc cggccagccg      660
ctacaggagc gggcccaggc ctggggcgag cggctgcgcg cgcggatgga ggagatgggc      720
agccggaccc gcgaccgcct ggacgaggtg aaggagcagg tggcggaggt gcgcgccaag      780
ctggaggagc aggcccagca gatacgcctg caggccgagg ccttccaggc ccgcctcaag      840
agctggttcg agcccctggt ggaagacatg cagcgccagt gggccgggct ggtggagaag      900
gtgcaggctg ccgtgggcac cagcgccgcc cctgtgccca gcgacaatca c               951
```

APOE GENE THERAPY

CROSS-REFERENCE TO RELATED APPLICATIONS

This application This application is U.S. National Stage Filing under 35 U.S.C. 371 of International Patent Application Serial No. PCT/US2020/070822, filed Nov. 25, 2020, and published as WO 2021/108809 A1 on Jun. 3, 2021, which claims the benefit of the filing date of U.S. application No. 62/939,999, filed on Nov. 25, 2019, the disclosures of which are incorporated by reference herein.

BACKGROUND

Alzheimer's disease (AD) directly affects 5 million Americans and is rapidly increasing in prevalence and economic impact. Existing drugs have little impact on the underlying disease process and no preventive therapies are currently available. Inheritance of the variant APOE4 conveys a high risk for the development of AD, while inheritance of APOE2 gene is protective, reducing the risk of developing AD by ~50% and delaying the age of onset. APOE4 is associated with increased brain amyloid load and greater memory impairment in AD. Conversely, APOE2 attenuates these effects. Previous studies have shown that adeno-associated virus (AAV) gene delivery of the human APOE2 coding sequence to the CNS of a murine model expressing human APOE4 reduces the amount of amyloid-1 peptide and amyloid burden (Zhao et al. 2016). In humans, the odds ratio of developing AD with E4/E4 homozygous genotype is 14.9 and is reduced to 2.6 in E2/E4 heterozygotes. Recent reports have suggested that APOE4 is associated with abnormal brain function apart from its role in promoting amyloid production.

SUMMARY

The disclosure provides for a gene therapy vector comprising an expression cassette coding for a mammalian apolipoprotein E (APOE) that is protective or includes a substitution, e.g., relative to APOE4, in a region that binds a lipoprotein receptor, e.g., LDLR, or binds heparan sulfate proteoglycan (HSPG), e.g., a region such as that from position 135 to 151. In one embodiment, the mammalian APOE in the gene therapy vector has a residue other than arginine, histidine or lysine at at least one of positions 112, 136, or 158. In one embodiment, the mammalian APOE in the gene therapy vector has a residue other than arginine at positions 112 and 136. In one embodiment, the mammalian APOE in the gene therapy vector has a residue other than arginine at positions 136 and 158. In one embodiment, the mammalian APOE in the gene therapy vector has a residue other than arginine at positions 112, 136 and 158. In one embodiment, the apolipoprotein E is a human apolipoprotein E. In one embodiment, the residue other than arginine is serine, leucine, valine, glycine, isoleucine, alanine, threonine, asparagine, cysteine, or methionine. In one embodiment, the residue other than arginine is serine, threonine, asparagine, cysteine, or glutamine. In one embodiment, position 112 has a cysteine, methionine, valine, threonine, alanine, serine, arginine, glycine or isoleucine. In one embodiment, position 112 has a cysteine. In one embodiment, position 136 has a threonine, cysteine, methionine, arginine or a serine. In one embodiment, position 136 has a serine. In one embodiment, position 158 has a cysteine, methionine, valine, threonine, alanine, serine, arginine, glycine or isoleucine. In one embodiment, position 158 has an arginine or a cysteine. In one embodiment, two of positions 112, 136 or 158 have an arginine. In one embodiment, position 112 does not have an arginine. In one embodiment, position 136 does not have an arginine. In one embodiment, position 158 does not have an arginine. In one embodiment, the mammalian APOE in the gene therapy vector has a Cys at position 112, a Ser at position 136 and a Cys at position 158. In one embodiment, the mammalian APOE in the gene therapy vector has a Cys at position 112, a Ser at position 136 and a Arg at position 158. In one embodiment, the gene therapy vector is a viral gene therapy vector. In one embodiment, the gene therapy vector is an adenovirus, adeno-associated virus (AAV), retrovirus or lentivirus vector. In one embodiment, the viral gene therapy vector is a rAAV vector. In one embodiment, the AAV vector is pseudotyped, e.g., with AAVrh.10, AAV8, AAV9, AAV5, AAVhu.37, AAVhu.20, AAVhu.43, AAVhu.8, AAVhu.2, or AAV7 capsid. In one embodiment, the AAV vector is pseudotyped with AAVrh.10, AAV8, or AAV5. In one embodiment, the AAV vector is AAV2, AAV5, AAV7, AAV8, AAV9 or AAVrh.10. In one embodiment, the gene therapy vector further comprises a nucleotide sequence having RNAi sequences corresponding to APOE4 for inhibition of APOE4 mRNA. In one embodiment, a second gene therapy vector comprises a nucleotide sequence having RNAi sequences corresponding to APOE4 for inhibition of APOE4 mRNA. In one embodiment, the nucleotide sequence is linked to a second promoter. In one embodiment, the second promoter is a PolIII promoter. In one embodiment, the RNAi comprises miRNA including a plurality of miRNA sequences. In one embodiment, the RNAi comprises sRNA including a plurality of siRNA sequences. In one embodiment, the vector is a plasmid. In one embodiment, the mammalian apolipoprotein gene in the vector has 0112, 5136 and R158 or a 0112, 5136 and 0158. In one embodiment, a second gene therapy vector comprises a nucleotide sequence having nucleic acid sequences encoding an anti-APOE4 or anti-heparan antibody.

Also provided is a pharmaceutical composition comprising the gene therapy vector. In one embodiment, the vector is a viral vector. In one embodiment, the vector is a rAAV vector. In one embodiment, the amount of the vector in the composition is about $1 \times 10^{11}$ to about $1 \times 10^{16}$ genome copies. In one embodiment, the amount of the vector in the composition is about $1 \times 10^{12}$ to about $1 \times 10^{15}$ genome copies. In one embodiment, the amount of the vector in the composition is about $1 \times 10^{11}$ to about $1 \times 10^{13}$ genome copies. In one embodiment, the amount of the vector in the composition is about $1 \times 10^{13}$ to about $1 \times 10^{15}$ genome copies. In one embodiment, the pharmaceutical composition further comprises a pharmaceutically acceptable carrier.

Further provided is a method to prevent, inhibit or treat Alzheimer's disease including preventing or treating one or more symptoms thereof such as dementia, or other tauopathy or cognitive impairment in a mammal. In one embodiment, prior to administration, the mammal has or is at risk of increased amyloid plaque and/or increased tau in the brain, e.g., relative to an age-matched mammal or a mammal with a decreased risk of Alzheimer's disease or other tauopathy or cognitive impairment. In one embodiment, the mammal has cognitive impairment. The method includes administering to the mammal an effective amount of a composition comprising the gene therapy vector. In one embodiment, the composition comprises liposomes comprising the vector. In one embodiment, the composition comprises nanoparticles comprising the vector. In one embodiment, the mammal is a E2/E4 heterozygote. In one embodiment, the mammal is a E4/E4 homozygote. In one embodiment, the mammal is a E31E4 heterozygote. In one embodiment, the mammal is a E2/E3 heterozygote. In one embodiment, the mammal is a human. In one embodiment, the human is an adult, e.g., over the age of 20 years old, e.g., at least 40, 50 or 60 years old. In one embodiment, the human is a juvenile, e.g., from 10 to 20 years old. In one embodiment, the human is a child, e.g., under the age of 10 years old. In one embodiment, the composition is administered to a human at birth or within 1, 2, 3, 4 or 5 years of birth. In one embodiment, the composition is systemically administered. In one embodiment, the composition is orally administered. In one embodiment, the composition is intravenously administered. In one embodiment, the composition is locally administered. In one embodiment, the composition is injected. In one embodiment, the composition is administered to the central nervous system. In one embodiment, the composition is administered to the brain. In one embodiment, the composition is a sustained release composition. In one embodiment, administration of the gene therapy vector is effective to prevent or inhibit accumulation of amyloid plaques. In one embodiment, administration of the gene therapy vector is effective to prevent or inhibit tau pathology. In one embodiment, administration of the gene therapy vector is effective to prevent or inhibit accumulation of amyloid plaques and prevent or inhibit tau pathology.

In addition, a method to prevent, inhibit or treat a disease associated with APOE4 expression in a mammal is provided. The method includes administering to the mammal an effective amount of a composition comprising the gene therapy vector. In one embodiment, the composition comprises liposomes comprising the vector. In one embodiment, the composition comprises nanoparticles comprising the vector. In one embodiment, the mammal is a E2/E4 heterozygote. In one embodiment, mammal is a E4/E4 homozygote. In one embodiment, the mammal is a E3/E4 heterozygote. In one embodiment, the mammal is a E4/E4 homozygote. In one embodiment, the mammal is a human. In one embodiment, the composition is systemically administered. In one embodiment, the composition is orally administered. In one embodiment, the composition is intravenously administered. In one embodiment, the composition is locally administered. In one embodiment, the composition is injected. In one embodiment, the composition is administered to the central nervous system. In one embodiment, the composition is administered to the brain. In one embodiment, the composition is a sustained release composition.

A method to reduce binding to heparin sulfate proteoglycans in a mammal is provided that includes administering to the mammal an effective amount of a composition comprising the gene therapy vector. In one embodiment, the composition comprises liposomes comprising the vector. In one embodiment, the composition comprises nanoparticles comprising the vector. In one embodiment, the mammal is a E2/E4 heterozygote. In one embodiment, the mammal is a E4/E4 homozygote. In one embodiment, the mammal is a E3/E4 heterozygote. In one embodiment, the mammal is a E4/E4 homozygote. In one embodiment, the mammal is a human. In one embodiment, the composition is systemically administered. In one embodiment, the composition is orally administered. In one embodiment, the composition is intravenously administered. In one embodiment, the composition is locally administered. In one embodiment, the composition is injected. In one embodiment, the composition is administered to the central nervous system. In one embodiment, the composition is administered to the brain. In one embodiment, the composition is a sustained release composition.

In one embodiment, the composition is administered via a catheter. In one embodiment, the composition is intraventricularly administered. In one embodiment, the composition is intracranially administered. In one embodiment, the composition is administered to the lumbar region. In one embodiment, the composition is administered to the cisterna magna. In one embodiment, the composition is administered via burr holes to the brain. In one embodiment, the composition is administered below C1-C2.

In one embodiment, the composition is administered so that expression of the encoded gene product, e.g., modified APOE or an antibody that binds heparan, is similar to expression levels of APOE4 in the mammal. In one embodiment, the ratio of secreted vector encoded gene product to secreted APOE4 in the mammal is 1:1. In one embodiment, the ratio of secreted vector encoded gene product to secreted APOE4 in the mammal is 2:1. In one embodiment, the ratio of secreted vector encoded gene product to secreted APOE4 in the mammal is 0.5:1. In one embodiment, the ratio of secreted vector encoded gene product to secreted APOE4 in the mammal is 0.1:1. In one embodiment, the ratio of secreted vector encoded gene product to secreted APOE4 in the mammal is 3:1. In one embodiment, the levels of expression of the encoded gene product in the mammal prevent or inhibit cognitive decline (deterioration). In one embodiment, the levels of expression of the encoded gene product in the mammal reduce tau tangles and amyloid accumulation.

A method to prevent, inhibit or treat a lipid disorder in a mammal is provided that includes administering to the mammal an effective amount of a composition comprising the gene therapy vector. In one embodiment, the composition comprises liposomes comprising the vector. In one embodiment, the composition comprises nanoparticles comprising the vector. In one embodiment, the mammal is a E2/E4 heterozygote. In one embodiment, the mammal is a E4/E4 homozygote. In one embodiment, the mammal is a E3/E4 heterozygote. In one embodiment, the mammal is a E4/E4 homozygote. In one embodiment, the mammal is a human. In one embodiment, the composition is systemically administered. In one embodiment, the composition is orally administered. In one embodiment, the composition is intravenously administered. In one embodiment, the composition is locally administered. In one embodiment, the composition is injected. In one embodiment, the composition is administered to the central nervous system. In one embodiment, the composition is administered to the brain. In one embodiment, the composition is a sustained release composition.

In one embodiment, a gene therapy vector comprises an AAV expression vector encoding a human APOE gene modified as described herein and either in cis or in trans artificial miRNA(s) that target endogenous APOE4. This vector system silences the expression of detrimental endogenous APOE4 in combination with supplementation of the beneficial APOE gene from a gene therapy vector, e.g., an AAV vector. Exemplary microRNA sequences were incorporated in the CAG promoter intron or polyA tail of the vector transgene plasmid coding for the human APOE coding sequence. Alternatively, the microRNA(s) may be inserted between a PolIII promoter, e.g., a US promoter, and terminator following the polyA site of the APOE expression cassette. The vector-derived human APOE DNA sequence may include silent nucleotide changes to ensure that it is not suppressed by the microRNAs and can include a tag such as a HA tag for detection, e.g., for pre-clinical detection studies. In one embodiment, the expression construct is packaged into an AAV capsid of a serotype that targets astrocytes and glial cells (for example AAV9 but can be other vectors), the prominent sites of endogenous APOE expression in the CNS.

The vectors described herein may be employed to prevent, inhibit or treat cognitive impairment, dementia, Alzheimer's disease, e.g., autosomal dominant, late onset, or early onset. In one embodiment, the mammal has reduced fibrillar amyloid-beta plaque burden, reduced levels of paired helical filament tau, or decreased neurodegeneration, post-administration of the vector. In one embodiment, the vectors described herein may be employed to prevent, inhibit or treat cognitive impairment, e.g., associated with traumatic brain injury, stroke, transient ischemic attack, dementia, Creutzfeldt-Jakob disease, multiple sclerosis, prion disease, Pick's disease, corticobasal degeneration, Parkinson's disease, Lewy body dementia, Progressive supranuclear palsy; Dementia pugilistica (chronic traumatic encephalopathy); frontotemporal dementia and parkinsonism linked to chromosome 17; Lytico-Bodig disease; Tangle-predominant dementia; Ganglioglioma and gangliocytoma; Meningioangiomatosis; Subacute sclerosing panencephalitis; lead encephalopathy, tuberous sclerosis, Hallervorden-Spatz disease, and lipofuscinosis; Argyrophilic grain disease; or Frontotemporal lobar degeneration.

The vectors described herein may also be employed to prevent, inhibit or treat one or more symptoms associated with hyperlipoproteinemia, e.g., Type 1, Type 2, Type 3, Type 4 or Type 5. In one embodiment, the amount of vector administered decreases circulating cholesterol, e.g., decreases VLDL and/or LDL, decreases intermediate density lipoproteins, decreases plasma levels of cholesterol and/or triglycerides, decreases triglycerides containing VLDL, decreases lipid accumulation in the glomerular capillaries, decreases intraglomerular lipoprotein or decreases thrombi.

BRIEF DESCRIPTION OF FIGURES

FIG. 1. APOE alleles, prevalence and associated risk of developing Alzheimer's disease.

FIG. 2. Exemplary viral gene therapy.

FIG. 3. Exemplary route of administration of gene therapy.

FIG. 4. Selected amino acid residues for different APOE alleles, prevalence and associated risk of developing Alzheimer's disease.

Figure 5:
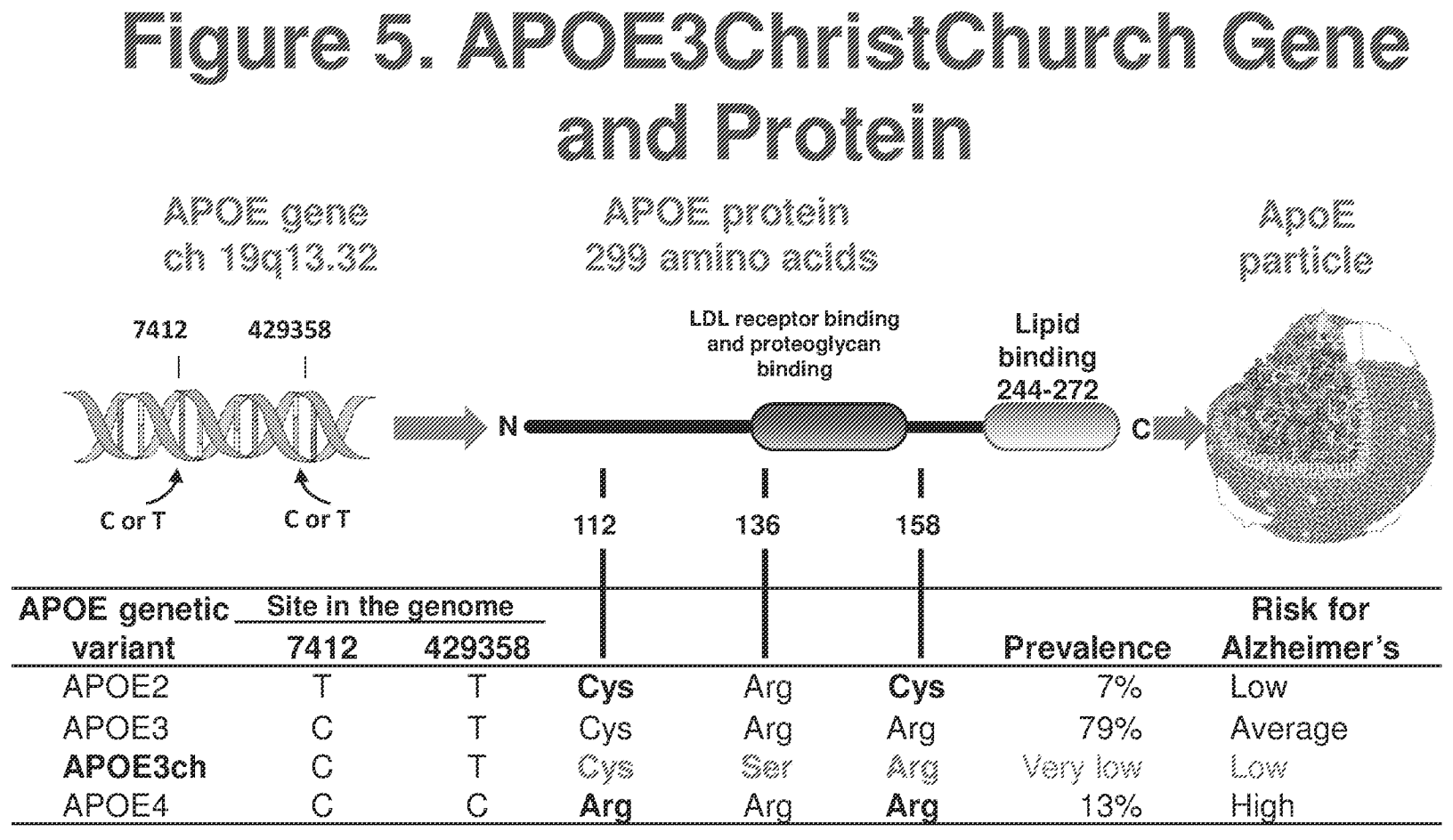

FIG. 5. Nucleotide residues at two positions in different APOE alleles.

FIG. 6. APOE3ch mutation.

FIG. 7. Impact of APOE3ch mutation.

FIG. 8. Affinity of APOE3ch for heparin.

FIG. 9. Possible mechanism for APOE or tau binding to HSPGs.

FIG. 10. Exemplary gene therapy approaches to prevent, inhibit or treat diseases associated with expression of certain APOE alleles.

6

V vector to deliver the coding sequence of APOE2 and APOE3 variants with the Christchurch variant to decrease the risk for AD.

Figure 13:
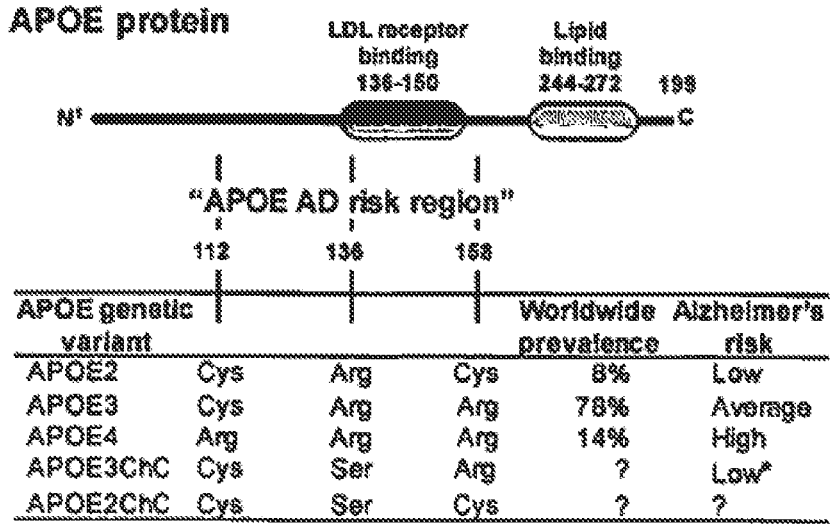

FIG. 13. APOE variants, the risk for AD, and proposed gene therapy to protect against APOE4. APOE2, 3 and 4 are common variants (Hefferman et al., 2016; ALXFORUM, 2010). APOE3ChC is the variant superimposed on PSEN 1-E290A in the case report of the Christchurch mutation on the APOE3 background protecting from the PSEN 1-E290A dominant variant causing early onset AD19. APOE3ChC and APOE2ChC variants may be therapies to mitigate the high risk of AD in APOE4 homozygotes. The APOE2ChC variant has not been observed in nature, but it may be more effective than APOE3ChC. *Low in the context of PSEN 1-E290A.

Figure 14:
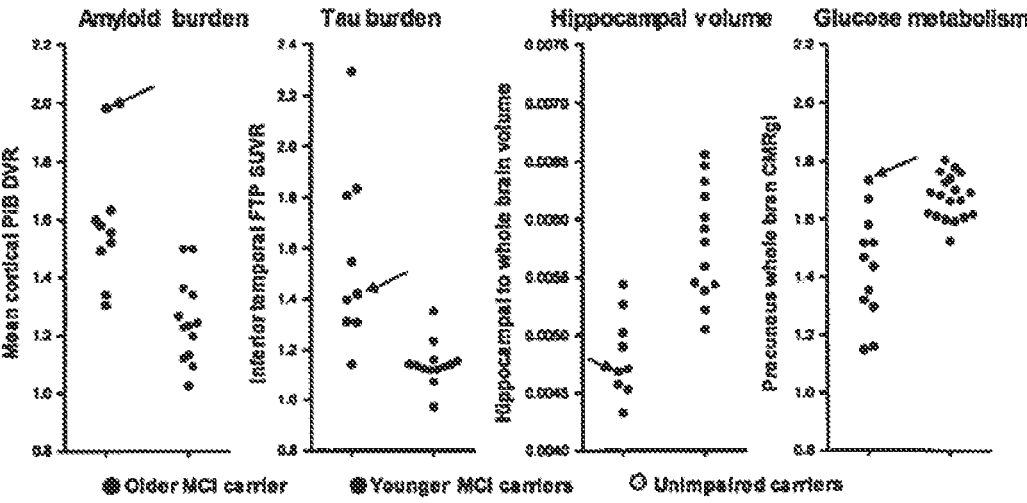

FIG. 14. Studies supporting the relative effect of APOE3ChC in a female with the PSEN1-E280 mutation. Shown are quantitative data for mean cortical amyloid plaque burden (Pittsburgh Compound 8, PET), inferior temporal cortex PHF tau burden (Florataucipir PET), hippocampal volume (MRI) and precuneus glucose metabolism (Fludeoxyglucose PET). Black dots—PSEN1 carriers with MCI onset at typical young age; grey dots—PSEN1 carriers that have not yet developed MCI; the subject with PSEN1 carrier+APOE3ChC variant (red dot with arrow). Figure modified from Arboleda-Velasquez et al. (2019).

Figure 15:
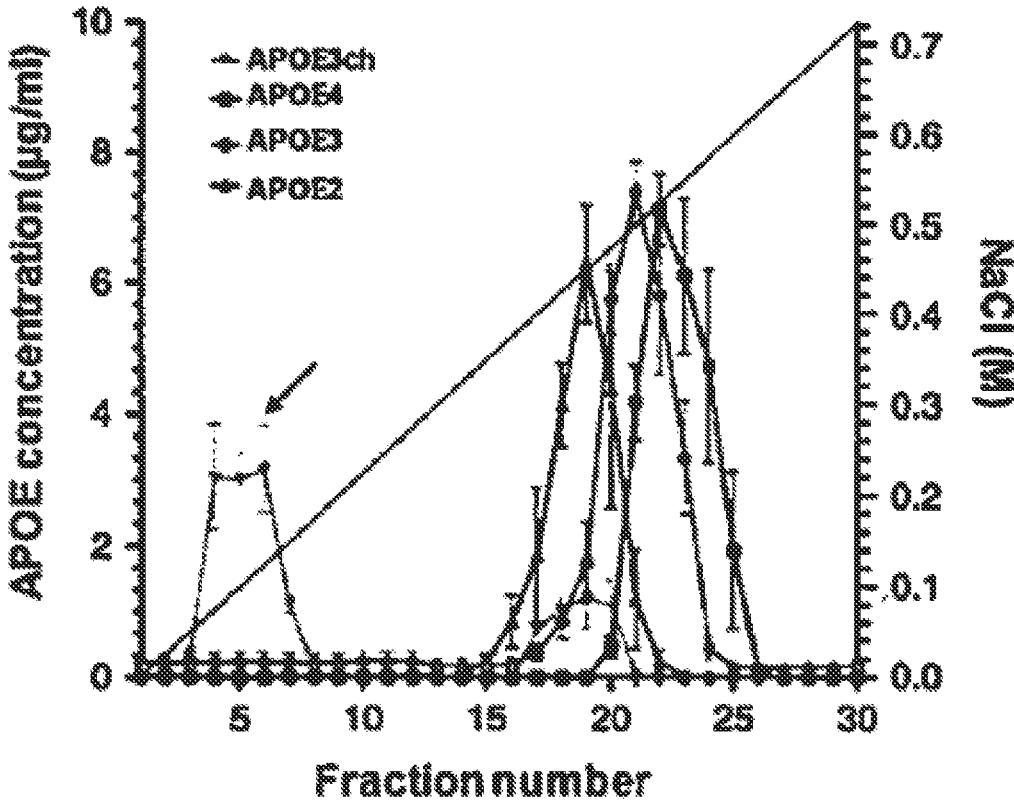

FIG. 15. The Christchurch mutation impairs heparin binding of APOE. ELISA was used to quantify differences in the NaCl elution pattern of different APOE isoforms from heparin columns. Figure taken from Arboleda-Velasquez et, al. (2019). Arrow designates the subject with the APOEChC variant.

Figures 16, 17:
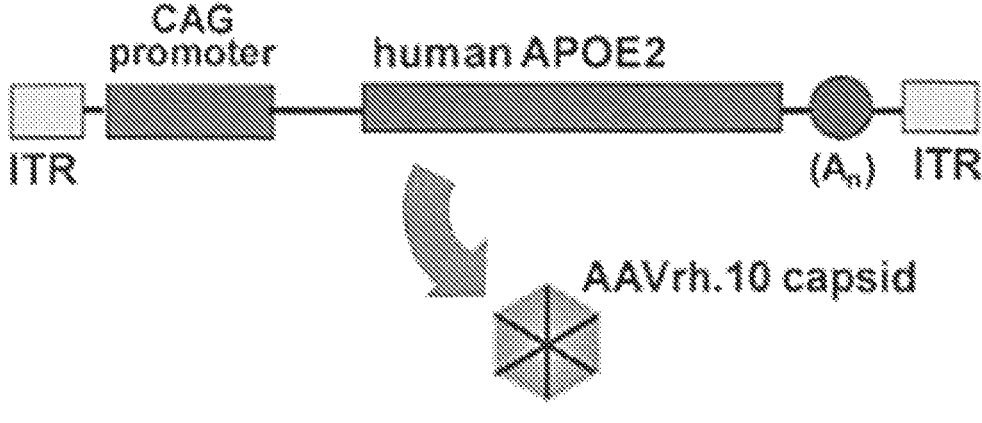

FIG. 16. AAVrh.10hAPOE2 vector. The AAVrh.10hAPOE2 vector expresses the human APOE2 transgene behind the constitutive CAG promoter, consisting of the cytomegalovirus (CMV) enhancer, chicken β actin promoter, splice donor and intron, and rabbit β-globin splice acceptor, and followed by the rabbit β-globin polyadenylation signal ($A_n$). The hAPOE2 expression cassette is flanked by the AAV2 inverted terminal repeats (ITR) and packaged into the rhesus adeno-associated viral vector serotype 10 (AAVrh.10) capsid. All APOE vectors used in this proposal are identical except for the APOE coding sequence. The AAVrh.10Null vector is identical but the expression cassette AAVrh.10hAPOE2 is replaced by a nontranslatable sequence.

FIG. 17. Using AAVrh.10hAPOE2 as an example, shown is SDS polyacrylamide gel electrophoresis which shows the 3 bands associated with the 3 AAV vector capsid proteins that align with the expected molecular weights.

FIG. 18. Assessment of the distribution of the APOE2 protein in the brain of nonhuman primates following intracisternal administration of AAVrh.10APOE2. NHPs administered AAVrh.10hAPOE2 ($5 \times 10^{13}$ gc, APOE2 transgene) assessed 8 week post-therapy. The right hemispheres were subdivided into 1 cm³ cubes and analyzed for protein APOE2 levels by ELISA. A. Human APOE2 protein in brain sections. B. CSF (10 µl/time point) was sampled from the 3 NHPs at 3 time points [pre-administration (day 0), and days 28 and 56 post-administration] and analyzed by SOS-PAGE followed by antibody detection of APOE2 by Western. See Rosenberg et al. (2018).

FIGS. 19A-19B. Resolution of amyloid pathology in the PDAPP mouse model. AAVrh.10hAPOE2 or the control AAVrh.10mCherry ($10^{10}$ gc) were administered bilaterally into the hippocampus of 9-month old PDAPP mice. Eight week post-administration, the mice were sacrificed and the hippocampus of the left hemisphere was dissected, homogenized, and sequentially extracted with RIPA (representing soluble Aβ) and 5.5 M guanidine (representing insoluble Aβ). Aβ1-42, and Aβ1-40 levels were determined by ELISA. A) Tissue levels of Aβ1-42 and B) Tissue levels of Aβ1-40 in hippocampus of PDAPP mice injected with AAVrh.10hAPOE2 or AAVrh.10mCherry. n=10-12 animals per group. Data presented as mean±SD.* p<0.05, *** p<0.001. See Zhao et al. (2016).

FIGS. 20A-20B. Dose-dependent effects of intrahippocampal delivery of APOE2 on AP levels in the hippocampus of 2.5-month old APP.PS1/TRE4 mice. AAVrh.10hAPOE2 ($0.25 \times 10^{10}$, $0.5 \times 10^{10}$ or $1 \times 10^{10}$ gc) or AAVrh.10mCherry ($1 \times 10^{10}$ gc) were injected bilaterally into the hippocampus of 2.5-month old male APP.PS1/TRE4 mice. Eight-week post-administration, the mice were sacrificed. The hippocampus of the left hemisphere was dissected, homogenized, and sequentially extracted with RIPA (representing soluble Aβ) and 5.5 M guanidine (representing insoluble Aβ). Aβ1-42 levels in each extract were determined by ELISA. A) Insoluble Aβ1-42 levels (guanidine extractable) in hippocampus. B) Soluble Aβ1-42 levels (RIPA extractable) in hippocampus. n=3-5 animals per group. Data presented as mean±SD; *p<0.05, *** p<0.001. Zhao et al. (2016).

FIGS. 21A-21B. Intrathalamic delivery of AAV9-hAPOE2 on APOE and Aβ levels in the brain in APP.PS1/TRE4 mice. Ten wk old mice were administered AAV9-hAPOE2 or AAV9-GFP by bilateral intrathalamic injection ($10^{10}$ gc) and sacrificed after 8 wk. Thalamus, hippocampus, and cerebral cortex from the left hemisphere were dissected and homogenized. A) APOE and B) Aβ1-42 levels were quantified by ELISA. Adapted from Zhao et al.

Figure 22:
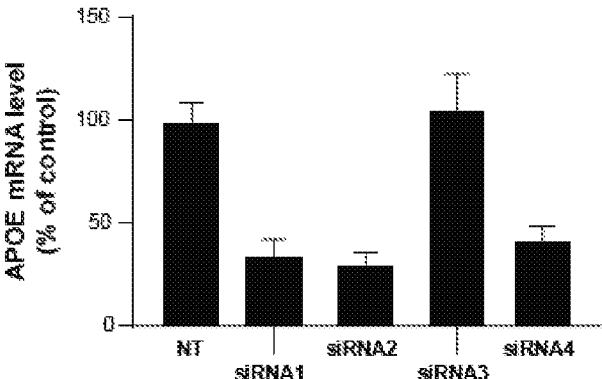

FIG. 22. Knockdown of APOE in vitro. U87 human astroglioma cells were transfected with siRNAs targeting APOE or non-targeting (NT) control (5 pmol). Cells were collected 72 hr later and endogenous APOE mRNA levels were quantified by RT-qPCR. Four different siRNAs targeting the coding sequence of APOE were generated based on a comparison of multiple siRNA design algorithms. The identified sequences were as follows: GGUG-GAGCAAGCGGUGGAGuu (SEQ ID NO:20); GGAGUUGAAGGCCUACAAAuu (SEQ ID NO:21); GGAAGACAUGCAGCGCCAGuu (SEQ ID NO:22); and GCGCGCGGAUGGAGGAGAUuu (SEQ ID NO:23).

Figure 23:
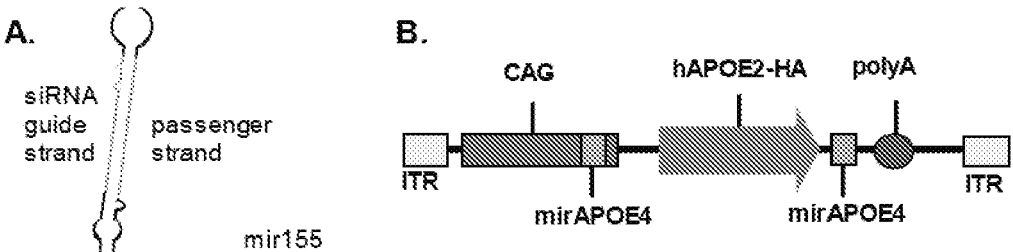

FIGS. 23A-23B. hAPOE2-mirAPOE4 expression cassette. A) Schematic of mirAPOE4. The siRNA targeting sequence (guide strand) and antisense sequence with selected mismatches (passenger strand) to facility processing are incorporated into the enhanced mir155 backbone. B) Schematic of the AAV9-hAPOE2-mirAPOE4 expression construct. The construct contains the human APOE2 coding sequence fused to a hemagglutinin tag (HA) behind the constitutive CAG promoter [cytomegalovirus (CMV) enhancer, chicken β actin promoter, splice donor and intron, and rabbit β-globin splice acceptor], and followed by the rabbit β-globin polyadenylation (polyA) signal. mirAPOE4 tandem repeats are inserted into either the CAG intron and/or between the transgene stop codon and the polyA sequence. The hAPOE2 expression cassette is flanked by the AAV2 inverted terminal repeats (ITR) and packaged into the AAV9 capsid. A miR from siRNA #2 may be employed, e.g.,

8

```
                                     (SEQ ID NO: 24)
CTGGAGGCTTGCTGAAGGCTGTATGCTGATTTGTAGGCCTTCAACTCCT

GTTTTGGCCACTGACTGACAGGAGTGAGGCCTACAAATCAGGACACAAG

GCCTGTTACTAGCACTCACATGGAACAAATGGCC;

(SEQ ID NO: 25)
CTGGAGGCTTGCTTTGGGCTGTATGCTGATTTGTAGGCCTTCAACTCCT

GTTTTGGCCACTGACTGACAGGAGTTGAAGTCACAAATCAGGACACAAG

GCCCTTTATCAGCACTCACATGGAACAAATGGCCACCGTGGGAGGATGA

CAA;
or (SEQ ID NO: 26)
CTGGAGGCTTGCTTTGGGCTGTATGCTGTTCCGATTTGTAGGCCTTCAA

GTTTTGGCCACTGACTGACTTGAAGTCACAAATCGGAACAGGACACAAG

GCCCTTTATCAGCACTCACATGGAACAAATGGCCACCGTGGGAGGATGA

CAA.
```

FIG. 24. Testing the knockdown efficiency of miRs located in the intron and polyA.

FIG. 25. Luciferase results for knock-down efficiency.

FIG. 26. Testing APOE Target Site Only Control

FIG. 27. Identifying the miRNA target site in the vector-derived APOE2 with silent nucleotide changes.

FIG. 28. Generating pAAV-miRNA-APOE-HA.

FIG. 29. In vivo studies.

FIG. 30. Luciferase expression in controls.

DETAILED DESCRIPTION

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that logical changes may be made without departing from the scope of the present invention. The following description of example embodiments is, therefore, not to be taken in a limited sense, and the scope of the present invention is defined by the appended claims.

DETAILED DESCRIPTION

Definitions

A "vector" refers to a macromolecule or association of macromolecules that comprises or associates with a polynucleotide, and which can be used to mediate delivery of the polynucleotide to a cell, either in vitro or in vivo. Illustrative vectors include, for example, plasmids, viral vectors, liposomes and other gene delivery vehicles. The polynucleotide to be delivered, sometimes referred to as a "target polynucleotide" or "transgene," may comprise a coding sequence of interest in gene therapy (such as a gene encoding a protein of therapeutic interest), a coding sequence of interest in vaccine development (such as a polynucleotide expressing a protein, polypeptide or peptide suitable for eliciting an immune response in a mammal), and/or a selectable or detectable marker.

"Transduction," "transfection," "transformation" or "transducing" as used herein, are terms referring to a process for the introduction of an exogenous polynucleotide into a host cell leading to expression of the polynucleotide, e.g., the transgene in the cell, and includes the use of recombinant virus to introduce the exogenous polynucleotide to the host cell. Transduction, transfection or transformation of a polynucleotide in a cell may be determined by methods well known to the art including, but not limited to, protein expression (including steady state levels), e.g., by ELISA, flow cytometry and Western blot, measurement of DNA and RNA by hybridization assays, e.g., Northern blots, Southern blots and gel shift mobility assays. Methods used for the introduction of the exogenous polynucleotide include well-known techniques such as viral infection or transfection, lipofection, transformation and electroporation, as well as other non-viral gene delivery techniques. The introduced polynucleotide may be stably or transiently maintained in the host cell.

"Gene delivery" refers to the introduction of an exogenous polynucleotide into a cell for gene transfer, and may encompass targeting, binding, uptake, transport, localization, replicon integration and expression.

"Gene transfer" refers to the introduction of an exogenous polynucleotide into a cell which may encompass targeting, binding, uptake, transport, localization and replicon integration, but is distinct from and does not imply subsequent expression of the gene.

"Gene expression" or "expression" refers to the process of gene transcription, translation, and post-translational modification.

An "infectious" virus or viral particle is one that comprises a polynucleotide component which it is capable of delivering into a cell for which the viral species is trophic. The term does not necessarily imply any replication capacity of the virus.

The term "polynucleotide" refers to a polymeric form of nucleotides of any length, including deoxyribonucleotides or ribonucleotides, or analogs thereof. A polynucleotide may comprise modified nucleotides, such as methylated or capped nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment described herein that is a polynucleotide encompasses both the double-stranded form and each of two complementary single-stranded forms known or predicted to make up the double-stranded form.

An "isolated" polynucleotide, e.g., plasmid, virus, polypeptide or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Isolated nucleic acid, peptide or polypeptide is present in a form or setting that is different from that in which it is found in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. The isolated nucleic acid molecule may be present in single-stranded or double-stranded form. When an isolated nucleic acid molecule is to be utilized to express a protein, the molecule will contain at a minimum the sense or coding strand (i.e., the molecule may single-stranded), but may contain both the sense and anti-sense strands (i.e., the molecule may be double-stranded). Enrichment can be measured on an absolute basis, such as weight per volume of solution, or it can be measured in relation to a second, potentially interfering substance present in the source mixture. Increasing enrichments of the embodiments of this invention are envisioned. Thus, for example, a 2-fold enrichment, 10-fold enrichment, 100-fold enrichment, or a 1000-fold enrichment.

A "transcriptional regulatory sequence" refers to a genomic region that controls the transcription of a gene or coding sequence to which it is operably linked. Transcriptional regulatory sequences of use in the present invention generally include at least one transcriptional promoter and may also include one or more enhancers and/or terminators of transcription.

"Operably linked" refers to an arrangement of two or more components, wherein the components so described are in a relationship permitting them to function in a coordinated manner. By way of illustration, a transcriptional regulatory sequence or a promoter is operably linked to a coding sequence if the TRS or promoter promotes transcription of the coding sequence. An operably linked TRS is generally joined in cis with the coding sequence, but it is not necessarily directly adjacent to it.

"Heterologous" means derived from a genotypically distinct entity from the entity to which it is compared. For example, a polynucleotide introduced by genetic engineering techniques into a different cell type is a heterologous polynucleotide (and, when expressed, can encode a heterologous polypeptide). Similarly, a transcriptional regulatory element such as a promoter that is removed from its native coding sequence and operably linked to a different coding sequence is a heterologous transcriptional regulatory element.

A "terminator" refers to a polynucleotide sequence that tends to diminish or prevent read-through transcription (i.e., it diminishes or prevent transcription originating on one side of the terminator from continuing through to the other side of the terminator). The degree to which transcription is disrupted is typically a function of the base sequence and/or the length of the terminator sequence. In particular, as is well known in numerous molecular biological systems, particular DNA sequences, generally referred to as "transcriptional termination sequences" are specific sequences that tend to disrupt read-through transcription by RNA polymerase, presumably by causing the RNA polymerase molecule to stop and/or disengage from the DNA being transcribed. Typical example of such sequence-specific terminators include polyadenylation ("polyA") sequences, e.g., SV40 polyA. In addition to or in place of such sequence-specific terminators, insertions of relatively long DNA sequences between a promoter and a coding region also tend to disrupt transcription of the coding region, generally in proportion to the length of the intervening sequence. This effect presumably arises because there is always some tendency for an RNA polymerase molecule to become disengaged from the DNA being transcribed, and increasing the length of the sequence to be traversed before reaching the coding region would generally increase the likelihood that disengagement would occur before transcription of the coding region was completed or possibly even initiated. Terminators may thus prevent transcription from only one direction ("uni-directional" terminators) or from both directions ("bi-directional" terminators), and may be comprised of sequence-specific termination sequences or sequence-non-specific terminators or both. A variety of such terminator sequences are known in the art; and illustrative uses of such sequences within the context of the present invention are provided below.

"Host cells," "cell lines," "cell cultures," "packaging cell line" and other such terms denote higher eukaryotic cells, such as mammalian cells including human cells, useful in the present invention, e.g., to produce recombinant virus or recombinant fusion polypeptide. These cells include the progeny of the original cell that was transduced. It is understood that the progeny of a single cell may not necessarily be completely identical (in morphology or in genomic complement) to the original parent cell.

"Recombinant," as applied to a polynucleotide means that the polynucleotide is the product of various combinations of cloning, restriction and/or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature.

Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter. Promoters include AAV promoters, e.g., P5, P19, P40 and AAV ITR promoters, as well as heterologous promoters.

An "expression vector" is a vector comprising a region which encodes a gene product of interest, and is used for effecting the expression of the gene product in an intended target cell. An expression vector also comprises control elements operatively linked to the encoding region to facilitate expression of the protein in the target. The combination of control elements and a gene or genes to which they are operably linked for expression is sometimes referred to as an "expression cassette," a large number of which are known and available in the art or can be readily constructed from components that are available in the art.

The terms "polypeptide" and "protein" are used interchangeably herein to refer to polymers of amino acids of any length. The terms also encompass an amino acid polymer that has been modified; for example, disulfide bond formation, glycosylation, acetylation, phosphonylation, lipidation, or conjugation with a labeling component.

The term "exogenous," when used in relation to a protein, gene, nucleic acid, or polynucleotide in a cell or organism refers to a protein, gene, nucleic acid, or polynucleotide which has been introduced into the cell or organism by artificial or natural means. An exogenous nucleic acid may be from a different organism or cell, or it may be one or more additional copies of a nucleic acid which occurs naturally within the organism or cell. By way of a non-limiting example, an exogenous nucleic acid is in a chromosomal location different from that of natural cells, or is otherwise flanked by a different nucleic acid sequence than that found in nature, e.g., an expression cassette which links a promoter from one gene to an open reading frame for a gene product from a different gene.

"Transformed" or "transgenic" is used herein to include any host cell or cell line, which has been altered or augmented by the presence of at least one recombinant DNA sequence. The host cells of the present invention are typically produced by transfection with a DNA sequence in a plasmid expression vector, as an isolated linear DNA sequence, or infection with a recombinant viral vector.

The term "sequence homology" means the proportion of base matches between two nucleic acid sequences or the proportion amino acid matches between two amino acid sequences. When sequence homology is expressed as a percentage, e.g., 50%, the percentage denotes the proportion of matches over the length of a selected sequence that is compared to some other sequence, Gaps (in either of the two sequences) are permitted to maximize matching; gap lengths of 15 bases or less are usually used, 6 bases or less e.g., with 2 bases or less. When using oligonucleotides as probes or treatments, the sequence homology between the target nucleic acid and the oligonucleotide sequence is generally not less than 17 target base matches out of 20 possible oligonucleotide base pair matches (85%); not less than 9 matches out of 10 possible base pair matches (90%), or not less than 19 matches out of 20 possible base pair matches (95%).

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less or with 2 or less. Alternatively, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. The two sequences or parts thereof are more homologous if their amino acids are greater than or equal to 50% identical when optimally aligned using the ALIGN program.

The term "corresponds to" is used herein to mean that a polynucleotide sequence is structurally related to all or a portion of a reference polynucleotide sequence, or that a polypeptide sequence is structurally related to all or a portion of a reference polypeptide sequence, e.g., they have at least 80%, 85%, 90%, 95% or more, e.g., 99% or 100%, sequence identity. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The term "sequence identity" means that two polynucleotide sequences are identical (i.e., on a nucleotide-by-nucleotide basis) over the window of comparison. The term "percentage of sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denote a characteristic of a polynucleotide sequence, wherein the polynucleotide comprises a sequence that has at least 85 percent sequence identity, e.g., at least 90 to 95 percent sequence identity, or at least 99 percent sequence identity as compared to a reference sequence over a comparison window of at least 20 nucleotide positions, frequently over a window of at least 20-50 nucleotides, wherein the percentage of sequence identity is calculated by comparing the reference sequence to the polynucleotide sequence which may include deletions or additions which total 20 percent or less of the reference sequence over the window of comparison.

"Conservative" amino acid substitutions are, for example, aspartic-glutamic as polar acidic amino acids; lysine/arginine/histidine as polar basic amino acids; leucine/isoleucine/methionine/valine/alanine/glycine/proline as non-polar or hydrophobic amino acids; serine/threonine as polar or uncharged hydrophilic amino acids. Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting polypeptide. Whether an amino acid change results in a functional polypeptide can readily be determined by assaying the specific activity of the polypeptide. Naturally occurring residues are divided into groups based on common side-chain properties: (1) hydrophobic: norleucine, met, ala, val, leu, lie; (2) neutral hydrophilic: cys, ser, thr; (3) acidic: asp, glu; (4) basic: asn, gln, his, lys, arg; (5) residues that influence chain orientation: gly, pro; and (6) aromatic: trp, tyr, phe.

The disclosure also envisions polypeptides with non-conservative substitutions. Non-conservative substitutions entail exchanging a member of one of the classes described above for another.

Rationale

Existing drugs have little effect on the underlying disease processes of AD and no preventive therapies are currently available. As there are no effective therapies for AD, an effective therapy for AD would be a major advance (Conrado et al., 2020). Worldwide, there are approximately 35 million cases of AD affecting 6% of individuals >65 years (Fane et al., 2018), and it is responsible for 1.9 million deaths/year (Collaborators GBDD, 2019; Hebert et al., 2013). In the US, there are over 122,000 deaths/year. The estimated financial burden of caring for AD patients in the US is $305 billion/year. The APOE4 allele represents 13.7% of worldwide populations and with a much higher frequency in patients with AD (Safieh et al., 2019). Inheritance of APOE4 is associated with early cognitive decline, earlier onset AD and more severe disease with earlier death (Safieh et al., 2019; Williams 2020; Raber et al., 2004). There have been many attempts at therapy for AD directed at amyloid, tau and other pathologies. While inheritance of the APOE4 allele represents the strongest genetic risk factor for the development of late-onset AD, the APOE2 allele is protective. Gene therapy to permanently deliver APOE2 while decreasing endogenous APOE4 expression could effectively convert APOE4 homozygous individuals to APOE2/4 heterozygotes with lowered APOE4 expression, substantially reducing the risk of AD development. Further APOE4 homozygous individuals could receive the ARV gene therapy according to their genotype years before the onset of symptoms. The present strategy represents the development of a strategy, capitalizing on the observation that the RPOE3ChC variant protected an individual in the PSEN1-E290A kindred who develop early-onset AD (Arboleda-Velasquez et al., 2019). AAV-mediated gene transfer of APOE3ChC and APOE2ChC may be efficacious in amyloid and/or tau pathology, and more so than AAV delivery of APOE2 alone.

Based on the knowledge that APOE4 enhances the risk for amyloid and tau-based AD pathology, it was demonstrated (Zhao et al., 2016; Shi et al., 2017; Dodart et al., 2005; Hudry et al., 2013) that CNS gene therapy with APOE2 can prevent APOE4-based AD pathology in mouse models. The primary innovation of this proposal is converting a unique clinical observation (Arboleda-Velasquez et al., 2019) into a 2nd generation, more effective gene therapy. There is extensive epidemiologic data demonstrating that the APOE genotype plays an important role in the pathogenesis of AD, with APOE2 protecting and APOE4 increasing the risk for development of AD-related pathology (Corder et al., 1994; Raber 2004; Genin et al., 2011; Sando et al., 2008). The observation that an individual in the Colombian PSEN1-E290A kindred was prevented from developing early onset AD by homozygous co-inheritance of homozygous APOE3ChC, led to APOE3ChC gene therapy based genetic modification of the CNS of APOE4 homozygotes to prevent the high risk of APOE4-driven AD-related pathology. Further, based prior studies demonstrating that gene therapy with APOE2 suppresses E4-driven amyloid-related pathology, APOE2ChC gene therapy may prevent both APOE4-driven amyloid and tau pathology and do so more effectively than APOE2 or APOE3ChC.

Exemplary APOE Nucleic Acid and Amino Acid Sequences

Apolipoprotein E (APOE) is a 299 amino acid protein involved in the metabolism of fats in the body. It is a family of proteins that binds fats and interact with the low density lipoprotein receptor (LDLR) which is important for normal processing of triglyceride rich lipoproteins. In peripheral tissues, APOE is produced by the liver and macrophages, and mediates cholesterol metabolism. In the central nervous system, APOE is produced by astrocytes and transports cholesterol to neurons via APO receptors, which are members of the LDLR family. There are three major APOE alleles, RPOE2 (Cys 112, Cys 158), APOE3 (Cys112, Arg158) and APOE4 (Arg112, Arg158).

Exemplary human APOE sequences include but are not limited to:

mkvlwaallv tflagoqakv eqavetepep elrqqtewqs gqrwelalgr fwdylrwvqt lseqvqeell ssqvtqelra lmdetmkelk aykseleeql tpvaeetrar lskelqaaqa rlgadmedvc grlvgyrgev qamigqstee lrvriashir klrkrllrda ddlqkrlavy qagaregaer glsairerlg plveqgrvra atvgslagqp lqeraqawge drarmeemg srtrdrldev keqvaevrak leeqaqqirl qaeafqarik swfeplvedm qrqwagivek vqaavgtsaa pvpsdnh (SEQ ID NO:1) as well as sequences with at least 80%, 85%, 90%, 95% or more, e.g., 99% or 100%, sequence identity thereto, where in one embodiment, APOE4 may have 31K, 46P, 79T, 130R, 163C, 292H and/or 314R, and APOE2 may have 43C, 152Q, 154C/S, 163C/P, 164Q, 172A, 176C, 242Q, 246C, 254E.

Exemplary human APOE sequences, e.g., those for silent nucleotide substitutions if they encode APOE2, include but are not limited to:

(SEQ ID NO: 2)
```
ggaacttgat gctcagagag gacaagtcat ttgcccaagg tcacacagct ggcaactggc agagccagga ttcacgccct ggcaatttga ctccagaatc ctaaccttaa cccagaagca cggcttcaag cccctggaaa ccacaatacc tgtggcagcc agggggaggt gctggaatct catttcacat gtggggaggg ggctcccctg tgctcaaggt cacaaccaaa gaggaagctg tgattaasac ccaggtccca tttgcasagc ctcgactttt agcaggtgca tcatactgtt cccacccctc ccatcccact tctgtccagc cgcctagccc cactttcttt tttttctttt tttgagacag tctccctctt gctgaggctg gagtgcagtg gcgagatctc ggctcactgt aacctccgcc tcccgggttc aagcgattct cctgcctcag cctcccaagt agctaggatt acaggcgccc gccaccacgc ctggctaact tttgtatttt tagtagagat ggggtttcac catgttggcc aggctggtct caaactcctg accttaagtg attcgcccac tgtggcctcc caaagtgctg ggattacagg cgtgagctac cgcccccagc ccctcccatc ccacttctgt ccagccccct agccctactt tctttctggg atccaggagt ccagatcccc agccccctct ccagattaca ttcatccagg cacaggaaag gacagggtca ggaaaggagg actctgggcg gcagcctcca cattcccctt ccacgcttgg cccccagaat ggaggagggt gtctggatta ctgggcgagg tgtcctccct tcctggggac tgtgggggt ggtcaaaaga cctctatgcc ccacctcctt cctccctctg ccctgctgtg cctgggcag ggggagaaca gcccacctcg tgactggggg ctggcccagc ccgccctatc cctgggggag ggggcgggac aggggggagcc ctataattgg acaagtctgg gatccttgag tcctactcag ccccagcgga ggtgaaggac gtccttcccc aggagccg
``` or (SEQ ID NO: 3)
```
ccccagcgga ggtgaaggac gtccttcccc aggagccgac tggccaatca caggcaggaa gatgaaggtt ctgtgggctg cgttgctggt cacattcctg gcaggatgcc aggccaaggt ggagcaagcg gtggagacag agccggagcc cgagctgcgc cagcagaccg agtggcagag cggccagcgc tgggaactgg cactgggtcg ctttttgggat tacctgcgct gggtgcagac actgtctgag caggtgcagg aggagctgct cagctcccaa gtcacccaag aactgagggc gctgatggac gagaccatga aggagttgaa ggcctacaaa tcggaactgg aggaacaact gacccccggta gcggaggaga cgcgggcacg gctgtccaag gagctgcaga cggcgcaggc ccggctgggc gcggacatgg aggacgtgtg cggccgcctg gtgcagtacc gcggcgaggt gcaggccatg ctcggccaga gcaccgagga gctgcgggtg cgcctcgcct cccacctgcg caagctgcgt aagcggctcc tccgcgatcc cgatgacctg cagaagcgcc tggcagtgta ccaggccggg gcccgcgagg gcgccgagcg cggcctcagc gccatccgcg agcgcctggg gcccctggtg gaacagggcc gcgtgcgggc cgccactgtg ggctccctgg ccggccagcc gctacaggag cgggcccagg cctggggcga gcggctgcgc gcgcggatgg aggagatggg cagtcggacc cgcgaccgcc tggacgaggt gaaggagcag gtggcggagg tgcgcgccaa gctggaggag caggcccagc agatacgcct gcaggccgag gccttccagg cccgcctcaa gagctggttc gagcccctgg tggaagacat gcagcgccag tgggccgggc tggtggagaa
```

-continued

```
ggtgcaggct gccgtgggca ccagcgccgc ccctgtgccc agcgacaatc actgaacgcc gaagcctgca gccatgcgac cccacgccac cccgtgcctc ctgcctccgc gcagcctgca gcgggagacc ctgtccccgc cccagccgtc ctcctggggt ggaccctagt ttaataaaga ttcaccaagt ttcacgc
``` or have (SEQ ID NO: 4)

MKVLWAALLVTFLAGCQAKVEQAVETEPEPELRQQTEWQSGQRWELALGR

FWDYLRWQTLSEQVQEELLSSQVTQELRALMDETMKELKAYKSELEEQLT

PVAEETRARLSKELQTAQARLGADMEDVCGRLVQYRGEVQAMLGQSTEEL

RVRLASHLRKLRKRLLRDPDDLQKRLAVYQAGAREGAERGLSAIRERLGP

LVEQGRVRAATVGSLAGQPLQERAQAWGERLRARMEEMGSRTRDRLDEVK

EQVAEVRAKLEEQAQQIRLQAEAFQARLKSWFEPLVEDMQRQWAGLVEKV

QAAVGTSAAPVPSDNH as well as sequences with at least 40%, 50%, 60%, 70%, 80%, 85%, 90%, 95% or more, e.g., 99% or 100%, sequence identity thereto that encode an APOE.

Other exemplary APOE sequence include (SEQ ID NO: 5)

```
mkvlwaallv tflagcqaky eqavetepep elrgqtewqs gqrwelalgr fwdylrwvqt lseqvqeell ssqvtqelra lmdetmkelk aykseleeql tpvaeetrar lskelqaaqa rlgadmedvc grlvqyrgev qamlgqstee lrvrlashlr klrkrllrda ddlqkrlavy qagaregaer glsairerlg plveqgrvra atvgslagqp lqeraqawge rlrarmeemg srtrdrldev keqvaevrak leeqaqqirl qaeafqarlk swfeplvedm qrqwaglvek vqaavgtsaa pvpsdnh;
```

(SEQ ID NO: 6)

```
mkvlwaallv tflagcqakv eqavetepep elrqqtewqs gqrwelalgr fwdylrwvqt lseqvqeell ssqvtqelra lmdetmkelk aykseleeql tpvaeetrar lskelqaaqa rlgadmedvc grlvqyrgev qamlgqstee lrvrlashlr klrkrllrda ddlqkrlavy qagaregaer glsairerlg plveqgrvra atvgslagqp lqeraqawge rlrarmeemg srtrdrldev keqvaevrak leeqaqqirl qaeafqarlk swfeplvedm qrqwaglvek vqaavgtsaa pvpsdnh;
```

(SEQ ID NO: 7)

```
mkvlwaally tflagcqakv eqavetepep elrqqtewqs gqrwelalgr fwdylrwvqt lseqvqeell ssqvtqelra lmdetmkelk aykseleeql tpvaeetrar lskelqaaqa rlgadmedvc grlvqyrgev qamlgqstee lrvrlashlr klrkrllrda ddlqkrlavy qagaregaer glsairerlg plveqgrvra atvgslagqp lqeraqawge rlrarmeemg
```

-continued

```
srtrdrldev keqvaevrak leeqaqqirl qaeafqarlk swfeplvedm qrqwaglvek vqaavgtsaa pvpsdnh.
```

For positions 112 and 158, E2 contains two cysteine residues, E3 contains a cysteine and an arginine, and E4 contains arginine residues at both sites. In one embodiment, the AAV vectors are prepared to express the Christchurch mutant in an ApoE2 or ApoE3 background. The vectors may be introduced to wild-type and disease model mice, and expression and biological measures of efficacy determined.

Gene Delivery Vectors

Gene delivery vectors within the scope of the invention include, but are not limited to, isolated nucleic acid, e.g., plasmid-based vectors which may be extrachromosomally maintained, and viral vectors, e.g., recombinant adenovirus, retrovirus, lentivirus, herpesvirus, poxvirus, papilloma virus, or adeno-associated virus, including viral and non-viral vectors which are present in liposomes, e.g., neutral or cationic liposomes, such as DOSPA/DOPE, DOGS/DOPE or DMRIE/DOPE liposomes, and/or associated with other molecules such as DNA-anti-DNA antibody-cationic lipid (DOTMA/DOPE) complexes. The gene therapy vectors may encode an APOE, RNAi, and/or an antibody or fragment thereof, as disclosed herein. Exemplary viral gene delivery vectors are described below. Gene delivery vectors may be administered via any route including, but not limited to, intracranial, intrathecal, intramuscular, buccal, rectal, intravenous or intracoronary administration, and transfer to cells may be enhanced using electroporation and/or iontophoresis, and/or scaffolding such as extracellular matrix or hydrogels, e.g., a hydrogel patch. In one embodiment, a permeation enhancer is not employed to enhance indirect delivery to the CNS.

Retroviral Vectors

Retroviral vectors exhibit several distinctive features including their ability to stably and precisely integrate into the host genome providing long-term transgene expression. These vectors can be manipulated ex vivo to eliminate infectious gene particles to minimize the risk of systemic infection and patient-to-patient transmission. Pseudotyped retroviral vectors can alter host cell tropism.

Lentiviruses

Lentiviruses are derived from a family of retroviruses that include human immunodeficiency virus and feline immunodeficiency virus. However, unlike retroviruses that only infect dividing cells, lentiviruses can infect both dividing and nondividing cells. For instance, lentiviral vectors based on human immunodeficiency virus genome are capable of efficient transduction of cardiac myocytes in vivo. Although lentiviruses have specific tropisms, pseudotyping the viral envelope with vesicular stomatitis virus yields virus with a broader range (Schnepp et al., *Meth. Mol. Med.*, 69:427 (2002)).

Adenoviral Vectors

Adenoviral vectors may be rendered replication-incompetent by deleting the early (E1A and E1B) genes responsible for viral gene expression from the genome and are stably maintained into the host cells in an extrachromosomal form. These vectors have the ability to transfect both replicating and nonreplicating cells and, in particular, these vectors have been shown to efficiently infect cardiac myocytes in vivo, e.g., after direction injection or perfusion. Adenoviral vectors have been shown to result in transient expression of therapeutic genes in vivo, peaking at 7 days and lasting approximately 4 weeks. The duration of transgene expression may be improved in systems utilizing neural specific promoters. In addition, adenoviral vectors can be produced at very high titers, allowing efficient gene transfer with small volumes of virus.

Adeno-Associated Virus Vectors

Recombinant adeno-associated viruses (rAAV) are derived from nonpathogenic parvoviruses, evoke essentially no cellular immune response, and produce transgene expression lasting months in most systems. Moreover, like adenovirus, adeno-associated virus vectors also have the capability to infect replicating and nonreplicating cells and are believed to be nonpathogenic to humans. Moreover, they appear promising for sustained cardiac gene transfer (Hoshijima et al., *Nat. Med.*, 8:864 (2002); Lynch et al., *Circ. Res.*, 80:197 (1997)).

ARV vectors include but are not limited to AAV1, AAV2, ARV5, AAV7, AAV8, AAV9 or AAVrh 10, including chimeric viruses where the AAV genome is from a different source than the capsid.

Plasmid DNA Vectors

Plasmid DNA is often referred to as "naked DNA" to indicate the absence of a more elaborate packaging system. Direct injection of plasmid DNA to myocardial cells in vivo has been accomplished. Plasmid-based vectors are relatively nonimmunogenic and nonpathogenic, with the potential to stably integrate in the cellular genome, resulting in long-term gene expression in postmitotic cells in vivo. For example, expression of secreted angiogenesis factors after muscle injection of plasmid DNA, despite relatively low levels of focal transgene expression, has demonstrated significant biologic effects in animal models and appears promising clinically (Isner, *Nature*, 415:234 (2002)). Furthermore, plasmid DNA is rapidly degraded in the blood stream; therefore, the chance of transgene expression in distant organ systems is negligible, Plasmid DNA may be delivered to cells as part of a macromolecular complex, e.g., a liposome or DNA-protein complex, e.g., see below, and delivery may be enhanced using techniques including electroporation.

Exemplary Non-Viral Formulations

Biodegradable particles comprising, e.g., isolated nucleic acid for protective APOE expression, a vector for antibody expression, or a vector for RNAi expression, may include or may be formed from biodegradable polymeric molecules which may include, but are not limited to polylactic acid (PLA), polyglycolic acid (PGA), co-polymers of PLA and PGA (i.e., polyactic-co-glycolic acid (PLGA)), captolactone (PCL), polyethylene glycol (PEG), poly(3-hydroxybutyrate), poly(p-diaxanone), polypropylene fumarate, poly (orthoesters) polyol/diketene acetals addition polymers poly-alkyl-cyano-acrylates (PAC), poly(sebacic anhydride) (PEA), poly(carboxybiscarboxyphenoxyphenoxy hexone (PCPP) poly[bis (p-carboxypheonoxy)methane]PCPM copolymers of PSA, PCPP and PCPM, poly(amino acids), poly(pseudo amino acids), polyphosphazenes, derivatives of poly[(dichloro)phosphazenes] and poly[(organo)phosphazenes], poly-hydrobutyric acid, or S-caproic acid, elastin, or gelatin. (See, e.g., Kumari et al., Colloids and Surfaces B:

Biointerfaces 75 (2010) 1-18, and U.S. Pat. Nos. 6,913,767, 6,884,435, 6,565,777 6,534,092, 6,528,087, 6,379,704, 6,309,569, 6,264,987, 6,210,707, 6,090,925, 6,022,564, 5,981,719, 5,871,747, 5,723,269, 5,603960; and 5,578,709; and U.S. Published Application No. 2007/0081972; and international Application Publication Nos. WO 2012/ 115806; and WO 2012/054425: the contents of which are incorporated herein by reference in their entireties).

The biodegradable nanoparticles may be prepared by methods known in the art. Nagavarma et al Asian J. of Pharma. And Clin. Res., Vol 5, Suppl 3, 2012, pages 16-23; Cismatu et al., Rev. Room Shim, 2010, 55(8), 433442; and International Application Publication Nos. WO 2012/ 115806; and WO 2012/054425: the contents of which are incorporated herein by reference in their entireties). Suitable methods for preparing the nanoparticles may include methods that utilize a dispersion of a preformed polymer, which may include but are not limited to solvent evaporation, nanoprecipitation, emulsification/solvent diffusion, salting out, dialysis, and supercritical fluid technology in some embodiments, the nanoparticles may be prepared by forming a double emulsion (e.g., water-in-oil-in water) and subsequently performing solvent-evaporation. The nanoparticles obtained by the disclosed methods may be subjected to further processing steps such as washing and lyophilization as desired Optionally, the nanoparticles may be combined with a preservative (e.g., trenalose).

Typically, the nano particles have a mean effective diameter of less than 1 micron, e.g., the nanoparticles have a mean effective diameter of between about 25 nm and about 500 nm, e.g., between about 50 nm and about 250 nm, about 100 nm to about 150 nm, or about 450 nm to 650 nm. The size of the particles (e.g., mean effective diameter) may be assessed by known methods in the art, which may include but are not limited to transmission electron microscopy (TEM), scanning electron microscopy (SEM), Atomic Force Microscopy (ARM), Photon Correlation Spectroscopy (PCS), Nanoparticle Surface Area Monitor (NSAM), Condensation Particle Counter (CPC), Differential Analyzer (DMA), scanning mobility Particle Sizer (SMPS), Nanoparticle Tracking Analysis (NTA), X-Ray Diffraction (XRD), Aerosol Time of Flight Mass Spectroscopy (ATFMS), and Aerosol Particle Mass Analyzer (APM).

The biodegradable nanoparticles may have a zeta-potential that facilitates uptake by target cell. Typically, the nanoparticles have a zeta-potential greeter than 0. In some embodiments, the nanoparticles have a zeta-potential between about 5 mV to about 45 mV, between about 15 mV to about 35 mV, or between about 20 mV and about 40 mV. Zeta-potential may be determined via characteristics that include electrophoretic mobility or dynamic electrophoretic mobility. Electrokinetic phenomena and electroacoustic phenomena may be utilized to calculate zeta-potential.

In one embodiment, a non-viral delivery vehicle comprises polymers including but not limited to poly(lactic-co-glycolic acid) (PLGA), polylactic acid (PLA), linear and/or branched PEI with differing molecular weights (e.g., 2, 22 and 25 kDa), dendrimers such as polyamidoamine (PAMAM) and polymethoacrylates; lipids including but not limited to cationic liposomes, cationic emulsions, DOTAP, DOTMA, DMRIE, DOSPA, distearoylphosphatidylcholine (DSPC), DOPE, or DC-cholesterol; peptide based vectors including but not limited to Poly-L-lysine or prolamine; or poly(β-amino ester), chitosan, PEI-polyethylene glycol, PEI-mannose-dextrose, DOTAP-cholesterol or RNAiMAX.

In one embodiment, the delivery vehicle is a glycopolymer-based delivery vehicle, poly(glycoamidoamine)s (PGAAs), that have the ability to complex with various polynucleotide types and form nanoparticles. These materials are created by polymerizing the methylester or lactone derivatives of various carbohydrates (D-glucarate (D), meso-galactarate (G), D-mannarate (M), and L-tartarate (T)) with a series of oligoethyleneamine monomers (containing between 1-4 ethylenamines (Liu and Reineke, 2006). A subset composed of these carbohydrates and four ethyleneamines in the polymer repeat units yielded exceptional delivery efficiency.

In one embodiment, the delivery vehicle comprises polyethyleneimine (PEI), Polyamidoamine (PAMAM), PEI-PEG, PEI-PEG-mannose, dextran-PEI, OVA conjugate, PLGA microparticles, or PLGA microparticles coated with PAMAM, or any combination thereof. The disclosed cationic polymer may include but are not limited to, polyamidoamine (PAMAM) dendrimers. Polyamidoamine dendrimers suitable for preparing the presently disposed nanoparticles may include 3rd-, 4th-, 5th-, or at least 6th-generation dendrimers.

In one embodiment, the delivery vehicle comprises a lipid, e.g., N-[1-(2,3-dioleoyloxy)propel]-N,N,N-trimethylammonium (DOTMA), 2,3-dioleyloxy-N-[2-spermine carboxamide] ethyl-N,N-dimethyl-1-propanammonium trifluoracetate (DOSPA, Lipofectamine); 1,2-dioleoyl-3-trimethylammonium-propane (DOTAP); N-[1-(2,3-dimyristloxy) propyl]; N,N-dimethyl-N-(2-hydroxyethyl) ammonium bromide (DMRIE), 3-β-[N-(N,N'-dimethylaminoethane) carbamoyl] cholesterol (DC-Chol); dioctadecyl amidoglyceryl spermine (DOGS, Transfectam); or imethyl-dioctadeclyammonium bromide (DDAB). The positively charged hydrophilic head group of cationic lipids usually consists of monoamine such as tertiary and quaternary amines, polyamine, amidinium, or guanidinium group. A series of pyridinium lipids have been developed (Zhu et al., 2008; van der Woude et al., 1997; Hies et al., 2004). In addition to pyridinium cationic lipids, other types of heterocyclic head group include imidazole, piperizine and amino acid. The main function of cationic head groups is to condense negatively charged nucleic acids by means of electrostatic interaction to slightly positively charged nanoparticles, leading to enhanced cellular uptake and endosomal escape.

Lipids having two linear fatty acid chains, such as DOTMA, DOTAP and SAINT-2, or DODAC, may be employed as a delivery vehicle, as well as tetraalkyl lipid chain surfactant, the dimer of N,N-dioleyl-N,N-dimethyl-ammonium chloride (DODAC). All the trans-orientated lipids regardless of their hydrophobic chain lengths ($C_{16:1}$, $C_{18:1}$ and $C_{20:1}$) appear to enhance the transfection efficiency compared with their cis-orientated counterparts.

The structures of cationic polymers useful as a delivery vehicle include but are not limited to linear polymers such as chitosan and linear poly(ethyleneimine), branched polymers such as branch poly(ethyleneimine) (PEI), circle-like polymers such as cyclodextrin, network (crosslinked) type polymers such as crosslinked poly(amino acid) (PRA), and dendrimers. Dendrimers consist of a central core molecule, from which several highly branched arms 'grow' to form a tree-like structure with a manner of symmetry or asymmetry. Examples of dendrimers include polyamidoamine (PAMAM) and polypropylenimine (PPI) dendrimers.

DOPE and cholesterol are commonly used neutral co-lipids for preparing cationic liposomes. Branched PEI-cholesterol water-soluble lipopolymer conjugates self-assemble into cationic micelles. Pluronic (poloxamer), a non-ionic polymer and SP1017, which is the combination of Pluronics L61 and F127, may also be used.

In one embodiment, PLGA particles are employed to increase the encapsulation frequency although complex formation with PLL may also increase the encapsulation efficiency. Other cationic materials, for example, PEI, DOTMA, DC-Chol, or CTAB, may be used to make nanospheres.

In one embodiment, complexes are embedded in or applied to a material including but not limited to hydrogels of poloxamers, polyacrylamide, poly(2-hydroxyethyl methacrylate), carboxyvinyl-polymers (e.g., Carbopol 934, Goodrich Chemical Co.), cellulose derivatives, e.g., methylcellulose, cellulose acetate and hydroxypropyl cellulose, polyvinyl pyrrolidone or polyvinyl alcohols, or combinations thereof.

In some embodiments, a biocompatible polymeric material is derived from a biodegradable polymeric such as collagen, e.g., hydroxylated collagen, fibrin, polylactic-polyglycolic acid, or a polyanhydride. Other examples include, without limitation, any biocompatible polymer, whether hydrophilic, hydrophobic, or amphiphilic, such as ethylene vinyl acetate copolymer (EVA), polymethyl methacrylate, polyamides, polycarbonates, polyesters, polyethylene, polypropylenes, polystyrenes, polyvinyl chloride, polytetrafluoroethylene, N-isopropylacrylamide copolymers, poly(ethylene oxide)/poly(propylene oxide) block copolymers, poly(ethylene glycol)/poly(D,L-lactide-co-glycolide) block copolymers, polyglycolide, polylactides (PLLA or PDLA), poly(caprolactone) (PCL), or poly(dioxanone) (PPS).

In another embodiment, the biocompatible material includes polyethyleneterephalate, polytetrafluoroethylene, copolymer of polyethylene oxide and polypropylene oxide, a combination of polyglycolic acid and polyhydroxyalkanoate, gelatin, alginate, poly-3-hydroxybutyrate, poly-4-hydroxybutyrate, and polyhydroxyoctanoate, and polyacryanitrilepolyvinylchlorides.

In one embodiment, the following polymers may be employed, e.g., natural polymers such as starch, chitin, glycosaminoglycans, e.g., hyaluronic acid, dermatan sulfate and chrondrotin sulfate, and microbial polyesters, e.g., hydroxyalkanoates such as hydroxyvalerate and hydroxybutyrate copolymers, and synthetic polymers, e.g., poly (orthoesters) and polyanhydrides, and including homo and copolymers of glycolide and lactides (e.g., poly(L-lactide, poly(L-lactide-co-D,L-lactide), poly(L-lactide-co-glycolide, polyglycolide and poly(D,L-lactide), pol(D,L-lactide-coglycolide), poly(lactic acid colysine) and polycaprolactone.

In one embodiment, the biocompatible materials derived from isolated extracellular matrix (ECM). ECM may be isolated from endothelial layers of various cell populations, tissues and/or organs, e.g., any organ or tissue source including the dermis of the skin, liver, alimentary, respiratory, intestinal, urinary or genital tracks of a warm blooded vertebrate. ECM employed in the invention may be from a combination of sources. Isolated ECM may be prepared as a sheet, in particulate form, gel form and the like.

The biocompatible scaffold polymer may comprise silk, elastin, chitin, chitosan, poly(d-hydroxy acid), poly(anhydrides), or poly(orthoesters). More particularly, the biocompatible polymer may be formed polyethylene glycol, poly(lactic acid), poly(glycolic acid), copolymers of lactic and glycolic acid, copolymers of lactic and glycolic acid with polyethylene glycol, poly(E-caprolactone), poly(3-hydroxybutyrate), polyp-dioxanone), polypropylene fumarate, poly (orthoesters), polyol/diketene acetals addition polymers, poly(sebacic anhydride) (PSA), poly(carboxybiscarboxy-phenoxyphenoxy hexane (PCPP) poly[bis (p-carboxypheon-oxy) methane] (PCPM), copolymers of SA, CPP and CPM, poly(amino acids), poly(pseudo amino acids), polyphospha-zenes, derivatives of poly[(dichloro)phosphazenes] or poly [(organo) phosphazenes], poly-hydroxybutyric acid, or S-caproic acid, polylactide-co-glycolide, polylactic acid, polyethylene glycol, cellulose, oxidized cellulose, alginate, gelatin or derivatives thereof.

Thus, the polymer may be formed of any of a wide range of materials including polymers, including naturally occur-ring polymers, synthetic polymers, or a combination thereof. In one embodiment, the scaffold comprises biodegradable polymers. In one embodiment, a naturally occurring biode-gradable polymer may be modified to provide for a synthetic biodegradable polymer derived from the naturally occurring polymer. In one embodiment, the polymer is a poly(lactic acid) ("PLA") or poly(lactic-co-glycolic acid) ("PLGA"). In one embodiment, the scaffold polymer includes but is not limited to alginate, chitosan, poly(2-hydroxyethylmethacry-late), xyloglucan, co-polymers of 2-methacryloyloxyethyl phosphorylcholine, polyvinyl alcohol), silicone, hydropho-bic polyesters and hydrophilic polyester, poly(lactide-co-glycolide), N-isoproylacrylamide copolymers, poly(ethyl-ene oxide)/poly(propylene oxide), polylactic acid, poly (orthoesters), polyanhydrides, polyurethanes, copolymers of 2-hydroxyethylmethacrylate and sodium methacrylate, phosphorylcholine, cyclodextrins, polysulfone and polyvi-nylpyrrolidine, starch, poly-D,L-lactic acid-para-dioxanone-polyethylene glycol block copolymer, polypropylene, poly (ethylene terephthalate), poly(tetrafluoroethylene), poly-epsilon-caprolactone, or crosslinked chitosan hydrogels.

Alternatively, the nucleic acids or vectors, can be admin-istered in dosages of at least about 0.0001 mg/kg to about 1 mg/kg, of at least about 0.001 mg/kg to about 0.5 mg/kg, at least about 0.01 mg/kg to about 0.25 mg/kg or at least about 0.01 mg/kg to about 0.25 mg/kg of body weight, although other dosages may provide beneficial results.

Alternatively, the nucleic acids or vectors, can be admin-istered in dosages of at least about 0.0001 mg/kg to about 1 mg/kg, of at least about 0,001 mg/kg to about 0.5 mg/kg, at least about 0.01 mg/kg to about 0.25 mg/kg or at least about 0.01 mg/kg to about 0.25 mg/kg of body weight, although other dosages may provide beneficial results.

Pharmaceutical Compositions

The invention provides a composition comprising, con-sisting essentially of, or consisting of the above-described gene transfer vector(s) and a pharmaceutically acceptable (e.g., physiologically acceptable) carrier. When the compo-sition consists essentially of the gene transfer vector and a pharmaceutically acceptable carrier, additional components can be included that do not materially affect the composition (e.g., adjuvants, buffers, stabilizers, anti-inflammatory agents, solubilizers, preservatives, etc.). When the compo-sition consists of the inventive gene transfer vector and the pharmaceutically acceptable carrier, the composition does not comprise any additional components. Any suitable car-rier can be used within the context of the invention, and such carriers are well known in the art. The choice of carrier will be determined, in part, by the particular site to which the composition may be administered and the particular method used to administer the composition. The composition optionally can be sterile with the exception of the gene transfer vector described herein. The composition can be frozen or lyophilized for storage and reconstituted in a suitable sterile carrier prior to use. The compositions can be generated in accordance with conventional techniques described in, e.g., *Remington: The Science and Practice of Pharmacy,* 21st *Edition,* Lippincott Williams & Wilkins, Philadelphia, PA (2001).

Suitable formulations for the composition include aque-ous and non-aqueous solutions, isotonic sterile solutions, which can contain anti-oxidants, buffers, and bacteriostats, and aqueous and non-aqueous sterile suspensions that can include suspending agents, solubilizers, thickening agents, stabilizers, and preservatives. The formulations can be pre-sented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets of the kind previously described. In one embodiment, the carrier is a buffered saline solution. In one embodiment, the inventive gene transfer vector is administered in a composition for-mulated to protect the gene transfer vector from damage prior to administration. For example, the composition can be formulated to reduce loss of the gene transfer vector on devices used to prepare, store, or administer the gene transfer vector, such as glassware, syringes, or needles. The composition can be formulated to decrease the light sensi-tivity and/or temperature sensitivity of the gene transfer vector. To this end, the composition may comprise a phar-maceutically acceptable liquid carrier, such as, for example, those described above, and a stabilizing agent selected from the group consisting of polysorbate 80, L-arginine, polyvi-nylpyrrolidone, trehalose, and combinations thereof. Use of such a composition will extend the shelf life of the gene transfer vector, facilitate administration, and increase the efficiency of the inventive method. Formulations for gene transfer vector-containing compositions are further described in, for example, Wright et al., Curr. Opin. Drug Discov. Devel., 6(2): 174-178 (2003) and Wright et al., *Molecular Therapy,* 12: 171-178 (2005))

The composition also can be formulated to enhance transduction efficiency. In addition, one of ordinary skill in the art will appreciate that the inventive gene transfer vector can be present in a composition with other therapeutic or biologically-active agents. For example, factors that control inflammation, such as ibuprofen or steroids, can be part of the composition to reduce swelling and inflammation asso-ciated with in vivo administration of the gene transfer vector. Immune system stimulators or adjuvants, e.g., interleukins, lipopolysaccharide, and double-stranded RNA. Antibiotics, i.e., microbicides and fungicides, can be present to treat existing infection and/or reduce the risk of future infection, such as infection associated with gene transfer procedures.

Injectable depot forms are made by forming microencap-sule matrices of the subject compounds in biodegradable polymers such as polylactide-polyglycolide. Depending on the ratio of drug to polymer, and the nature of the particular polymer employed, the rate of drug release can be con-trolled. Examples of other biodegradable polymers include poly(orthoesters) and poly(anhydrides). Depot injectable formulations are also prepared by entrapping the drug in liposomes or microemulsions which are compatible with body tissue.

In certain embodiments, a formulation comprises a bio-compatible polymer selected from the group consisting of polyamides, polycarbonates, polyalkylenes, polymers of acrylic and methacrylic esters, polyvinyl polymers, polygly-colides, polysiloxanes, polyurethanes and co-polymers thereof, celluloses, polypropylene, polyethylenes, polysty-rene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

The composition can be administered in or on a device that allows controlled or sustained release, such as a sponge, biocompatible meshwork, mechanical reservoir, or mechanical implant. Implants (see, e.g., U.S. Pat. No. 5,443, 505), devices (see, e.g., U.S. Pat. No. 4,863,457), such as an implantable device, e.g., a mechanical reservoir or an implant or a device comprised of a polymeric composition, are particularly useful for administration of the inventive gene transfer vector. The composition also can be administered in the form of sustained-release formulations (see, e.g., U.S. Pat. No. 5,378,475) comprising, for example, gel foam, hyaluronic acid, gelatin, chondroitin sulfate, a polyphosphoester, such as bis-2-hydroxyethyl-terephthalate (BHET), and/or a polylactic-glycolic acid.

The dose of the gene transfer vector in the composition administered to the mammal will depend on a number of factors, including the size (mass) of the mammal, the extent of any side-effects, the particular route of administration, and the like. In one embodiment, the inventive method comprises administering a "therapeutically effective amount" of the composition comprising the inventive gene transfer vector described herein. A "therapeutically effective amount" refers to an amount effective, at dosages and for periods of time as necessary, to achieve a desired therapeutic result. The therapeutically effective amount may vary according to factors such as the extent of the disease or disorder, age, sex, and weight of the individual, and the ability of the gene transfer vector to elicit a desired response in the individual. The dose of gene transfer vector in the composition to achieve a particular therapeutic effect typically is administered in units of vector genome copies per cell (gc/cell) or vector genome copies/per kilogram of body weight (gc/kg). One of ordinary skill in the art can readily determine err appropriate gene transfer vector dose range to treat a patient having a particular disease or disorder, based on these and other factors that are well known in the art. The therapeutically effective amount may be between $1 \times 10^{10}$ genome copies to $1 \times 10^{13}$ genome copies. The therapeutically effective amount may be between $1 \times 10^{11}$ genome copies to $1 \times 10^{14}$ genome copies. The therapeutically effective amount may be between $1 \times 10^{7}$ genome copies to $1 \times 10^{10}$ genome copies. The therapeutically effective amount may be between $1 \times 10^{14}$ genome copies to $1 \times 10^{11}$ genome copies. Assuming a 70 kg human, the dose ranges may be from $1.4 \times 10^{8}$ gc/kg to $1.4 \times 10^{11}$ gc/kg, $1.4 \times 10^{9}$ gc/kg to $1.4 \times 10^{12}$ gc/kg, $1.4 \times 10^{10}$ gc/kg to $1.4 \times 10^{18}$ gc/kg, or $1.4 \times 10^{11}$ gc/kg to $1.4 \times 10^{14}$ gc/kg.

In one embodiment, the composition is administered once to the mammal. It is believed that a single administration of the composition may result in persistent expression in the mammal with minimal side effects. However, in certain cases, it may be appropriate to administer the composition multiple times during a therapeutic period to ensure sufficient exposure of cells to the composition. For example, the composition may be administered to the mammal two or more times (e.g., 2, 3, 4, 5, 6, 6, 8, 9, or 10 or more times) during a therapeutic period.

The present disclosure provides pharmaceutically acceptable compositions which comprise a therapeutically-effective amount of gene transfer vector comprising a nucleic acid sequence as described above.

Routes of Administration, Dosages and Dosage Forms

Administration of, for example, the gene delivery vectors in accordance with the present invention, may be continuous or intermittent, depending, for example, upon the recipient's physiological condition, and other factors known to skilled practitioners. The administration of the gene delivery vector (s) may be essentially continuous over a preselected period of time or may be in a series of spaced doses. Both local administration, e.g., intracranial, intranasal tar intrathecal, and systemic administration, e.g., using viruses that cross the blood-brain barrier, are contemplated. Any route of administration may be employed, e.g., intravenous, intranasal or intrabronchial, direct administration to the lung and intrapleural. In one embodiment, compositions may be delivered to the pleura.

One or more suitable unit dosage forms comprising the gene delivery vector(s), which may optionally be formulated for sustained release, can be administered by a variety of routes including intracranial, intrathecal, or intranasal, or other means to deliver to the CNS, or oral, or parenteral, including by rectal, buccal, vaginal and sublingual, transdermal, subcutaneous, intravenous, intramuscular, intraperitoneal, intrathoracic, or intrapulmonary routes. The formulations may, where appropriate, be conveniently presented in discrete unit dosage forms and may be prepared by any of the methods well known to pharmacy. Such methods may include the step of bringing into association the vector with liquid carriers, solid matrices, semi-solid carriers, finely divided solid carriers or combinations thereof, and then, if necessary, introducing or shaping the product into the desired delivery system.

The amount of gene delivery vector(s) administered to achieve a particular outcome will vary depending on various factors including, but not limited to, the genes and promoters chosen, the condition, patient specific parameters, e.g., height, weight and age, and whether prevention or treatment, is to be achieved.

Vectors of the invention may conveniently be provided in the form of formulations suitable for administration, e.g., into the brain. A suitable administration format may best be determined by a medical practitioner for each patient individually, according to standard procedures. Suitable pharmaceutically acceptable carriers and their formulation are described in standard formulations treatises, e.g., Remington's Pharmaceuticals Sciences. By "pharmaceutically acceptable" it is meant a carrier, diluent, excipient, and/or salt that is compatible with the other ingredients of the formulation, and not deleterious to the recipient thereof.

Vectors of the invention may be formulated in solution at neutral pH, for example, about pH 6.5 about pH 8.5, or from about pH 7 to 8, with an excipient to bring the solution to about isotonicity, for example, 4.5% mannitol or 0.9% sodium chloride, pH buffered with art-known buffer solutions, such as sodium phosphate, that are generally regarded as safe, together with an accepted preservative such as metacresol 0.1% to 0.75%, or from 0.15% to 0.4% metacresol. Obtaining a desired isotonicity can be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is useful for buffers containing sodium ions. If desired, solutions of the above compositions can also be prepared to enhance shelf life and stability. Therapeutically useful compositions of the invention can be prepared by mixing the ingredients following generally accepted procedures. For example, the selected components can be mixed to produce a concentrated mixture which may then be adjusted to the final concentration and viscosity by the addition of water and/or a buffer to control pH or an additional solute to control tonicity.

The vectors can be provided in a dosage form containing an amount of a vector effective in one or multiple doses. For viral vectors, the effective dose may be in the range of at least about $10^7$ viral particles, e.g., about $10^9$ viral particles, or about $10^{11}$ viral particles. The number of viral particles added may be up to $10^{14}$. For example, when a viral expression vector is employed, about $10^8$ to about $10^{60}$ gc of viral vector can be administered as nucleic acid or as a packaged virion. In some embodiments, about $10^9$ to about $10^{15}$ copies of viral vector, e.g., per 0.5 to 10 mL, can be administered as nucleic acid or as a packaged virion. Alternatively, the nucleic acids or vectors, can be administered in dosages of at least about 0.0001 mg/kg to about 1 mg/kg, of at least about 0.001 mg/kg to about 0.5 mg/kg, at least about 0.01 mg/kg to about 0.25 mg/kg or at least about 0.01 mg/kg to about 025 mg/kg of body weight, although other dosages may provide beneficial results. The amount administered will vary depending on various factors including, but not limited to, the nucleic acid or vector chosen for administration, the disease, the weight, the physical condition, the health, and/or the age of the mammal. Such factors can be readily determined by the clinician employing animal models or other test systems that are available in the art. As noted, the exact dose to be administered is determined by the attending clinician, but may be in 1 mL phosphate buffered saline. For delivery of plasmid DNA alone, or plasmid DNA in a complex with other macromolecules, the amount of DNA to be administered will be an amount which results in a beneficial effect to the recipient. For example, from 0.0001 to 1 mg or more, e.g., up to 1 g, in individual or divided doses, e.g., from 0,001 to 0.5 mg, or 0.01 to 0.1 mg, of DNA can be administered.

For example, when a viral expression vector is employed, about $10^8$ to about $10^{89}$ gc of viral vector can be administered as nucleic acid or as a packaged virion. In some embodiments, about $10^9$ to about $10^{15}$ copies of viral vector, e.g., per 0.5 to 10 mL, can be administered as nucleic acid or as a packaged virion. Alternatively, the nucleic acids or vectors, can be administered in dosages of at least about 0.0001 mg/kg to about 1 mg/kg, of at least about 0.001 mg/kg to about 0.5 mg/kg, at least about 0.01 mg/kg to about 0.25 mg/kg or at least about 0.01 mg/kg to about 0.25 mg/kg of body weight, although other dosages may provide beneficial results.

In one embodiment, administration may be by intracranial, intraventricular, intracisternal, lumbar, intrahepatic, intratracheal or intrabronchial injection or infusion using an appropriate catheter or needle. A variety of catheters may be used to achieve delivery, as is known in the art. For example, a variety of general purpose catheters, as well as modified catheters, suitable for use in the present invention are available from commercial suppliers. Also, where delivery is achieved by injection directly into a specific region of the brain or lung, a number of approaches can be used to introduce a catheter into that region, as is known in the art.

By way of illustration, liposomes and other lipid-containing gene delivery complexes can be used to deliver one or more transgenes. The principles of the preparation and use of such complexes for gene delivery have been described in the art (see, e.g., Ledley, (1995); Miller et al., (1995); Chonn et al., (1995); Schofield et al., (1995); Brigham et al., ('1993)).

Pharmaceutical formulations containing the gene delivery vectors can be prepared by procedures known in the art using well known and readily available ingredients. For example, the agent can be formulated with common excipients, diluents, or carriers, and formed into tablets, capsules, suspensions, powders, and the like. The vectors of the invention can also be formulated as elixirs or solutions appropriate for parenteral administration, for instance, by intramuscular, subcutaneous or intravenous routes.

The pharmaceutical formulations of the vectors can also take the form of an aqueous or anhydrous solution, e.g., a lyophilized formulation, or dispersion, or alternatively the form of an emulsion or suspension.

In one embodiment, the vectors may be formulated for administration, e.g., by injection, for example, bolus injection or continuous infusion via a catheter, and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable vehicles and adjuvants which are well known in the prior art. It is possible, for example, to prepare solutions using one or more organic solvent(s) that is/are acceptable from the physiological standpoint.

For administration to the upper (nasal) or lower respiratory tract by inhalation, the vector is conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g., gelatine or blister packs from which the powder may be administered with the aid of an inhalator, insufflator or a metered-dose inhaler.

For intra-nasal administration, the vector may be administered via nose drops, a liquid spray, such as via a plastic bottle atomizer or metered-dose inhaler. Typical of atomizers are the Mistometer (Wintrop) and the Medihaler (Riker).

The local delivery of the vectors can also be by a variety of techniques which administer the vector at or near the site of disease, e.g., using a catheter or needle Examples of site-specific or targeted local delivery techniques are not intended to be limiting but to be illustrative of the techniques available. Examples include local delivery catheters, such as an infusion or indwelling catheter, e.g., a needle infusion catheter, shunts and stents or other implantable devices, site specific carriers, direct injection, or direct applications.

The formulations and compositions described herein may also contain other ingredients such as antimicrobial agents or preservatives.

Subjects

The subject may be any animal, including a human. human and non-human animals. Non-human animals includes all vertebrates, e.g., mammals and non-mammals, such as non-human primates, sheep, dogs, cats, cows, horses, chickens, amphibians, and reptiles, although mammals, such as non-human primates, sheep, dogs, cats, cows and horses may be the subject. The subject may also be livestock such as, cattle, swine, sheep, poultry, and horses, or pets, such as dogs and cats.

In one embodiment, subjects include human subjects. The subject is generally diagnosed with the condition by skilled artisans, such as a medical practitioner.

The methods of the invention described herein can be employed for subjects of any species, gender, age, ethnic population, or genotype. Accordingly, the term subject includes males and females, and it includes elderly, elderly-to-adult transition age subjects adults, adult-to-pre-adult transition age subjects, and pre-adults, including adolescents, childrens, and infants.

Examples of human ethnic populations include Caucasians, Asians, Hispanics, Africans, African Americans, Native Americans, Semites, and Pacific Islanders. The methods of the invention may be more appropriate for some ethnic populations such as Caucasians, especially northern European populations, as well as Asian populations.

The term subject also includes subjects of any genotype or phenotype as long as they are in need of the invention, as described above. In addition, the subject can have the genotype or phenotype for any hair color, eye color, skin color or any combination thereof.

The term subject includes a subject of any body height, body weight, or any organ or body part size or shape.

EXEMPLARY EMBODIMENTS

In one embodiment, a gene therapy vector is provided comprising an expression cassette coding for a mammalian apolipoprotein E that has a residue other than arginine at at least one of positions 112, 136, or 158, or coding for an antibody or antigen binding fragment thereof that specifically binds APOE4, such as an antibody that has the binding specificity or is derived from 9D11, 4E4 (binds to residues between 100 and 150), 5B5, E29, 1343A (Arboleda-Velasquez et al., 2019), or one disclosed in U.S. Pat. No. 8,741,298, the disclosures of which are incorporated by reference herein, or one that binds heparan sulfate, e.g., heparan sulfate proteoglycans (HPSGs). In one embodiment, the mammalian apolipoprotein E is not APOE2, APOE3, or APOE4 but rather is a modified APOE that is protective, e.g., decreases or delays cognitive impairment or deterioration, when exogenously expressed in a mammal, or may have reduced binding to HSPGs. In one embodiment, the apolipoprotein E in the vector is a human apolipoprotein E, e.g., modified as described herein. In one embodiment, the residue in the APOE in the vector other than arginine is serine, threonine, asparagine, cysteine, or glutamine. In one embodiment, position 112 in the APOE in the vector is a cysteine. In one embodiment, position 136 in the APOE in the vector i a serine. In one embodiment, position 158 in the APOE in the vector is an arginine or a cysteine. In one embodiment, two of positions 112, 136 or 158 in APOE in the vector have an arginine. In one embodiment, position 112 in the APOE in the vectors does not have an arginine. In one embodiment, position 158 in APOE in the vector does not have an arginine. In one embodiment, the gene therapy is a viral gene therapy vector, e.g., an adenovirus, adeno-associated virus (AAV), retrovirus or lentivirus vector. In one embodiment, the viral gene therapy vector is a rAAV vector. In one embodiment, the AAV vector has an AAVrh.10, AAV8, AAV9, AAV5, AAVhu.37, AAVhu.20, AAVhu.43, AAVhu.8, AAVhu.2, or AAV7 capsid. In one embodiment, the AAV vector is AAV2, AAV5, AAV7, AAV8, AAV9 or AAVrh.10. The vector may be present in a pharmaceutical composition. In one embodiment, the amount of the viral vector in the composition is about $1 \times 10^{11}$ to about $1 \times 10^{16}$ genome copies.

The vector may be introduced to cells in vitro or in vivo. In one embodiment, a method to prevent, inhibit or treat Alzheimer's disease in a mammal includes administering to the mammal an effective amount of the gene therapy vector. In one embodiment, a method to prevent, inhibit or treat a disease associated with APOE4 expression in a mammal includes administering to the mammal an effective amount of the gene therapy vector. In one embodiment, a method to prevent, inhibit or treat a lipid disorder in a mammal includes administering to the mammal an effective amount the gene therapy vector. In one embodiment, the mammal is a E2/E4 heterozygote. In one embodiment, the mammal is a E4/E4 homozygote. In one embodiment, the mammal is a E2/E2 homozygote. In one embodiment, the mammal is a E3/E3 homozygote. In one embodiment, the mammal is a E3/E4 heterozygote. In one embodiment, the mammal is a E2/E3 heterozygote. In one embodiment, the mammal is a human. In one embodiment, the vector is systemically administered. In one embodiment, the vector is injected. In one embodiment, the vector is administered to the central nervous system. In one embodiment, the vector is administered to the brain. In one embodiment, the vector encodes an apolipoprotein E having 0112, 5136 and 8158 or having 0112, 5136 and 0158.

In one embodiment, a gene therapy vector comprising a promoter operably linked to a nucleic acid sequence comprising an open reading frame encoding APOE that is not APOE2, APOE3, or APOE4 but is modified and is protective, and a 3' untranslated region (3' UTR), and a nucleotide sequence having RNAi sequences corresponding to APOE4 for inhibition of APOE4 mRNA. In one embodiment, the vector comprises the nucleotide sequence. In one embodiment, the nucleotide sequence is 5' or 3' to the open reading frame. In one embodiment, the nucleotide sequence is 5' and 3' to the open reading frame. In one embodiment, the nucleotide sequence is on a different vector. In one embodiment, the vector is a viral vector. In one embodiment, the viral vector is an AAV, adenovirus, lentivirus, herpesvirus or retrovirus vector. In one embodiment, the AAV is AAV5, AAV9 or AAVrh10. In one embodiment, the nucleotide sequence is linked to a second promoter. In one embodiment, the second promoter is a Fall promoter. In one embodiment, the RNAi comprises miRNA including a plurality of miRNA sequences. In one embodiment, the RNAi comprises siRNA including a plurality of siRNA sequences. In one embodiment, the open reading frame comprises a plurality of silent nucleotide substitutions. In one embodiment, the vector has at least 5%, 10%, 20%, 30%, 40%, 50%, 60%, 70%, 80% or 90% of the codons have a silent nucleotide substitution. In one embodiment, the open reading frame further comprises a peptide tag, e.g., a HA, histidine tag, AviTag, maltose binding tag, Strep-tag, FLAG-tag, V5-tag, Myc-tag, Spot-tag, T7 tag, or NE-tag. In one embodiment, the vector is in a host cell, e.g., in a host organism such as a mammal, or a non-human primate or a human. The host mammal may be administered the vector in an amount effective to, for example, prevent, inhibit or treat Alzheimer's disease in a mammal, or prevent, inhibit or treat a disease associated with APOE4 expression in a mammal. In one embodiment, the vector and/or the nucleotide sequence is systemically administered. In one embodiment, the vector and/or the nucleotide sequence is orally administered. In one embodiment, the vector and/or the nucleotide sequence is intravenously administered.

The invention will be further described by the following non-limiting examples.

Example 1

Overview

The pathogenesis of Alzheimer's disease (AD) is complex, characterized by central nervous system (CNS) accumulation of amyloid-beta (Aβ), and amyloid plaques, abnormal phosphorylation of tau, tau tangles, inflammation and progressive loss of neurons, resulting in progressive cognitive decline1. Genetics play a major role in the risk for these pathogenic processes (DeTure & Dickson, 2019; Holtzman et al., 2012; Safieh et al., 2019; Fernandez et al, 2019). Early-onset autosomal dominant AD is caused by mutations in amyloid protein precursor (APP) and presenilin (PSEN) 1 and 2 (Campion et al., 1999; Carmona et al., 2018), genes that affect APP processing, altering production of Aβ peptides, resulting in aggregation and plaque formation (Carmona et al., 2018; Dai et al., 2018). The major genetic factors for sporadic late-onset AD are variants of apolipoprotein E (APOE), a lipid transport protein (Tzioras et al., 2019; Wolters et al., 2019). APOE has 3 common isoforrns, the common ε3 isoform is associated with an average risk for AD, ε4 increases risk 15-20-fold while ε2 decreases risk 66 to 99% lower than c3 and FA, respectively (Wolters et al., 2019; Corder et al., 1994; Naj et al., 2011; Reiman et al., 2020). At the biologic level, the APOE genotype (ε4>ε3>ε2) predicts timing and amount of brain amyloid, p-tau and tau tangles in humans and AD mouse models (Tzioras et al., 2019; Shi et al., 2017; Abner et al., 2018). The differences in E2 and E4 are dictated by amino acids 112 and 158; APOE2 (C112 0158) conveys low risk and APOE4 (R112 8158) high risk (Corder et al., 1994; Reiman et al., 2020; Corder et al., 1993). Within this 112-158 "Alzheimer's risk region" is coding for the LDL receptor and binding to heparan proteoglycans (Mahley et al., 1999).

Since APOE4 conveys high risk and APOE2 low risk, to develop a gene therapy to prevent/treat the development of AD-related pathology in APOE4 homozygotes with AAVrh.10hAPOE2, a serotype rh.10 adeno-associated virus (AAV) gene transfer vector coding for human APOE2 was prepared. CNS administration of AAVrh.10hAPOE2 prevented APOE4-associated Aβ and amyloid burden in mouse models (Zhao et al., 2016), supporting the concept that APOE4-associated risk for AD might be mitigated using APOE2 gene therapy to convert the APOE4 homozygote brain to an APOE2-APOE4 heterozygote state (Zhao et al., 2016).

The importance of the APOE 112-158 region in mediating AD risk was highlighted by the report of a female carrier of the PSEN1 E280 mutation but also homozygote for APOE3ChC, the Christchurch R1365 APOE3 variant (Arboleda-Velasquez et al., 2019). The dominant PSEN1-E290A gene defines a Colombian family of >1,200 individuals all with early onset CNS Aβ and amyloid accumulation; heterozygotes develop dementia in their mid-forties (Lopera et al., 1997). Strikingly, the female who co-inherited APOE3ChC and PSEN1-E290A was in good cognitive condition at age 70, well past the age when the kindred typically develop cognitive decline (Arboleda-Velasquez et al., 2019). Clinical assessment revealed accumulation of amyloid plaques, but low levels of tau pathology, leading to the concept that the APOE3ChC variant blocked development of tau pathology. This was corroborated with in vitro experiments demonstrating that APOE3ChC behaves like the APOE2 allele; both bind poorly to heparin (APOE3ChC>APOE2) compared to APOE4 which binds tightly (Mahley et al., 1999; Zhao et al., 2016; Rosenberg et al., 2018; Arboleda-Velasquez et al., 2019). The observation that the inheritance of APOE3ChC prevents PSEN1-E280A-driven development of tau pathology but not amyloid pathology (Arboleda-Velasquez et al., 2019), together with gene therapy studies demonstrating that APOE4-driven amyloid pathology can be suppressed by AAV-mediated delivery of APOE2 to the CNS, led to testing, in mouse models of AD amyloid and tau pathology, whether AAVrh.10-mediated delivery to the CNS of APOE3ChC (APOE3 with Christchurch variant) suppresses tau-related pathology and whether delivery of APOE2ChC (APOE2 with Christchurch variant) suppresses both amyloid and tau pathology. 2 mouse, human E4-based models are used: APP.PS1/TRE4 exhibiting APP and APOE4-associated amyloid pathology (Zhao et al., 2016; Rosenberg et al., 2018; Arboleda-Velasquez et al., 2019; Lopera et al., 1997; Kim et al, 2011) and P301S/E4 exhibiting tau and APOE4 associated tau pathology (Liu et al., 2016; Allen et al., 2002).

Strategy

Heredity plays a major role in the risk for Alzheimer's disease (DeTure & Dickson, 2019; Holtzman et al., 2012; Safieh et al., 2019; Fernandez et al., 2019). Early-onset autosomal dominant AD is caused by mutations in amyloid protein precursor (APP) and presenilin 1 (PSEN1) and 2 (PSEN2) (Campion et al., 1999; Carmona et al., 2018), genes that affect the processing of APP, altering the production of Aβ peptides, resulting in aggregation and increased plaque formation (Carmona et al., 2018; Dai et al., 2018). The major genetic factors for sporadic late-onset AD are variants of apolipoprotein E (APOE), a lipid transport protein (Tzioras et al., 2019; Wolters et al., 2019). APOE has three common isoforms, ε2, ε3, ε249; the common ε3 isoform is associated with an average risk for AD, ε4 increases the risk and reduces the age of onset of AD, while ε2 decreases risk and delays the age of onset (Wolters et al., 2019; Corder et al., 1994; Naj et al., 2011). At the biologic level, the APOE genotype ε4>ε3>ε2 predicts the timing and amount of brain amyloid, p-tau and tau tangles in humans and mouse models of AD (Tzioras et al., 2019; Shi et al., 2017; Abner et al., 2018). Based on the knowledge that inheritance of different variants of the APOE genes can dictate the AD risk, age of onset and severity (DeTure & Dickson, 2019; Shinohara et al., 2016), it was envisioned that a therapy to reduce the CNS-related Alzheimer's pathology in APOE4 homozygotes could be accomplished by delivering "APOE AD decreased risk" variants to the CNS, Prior studies demonstrated that APOE2 delivery to the CNS mediated by AAV serotype rh.10 (AAVrh.10), reduced Aβ and amyloid burden in mouse models of AD (Zhao et al., 2016). The ability of APOE2 to reduce brain Aβ burden in these mouse models was dependent on gene dose and the amount of pre-existing Aβ1-42 deposition, suggesting that, if sufficient brain APOE2 levels could be achieved early in the course of the disease, gene delivery of APOE2 using an AAV vector was a viable therapeutic approach for treating or preventing AD (Zhao et al., 2016). This data, along with studies demonstrating the ability to deliver and safely achieve high levels of APOE2 expression in the CNS of non-human primates using intracisternal route (Rosenberg et al., 2018), led to a first-in-human ongoing clinical study to treat APOE4 homozygotes with intracisternal administration of AAVrh10hAPOE2.

An "APOE AD decreased risk" gene therapy strategy that is more effective than gene therapy with APOE2 in mitigating development of APOE4-driven AD-related pathology is envisioned. The approach is based on a recent report of the consequences of the APOE3-Christchurch (APOE3ChC) mutation superimposed on the Colombian PSEN1-E290A mutation, a PSEN1 variant in a family affecting >1,200 individuals (Lopera et al., 1997; Acosta-Baena et al., 2011). The PSEN1-E280A mutation is associated with an increased Aβ production, leading to amyloid accumulation; heterozygotes develop dementia in their mid-forties (Lopera et al., 1997). A female from this kindred with the autosomal dominant PSEN1 E280A mutation, but also homozygous for the APOE3ChC variant, is in good cognitive condition at age 70 and remains independent, well past the age of 40 yr, when those with the same PSEN1 mutation typically demonstrate cognitive decline (Arboleda-Velsquez et al., 2019). Clinical assessment revealed significant accumulation of amyloid plaques, but low tau/p-tau pathology suggesting that the APOE3ChC mutation may have blocked development of tau pathology (Arboleda-Velsquez et al., 2019). Of interest, the APOE3ChC variant (R1365) is in the same region of the APOE protein as the common ε2, 3 and 4 alleles (112-158), consistent with the concept that this region of APOE is related to risk for AD (Mahley et al., 1999).

Figure 11:
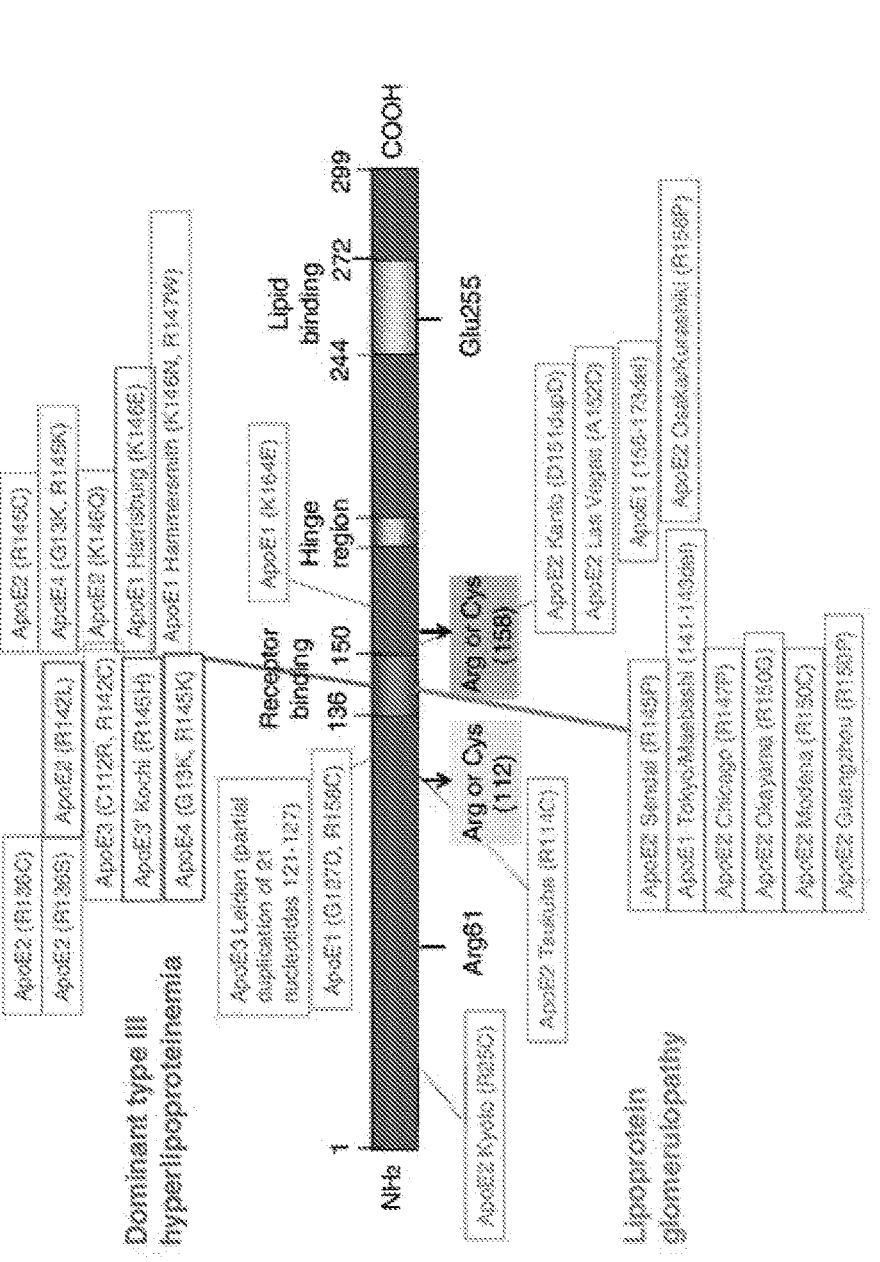
FIG. 11. Association of APOE alleles with Dominant type III hyperlipoproteinemia and lipoprotein glomerulopathy.
Figure 12:
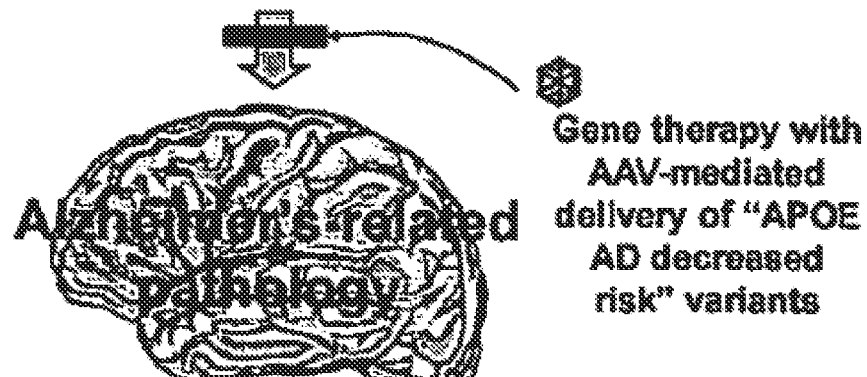
FIG. 12. Gene therapy with AAV-mediated delivery of APOE AD decreased risk variants. Based on the knowledge that APOE4 homozygotes have a 15-20-fold increased risk for AD (Reiman et al., 2020; Corder et al., 1993; Hefferman et al., 2016), a therapeutic strategy is employed using an AA

The ability of the APOE3ChC variant to suppress tau pathology was corroborated with in vitro experiments demonstrating that APOE3ChC behaves like the APOE2 allele; both bind poorly to heparin (APOE3ChC<APOE2) (Mahley et al., 1999; Arboleda-Velsquez et al., 2019). These findings suggest that the AD-related chain of pathogenic events is likely broken by APOE3ChC after amyloid formation, and independent of the mechanism, the Christchurch mutation is protective, can be used to treat APOE4 homozygotes, and likely will be more effective than gene therapy with the APOE2 allele (FIGS. 12-13). Using the AAVrh.10 capsid as a delivery system in relevant AD mouse models, it is assessed AAVrh.10-mediated delivery to the CNS of either APOE3 or APOE2 each harboring the Christchurch mutation, are superior to AA Vrh.10hAPOE2 as a treatment for Alzheimer's disease in APOE4 homozygotes. Based on the prior demonstration that AAVrh.10hAPOE2 suppresses amyloid accumulation in murine models (Zhao et al., 2016), and the clinical case report on the Christchurch variant, it is likely that AAVrh.10hAPOE3ChC suppresses tau, but not amyloid, pathology, and that AAVrh.10hAPOE2ChC may be more effective, suppressing both amyloid and tau pathology.

PSEN1-APOE3ChC. While the report of an individual who inherited the APOE3ChC variant along with Colombian PSEN1-E280 mutation only represents a single case, the report included additional studies that support the conclusion that APOE3ChC is an "APOE AD decreased risk" variant, Although amyloid PET scanning revealed a significant accumulation of CNS amyloid plaques, very little tau pathology was observed, and was mostly confined to the medial temporal lobe. In addition, brain glucose metabolism was almost normal (FIG. 14). The concept that the APOE3ChC mutation blocks development of tau pathology is similar to the concept in the study by Reiman et al. (2020) that observed in 24 autopsy samples from APOE2 homozygotes that APOE2 was associated with decreased tau pathology. The ability of the APOE3ChC variant to suppress tau pathology was supported by in vitro experiments demonstrating that APOE3ChC behaves like the APOE2 allele; and that compared to E4, E2 and E3ChC both bind poorly to heparin (binding: E4>E3>E2»E3ChC, FIG. 15). HSPGs have been implicated in the buildup of amyloid plaques, as well as in promoting microglial response to amyloid (Heffernan et al., 2016; ALXFORUM, 2010; Snow et al., 1988; Liu et al., 2016; O'Callaghan et al., 2018). HSPG have also been linked to tau pathology; it has been suggested that HSPG allow tau fibrils to attach to neurons, facilitating uptake and propagation of toxic forms of tau (Rauch et al., 2018; Zhao et al., 2019). In vitro studies also demonstrated that APOE3 bound with an antibody to residues 130-143 (which includes the region of the Christchurch mutation) converted APOE3 functionally to APOE3ChC as measured by heparin binding. Together, these findings suggest that the Alzheimer's related chain of pathogenic events is likely broken by APOE3ChC alter amyloid formation, and independent of the mechanism, since the Christchurch mutation is protective, it be used to treat APOE4 homozygotes.

APOE4-associated risk for AD. APOE, a lipid binding protein, is the major carrier of cholesterol in the CNS (Puglielli et al., 2003; Williams et al., 2020). In the brain it is mainly produced by astroglia and microglia (Flowers & Rebeck, 2020; Pitas et al., 1987; Holtzman et al., 2012). The APOE particles are formed in the extracellular milieu (Mahley et al., 1999; Flowers & Rebeck, 2020); the APOE particle transports cholesterol to neurons via APOE receptors, members of the low density lipoprotein receptor gene family (Liu et al., 2013; Mondadoori et al., 2007; Zhang et al., 2013). The APOE protein (299 amino acids) has N-terminal (1-167) and C-terminal (206-299) domains connected by a hinge region (Safieh et al, 2019; Flowers & Rebeck, 2020). The C-terminal region contains the low density lipoprotein receptor binding site41 (FIG. 2). In addition to its role in transporting cholesterol in the CNS, APOE has myriad other functions (Holtzman et al., 2012; Castellano et al., 2011; Deane et al., 2008; Hashimoto et al., 2012; Hatters et al., 2006a; Hatters et al., 2006b; Li et al., 2012; Manelli et al., 2005; Walker et al., 2000; Yu et al., 2014; Zhao et al., 2009). Human APOE is commonly expressed in 3 isoforms (APOE2, 3, and 4) that differ only by two residues (Mahley et al., 1996; Zannis et al., 1981) (FIG. 13). Inheritance of APOE4 is the most important genetic risk factor for AD, APOE3 is neutral, the E4 allele increases risk and reduces age of onset and E2 decreases risk and delays age of onset (Reiman et al., 2020; Mahley, 2016; Conejero-Goldberg et al., 2014; Nagy et al., 1995; Raber et al., 2004). Epidemiologic data suggest that APOE4 and APOE2 are co-dominant, that is, E2/E4 heterozygotes, instead of having the 4-fold higher risk for AD of E3/E4 heterozygotes, have close to the normal risk of E3/E3 homozygotes (Corder et al., 1994; Liu et al., 2013; Genin et al., 2011), i.e., roughly equivalent expression of E2 cancels out the deleterious effect of the E4 allele (Corder et al., 1994; Farrel et al., 1997; Coon et al., 2007). The key conclusions from epidemiologic studies of the protective effects of E2 studies include: the E2 genotype is markedly underrepresented in AD (Corder et al., 1994; Reiman et al., 2020); the E2 allele is associated with a delayed age-of-onset of AD (Reiman et al., 2020; Benjamin et al., 1994); E2 carriers have reduced AD-related pathology (Reiman et al., 2020; Nagy et al., 1995); E2 is associated with slower cognitive decline (Small et al., 2004); E2 carriers harbor more robust white matter integrity that may be associated with decreased vulnerability to developing AD (Chiang et al., 2012); and in normal elderly, E2 carriers have lower levels of cerebrospinal fluid p-Tau and marginally lower tau (Chiang et al. 2010). Experimental studies demonstrate that E2 promotes metabolism of Aβ; neuronal repair and neurite outgrowth; and acts as an anti-oxidant and anti-inflammatory agent (Rebeck et al., 2002). Further, animal and clinical studies have shown that APOE genotype also predicts the timing and amount of brain amyloid β (Aβ) peptide deposition as well as amyloid burden (E4>E3>E2) (Castellano et al., 2011; Raber et al., 2004; Bales et al., 2009; Holtzman et al., 2000; Reiman et al., 2009; Schmechel et al., 1993), i.e, APOE4 impairs amyloid p clearance and increases amyloid formation 70,71. (Liao et al., 2017; Hu et al., 2015). Murine studies in mice have shown that targeted deletion of the endogenous ApoE gene results in a dramatic decrease in fibrillary amyloid and total brain Aβ deposition in the PDAPP mouse model of AD (these mice express a mutant APP transgene resulting in high brain levels of human Aβ) (Bales et al., 1997). By crossing PDAPP mice to human APOE targeted replacement (TRE) mice, APOE isoform-dependent effects were observed in brain Aβ deposition and amyloid burden (E4>>E3>E2) in a manner that recapitulates what is observed in AD patients (Castellano et al., 2011; Bales et al., 2009; Holtzman et al., 2000; Fagan et al., 2002), suggesting that the APOE isoforms play an important role in determining brain amyloid burden. Further, studies in tau pathology-related P301S/E3, E2 and E4 mice demonstrate ApoE affects neurodegeneration in the context of tau pathology independently of amyloid-β. ApoE4 resulted in aggravated neurodegeneration whereas the absence of ApoE was neuroprotective (Shi et al., 2017).

APOE2 gene therapy for APOE4-related CNS pathology. Based on the epidemiologic data of APOE2 being protective, a gene therapy program was developed to assess the hypothesis that transfer of APOE2 to the CNS of APOE4 homozygotes would mitigate the E4 risk (Zhao et al., 2016; Rosenberg et al 2018). Evidence in the literature of the feasibility of this approach came from studies of Dodart et al. (2005) who demonstrated that administration of APOE4 and APOE2 to the CNS of murine AD models using lentivirus vectors increased and decreased, respectively, brain Aβ/amyloid burden. The finding that APOE2 decreased brain AI3/amyloid burden was replicated by Hudry and colleagues (2013) using an AAV4 vector to deliver APOE2 into the lateral ventricle of mutant APP mice. Using AAV8 vectors administered to the CSF, Hu et al. (2015) found that increasing APOE2 in TRE4 mouse models, was an efficacious strategy to treat AD; whereas, increasing APOE4 in TRE4 mice was deleterious. As described in detail below, an AAVrh.10 serotype vector coding for human APOE2 reduces the amyloid burden in 2 murine models (Zhao et al., 2016). Irrespective of the molecular mechanisms by which these APOE alleles determine AD risk, given the fact that APOE2 is strongly protective and when delivered to the mouse brain via either gene therapy vector markedly reduces Aβ/amyloid burden. CNS gene delivery of APOE2 via viral vectors represents a therapeutic strategy for APOE4 homozygous AD.

AAVrh.10. The AAVrh.10 serotype is derived from a rhesus macaque. This serotype has been administered with various expression cassettes to the ONS of experimental animals (mice, nonhuman primates) to children with CLN2 disease and adults with Alzheimer's disease (clinicaltrials-.gov: NCT01414985, NCT01161576, NCT03634007). The AAVrh.10 vectors are designed with a highly active constitutive promoter, intron coding sequence and the rabbit β-globin polyA flanked by AAV2 inverted terminal repeats (as an example see FIG. 16 for details of the AAVrh.10hAPOE2 vector). The AAVrh.10 capsid is highly effective at mediating gene expression in the CNS, equivalent to AAV9, but with less potential toxicity (Rosenberg. et al. 2018: Rosenberg et al., 2014; Sondhi et al., 2012 Tardieu al., 2014; Zerah et al., 20150. All vectors are characterized for numerous measures of identity, potency and purity.

Purity by polyacrylamide gel electrophoresis establish the absence of contaminant proteins from the cells used in vector production (FIG. 17). As a demonstration of the effectiveness of the intracisternal administration of a vector coding human APOE2 to nonhuman primates (NHP) provide broad distribution of vector derived protein throughout the CNS including the cerebral spinal fluid (FIG. 18). These observations support that CNS administration of an AAVrh.10 vector coding for a human APOE isoform can effectively distribute the coding APOE isoform throughout the CNS.

AA Vrh.10hAPOE2 ameliorates pathology in AD animal models. The PDAPP mouse is a well characterized mouse model of brain amyloidosis that overexpresses a human APP mutation and develops age-dependent Aβ and amyloid deposition in the hippocampus and cerebral cortex (Games et al., 1995; Schenk et al., 1999). At 9 months of age, there are abundant Aβ and amyloid plaques in the hippocampus80. Expression of the AAVrh.10hAPOE2 vector demonstrated significant resolution of the amyloid pathology observed in control animals treated with a similar viral vector expressing an irrelevant gene (FIG. 19) (Zhao et al., 2016). Expression of APOE2 using the AAVrh.10hAPOE2 vector resulted in a marked decrease in insoluble Aβ1-42 (70.4% reduction. p<0.001 vs the mCherry control) and soluble Aβ1-42 (27.2% reduction, p<0.05 vs mCherry control) levels in the hippocampus of PDAPP mice. Insoluble Aβ1-40 was also dramatically decreased (61.2% reduction. p<0.001 vs control) although the relatively already low levels of soluble Aβ1-40 were not altered.

Figure 20:
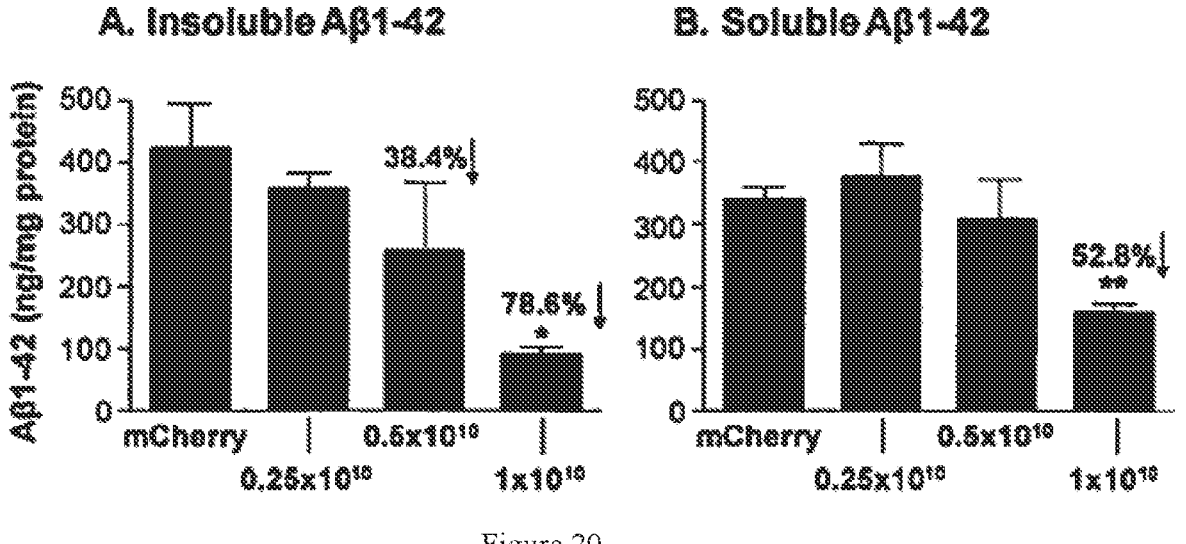

To further assess the role of APOE2 expression on brain Aβ burden, the impact of AAVrh.10hAPOE2 dose on Aβ/amyloid pathology in APP.PS1/TRE4 triple transgenic mice was also evaluated. APP.PS1/TRE4 mice carry the APP Swedish (APPswe) and PS1 mutations as well as the human APOE4 gene (Kim et al., 2011; Jankowsky et al., 2018). APP.PS1/TRE4 mice develop robust age-dependent dependent Aβ and amyloid pathology in multiple brain regions including the cerebral cortex, hippocampus, and thalamus. Amyloid plaques are observed in the cortex of these mice as early as 2 months of age and the brain AJ3/amyloid burden that develops is dependent on APOE4 expression (Kim et al., 2011). Similar to the observation in the PDAPP mice, dose-dependent suppression of amyloid-beta levels was observed in the hippocampus of APP.PS1/TRE4 mice treated with intra-hippocampal delivery of AAVrh.10hAPOE2 (FIG. 20).

Mouse models of APOE4-related AD pathology. The clinical goal is to suppress both amyloid and tau pathology in the CNS of APOE4 homozygotes, and thus murine models were chosen with murine ApoE knockouts and human APOE4 knockins. One murine model for APOE4-related amyloid pathology and another one is for APOE4-related tau pathology. The APP.PS1/TRE4 mouse expresses the human β-amyloid (Aβ) precursor protein (APP) with the Swedish mutation (APPswe), mutant (L 166P) human pre-senilin 1 and the human APOE4 gene replacing the endogenous mouse ApoE gene. These mice express high levels of human Aβ protein and human AD-like amyloid pathology (Kim et al. 2011) and were used in our prior studies to demonstrate that AAVrh.10hAPOE2 will suppress AD amyloid-related pathology (Zhao et al., 2016) (FIG. 20). The P301S/E4 mouse harbor the human P301S 1N4R tau, deletion of the murine ApoE gene and addition of the human APOE4 gene (Shi et al., 2017; Allen et al., 2002). These mice have APOE4-related tau pathology and will be used to evaluate the ability of the gene therapy vector to suppress tau pathology. These mice also have microglial and astrocyte activation, representing AD-related inflammation (Shi et al., 2017).

Approach. The Christchurch variant (APOE3-R 136S) is in the APOE 112-158 "Alzheimer's risk region" that includes residues 112 and 118 that define APOE2, 3 and 4, the LDL binding region (136-150) and the proteoglycan heparan sulfate binding region (FIG. 13). The demonstration that the APOE4-associated Abeta and amyloid burden in an APOE4-related mouse model could be prevented with CNS administration of AAVrh.10APOE2 supports the concept that the APOE4-associated risk for AD might be mitigated by using gene therapy delivering the APOE2 coding sequence to convert the APOE4 homozygote brain to an APOE2-APOE4 heterozygote state (Zhao et al., 2016). The report of a woman in the PSEN1-E290A kindred with concomitant homozygous inheritance of APOE3ChC that negated the PSEN1-E290A driven AD-related tau pathology, led to the focus of this proposal: to develop a 2nd generation gene therapy for APOE4 homozygotes using an AAVrh.10 vector to deliver the Christchurch mutation on either the APOE3 or APOE2 background, We will test this in 2 human APOE4-related mouse models: APP.PS1ffRE4 demonstrating primarily amyloid-related pathology and P301S/E4 demonstrating primarily tau-related pathology (Shi et al., 2017; Kim et al., 2011). If the Christchurch variant on the APOE3 background is effective in the mouse models equivalent to the case report of dual inheritance of PSEN1-E290A and APOE3ChC, then gene therapy with AAVrh.10APOE3ChC should suppress tau pathology in the P301S/E4 mouse but not the amyloid pathology in the APP.PS1ffRE4 mouse. However, based on the effectiveness of AAVrh.10hAPOE2 in suppressing amyloid pathology in the APP.PS1ffRE4 mouse (Zhao et al., 2016), we hypothesize that AAVrh.10hAPOE2ChC will suppress both the amyloid pathology in the APP.PS1ffRE4 mouse and also the tau pathology in the PSEN1-E290A mouse. If the hypothesis is correct, AAVrh.10hAPOECHC will be an ideal $2^{nd}$ generation candidate to move to the clinic to treat APOE4 homozygotes. Other than the different vectors (AAVrh.10hAPOE3ChC and AAVrh.10hAPOE3, or AAVrh.10hAPOE2ChC and AAVrh.10hAPOE2), everything is identical. The statistical analysis includes comparison of the parameters within each experiment, and separately, to compare the differences of AAVrh.10hAPOE3ChC and AAVrh.10hAPOE2ChC.

For each mouse model (APP.PS1ffRE4, P301 S/E4) the vectors AAVrh.10hAPOE3ChC, AAVrh.10hAPOE3; AAVrh.10hAPOE2ChC, AAVrh.10hAPOE2; controls for both, AAVrh.10Null (no translatable transgene) or PBS] are administered at 2 months of age bilaterally to the hippocampus in 2 μl. The vectors are administered with 2 doses $0.4 \times 10^{10}$ genome copies (gc) or $1.0 \times 10^{10}$ gc. Assessments will be at 5 and 9 months. Ten males and 10 females will be used for all data points (mouse strain, vector or PBS, assessment time points; Table I). The assessments to be conducted related to the vectors, general pathology, amyloid, tau and inflammation are listed in Table II. Based on AAVrh.10hAPOE2 effectively suppressing amyloid-related pathology in APP.PS1ffRE4 mice (Zhao et al., 2016), and the case report of homozygous inheritance of APOE3ChC allowing for amyloid pathology but preventing the tau pathology in a female carrier in the PSEN1-E280A kindred (Arboleda-Velasquez et al., 2019), we both the hAPOE3ChC and hAPOE2ChC vectors are likely more effective than the hAPOE3 and hAPOE2 vectors without the ChC variant, and the hAPOE2ChC construct is likely more effective than the hAPOE3ChC construct in preventing both amyloid and tau pathology. Also tested are: (1) the effectiveness of the hAPOE3ChC and hAPOE2 vectors on more general pathology (quantitative volumes of AD-relevant CNS structures, transcriptome analysis of general cell functions); and (2) AD-related inflammation (microglia and astrocyte activation, transcriptome analysis of proinflammatory genes) because the E4 variant is associated with greater innate immune-related inflammation than the E2 and E3 variants (Vitek et al., 2009, Gale et al., 2014).

TABLE I

AAVrh.10-mediated Therapy with APOE Variants of APP.PS1/TRE4 and P301S/E4 Mouse Models of Human APOE4-related AD Pathology

| Parameter | Variable |
|---|---|
| Mouse model | APP.PS1/TRE4, P301S/E4 |
| Transgene (AAVrh.10 vectors) | APOESChC, APOE3; APOE2ChC, APOE2; -Null, PBS[1] |
| Route, dose | Bilateral hippocampus, $0.4 \times 10^{10}$ gc, $1 \times 10^{10}$ gc2 |
| Age at vector administration | 2 months[2] |
| Age of assessment | 5, 9 months[3] |
| Number of mice/time-point, dose | 10 M, 10F |
| Total number of mice | 880 |

Each mouse model is treated with PBS or AAVrh.10 vectors coding for the listed transgenes; All administrations are at 2 months, bilateral to the hippocampus at the listed doses in 2 μl each; Assessment of the CNS is at 5 and 9 months, see Table II for list of parameters to be assessed

TABLE II

Assessment of the Efficacy of APOE Variants in the APP.PS1/TRE4 and P301S/E4 Mouse Models of Human APOE4-related AD Pathology

| Parameter | Assessment |
|---|---|
| Vector-related | Transgene DNA, mRNA, protein (Western, immunohistochemistry) |
| General pathology | Quantitative volumes, transcriptome of general cell function (RNAseq) |
| Amyloid-related | Soluble, insoluble Aβ-1-42, Aβ-1-40 (ELISA, immunohistochemistry) |
| Tau-related | Total tau, p-tau (ELISA, immunohistochemistry) |
| Inflammation-related | Microglia, astrocyte activation (CD68 immunohistochemistry, RNAseq proinflammatory genes) |

Each mouse model is administered AAVrh.10hAPOE3ChC, hAPOE3, hAPOE2ChC, hAPOE2, Null (0.4 × 10^{10} gc or 1 × 10^{10} gc; bilateral, hippocampus) or PBS at 2 months of age and evaluated at 5 and 9 months of age. Ten males, 10 females for each vector, each dose, each time-point; PBS 10M, 10F each timepoint; DNA, mRNA by qPCR, APOE proteins are assessed by quantitative Western, quantitative immunohistochemistry; Quantitative volumes of piriform/entorhinal cortex, hippocampus, posterior lateral ventricle, and thickness of dentate gyrus are assessed; RNAseq of quantitative transcriptome of general cell function-related is assessed; Soluble (RIPA) and insoluble Aβ-1-42 and Aβ-1-40 are assessed by ELISA and immunohistochemistry of Aβ (positive % area of hippocampus, Aβ plaque burden); ELISA and immunohistochemistry of tau and p-tau (positive % area of hippocampus, tau tangle quantification are assessed); Quantification of microglia (CD68, Iba1) and astrocytes (GFAP) are assessed by cell count and % area of hippocampus, RNAseq quantitative transcriptome of proinflammatory genes.

Methods.

Vector-related. The MVrh.10 vectors are produced and purified as described previously ((Sondhi et al., 2012; Sandhi et al., 2007). Briefly, the vectors are produced by cotransfection of HEK293T cells with an expression cassette plasmid and adenoviral helper plasmids. The packaging cell line, HEK293T, is maintained in Dulbecco's modified Eagles medium, supplemented with 5% fetal bovine serum, 100 U/ml penicillin, 100 mg/ml streptomycin, and maintained at 37° C. with 5% $CO_2$. The cells are grown in CellSTACKS (Corning) for 24 hours followed by transfection with plasmids using the PEIpro procedure. The cells are incubated 3 days before harvesting and lysed by 5 freeze/ thaw cycles. The resulting cell lysate is treated with 50 U/ml of benzonase at 37° C., 30 minutes. The cell lysate is purified by iodixanol density gradient followed by Q-HP ion-exchange chromatography. The purified AAVrh.10 vectors are concentrated in phosphate buffered saline (PBS). Vector genome titer is determined by TagMan quantitative polymerase chain reaction. The purified vectors are sterile filtered; tested 14 days for growth on medium supporting the growth of aerobic bacteria, anaerobic bacteria, or fungi; tested for endotoxin; and demonstrated to be mycoplasma free.

Mouse models. The APP.PS1/TRE4 mouse colony, derived from crossing APP.PS1-21 mice with human APOE4 knockin mice, are established (Zhao et al., 2016). The P301 S/E4 mice are generated by crossing human tau mutant P301S mice with human APOE4 knockin mice. The genome of the mice is validated by PCR of the relevant knockin genes. Intracerebral injection of AAV vectors is carried out by stereotaxic surgery (Dodart et al., 2005). Briefly, under sterile conditions, mice are anesthetized with isoflurane and secured on a stereotaxic frame (David Kopf Instruments). An incision is made over the skull, and burr holes of the size of the injection needle are made using a high-speed drill. The AAV preparation (2 gc at the indicated dose) is bilaterally injected into the targeted brain regions using a 33-gauge needle (Hamilton) and a syringe pump (KD Scientific) at a rate of 0.2 μL/min. Stereotactic coordinates used for injections are as follows: ±1.7 mm antero-posterior from bregma; ±1.2 mm mediolateral from bregma, and ±1.7 mm dorsoventral below the dura. This is based on an atlas of the mouse brain95. After each injection, the needle is left in place for 5 minutes to minimize backflow and then slowly withdrawn. Animals are individually housed and monitored until they regained full consciousness. At 5 months and 9 months of age, the mice are deeply anesthetized with ketamine/xylazine and transcardially perfused with 0.3% heparinized saline (2500 IU/L). Brains are rapidly collected, and each brain will be divided along the sagittal plane with 1 hemibrain processed for histologic and immunohistochemistry (IHC) analyses, and the other hemibrain microdissected into the hippocampus, thalamus, and entorhinal cortex then rapidly frozen on dry ice and stored at −80° for biochemical analyses.

Brains are post-fixed in 4% paraformaldehyde for 48 hours, transferred to 30% sucrose for ≥48 hours before freezing, and sectioned using a CM3050-S cryostat (Leica). Serial coronal sections are prepared at 50 μm intervals. IHC analyses will be performed using standard methods (Bales et al., 2009; Holtzman et al., 2000; Bales et al., 1997). Free-floating sections are washed and incubated with primary antibodies overnight at 4° C. Immunoreactivity (IR) are visualized using Alexa Fluor 488 or 594-conjugated secondary antibodies (1:200; Invitrogen) or the Vectastain ABC Elite kit (Vector) and 3,3-diaminobenzidine solution. The specificity of the primary antibodies staining is verified by the lack of IR signal when the primary antibodies were omitted. Thioflavin-S staining is performed as to detect amyloid plaques (Bales et al., 2009; Holtzman et al., 2000; Bales et al., 1997). Fixed brain sections are briefly incubated with 0.1% freshly made thioflavin-S solution (in 50% ethanol) for 8 minutes and then cleared with 80% ethanol for 1 minute followed by washing with $H_2O$ 3× for 1 minute each before being cover slipped with mounting media. Images are taken using an epifluorescence microscope (Nikon H550L).

Vector-derived APOE. For tissue homogenates processed for vector DNA, the DNeasy Blood and Tissue Kit (cat #69506; Qiagen) will be used with about 50 mg of homogenized tissue sample. For tissue homogenates processed for vector transgene mRNA, the RNeasy Lipid Tissue Mini kit (Qiagen) will be used with ~50 mg of homogenized tissue sample. Quantitative analysis of vector DNA and transgene mRNA copies in the brain sections will be performed by PCR using a TaqMan-based analysis (Applied Biosystems "Universal Master Mix II, no UNG" reagent) and a human-specific primer/probe set (Applied Biosystems) to detect the 3' terminus of the human APOE2 or E3 or E4 cDNA from viral genomes, in the background of murine genomic DNA (forward primer: 5'GTGGAGAAGGTGCAGGCT-3' (SEQ ID NO:10); reverse primer: 5'-AAGCGTAATCTGGAA-CATCGT-3' (SEQ ID NO:11); probe, 5'CCCTGTGCCCAGCGACAATC-3' (SEQ ID NO:12). The PCR is performed using the QuantStudio6 Flex system (Applied Biosystems) (Rosenberg et al., 2018). APOE levels are measured in brains using a sandwich ELISA (Bales et al., 2009). Tissue homogenates are diluted in sample dilution buffer (PBST containing 0.4% glycine). Samples were loaded into 96-well plates coated with an anti-APOE antibody (1:2000; Millipore). After overnight incubation at 4° C., a biotinylated anti-APOE antibody (1:10,000; Meridian Life Science) is used for detection. The IR signal after incubation with HRP-conjugated streptavidin (Research Diagnostics) is developed with a TMB substrate (Thermo Scientific) and read on a Synergy H1 Hybrid plate reader (BioTek). Levels of APOE are calculated using a standard curve generated with recombinant human APOE (Meridian Life Science). Levels of APOE in brain homogenates are determined in triplicate, normalized to protein content, and expressed as the amount of APOE/mg protein. Examination of APOE and other protein levels in mouse brain tissue homogenates is also carried out by Western analysis (Zhao et al., 2016; Sacramento et al., 2020). The total protein concentration in tissue homogenates was determined using a BCA protein assay kit (Thermo Scientific). For sodium dodecyl sulfate (SOS) polyacrylamide gel electrophoresis, equivalent amounts of protein (25 mg) samples are mixed with loading dye containing 2% SDS and 1% 3-mercapto-ethanol, incubated for 10 minutes at 90'C, and resolved on 10% Tris-glycine polyacrylamide gels. For nondenaturing PAGE, equivalent amounts of protein (25 μg) samples are mixed with nondenaturing loading dye to a final concentration of 0.04% bromophenol blue, 4.0% glycerol, and 100 mM Tris (pH 6.8) and resolved on 4-12% nondenaturing Tris-glycine polyacrylamide gels (Invitrogen). Proteins are transferred onto polyvinylidene difluoride (Millipore) membranes at 100 V. After blocking with Superblock (Thermo Scientific) for 1 hour, 23° C., membranes are probed with primary antibodies overnight at 4° C. followed by species-specific HRP-conjugated secondary antibodies (1:8000; Invitrogen) for 1 hour, 23'C. Enhanced chemiluminescence (GE Healthcare Biosciences) is used to identify the bands. Protein molecular weights on denaturing gels are determined by comparison with the kaleidoscope molecular weight marker standard (Bio-Rad). Particle diameters on native gels is determined by comparison with a native high molecular weight marker standard (GE Healthcare Biosciences). Signal quantification is done using densitometry analysis of the scanned, autoradiograms with Image Lab software (Bio-Rad). Loading is normalized by stripping blots and reprobing with a β-actin antibody (Sigma-Aldrich).

General Pathology.

Volumetric analysis. Every 6th coronal brain section (300 μm between sections) starting rostrally at bregma +2.1 mm to the dorsal end of the hippocampus at bregma −3.9 mm are cryosectioned for each mouse. The mounted sections are stained with 0.1% Sudan black in 70% ethanol at RT for 20 minutes, then washed in 70% ethanol for 1 minute, 3 times. The sections are washed in Milli-Q water for 3× and coverslipped with Fluoromount. The stained slices are imaged with the NanoZoomer and areas of interest traced and measured in each slice using the NOP viewer. The volume is calculated using the formula: volume=(sum of area)×0.3 mm. For hippocampus and posterior lateral ventricle, quantification starts from bregma and ends at bregma −3.9. For piriform/entorhinal cortex, quantification starts at bregma 2.3 and ends at bregma −3.9.

Neuronal layer thickness measurement. Three sections (bregma −1.4, −1.7, and −2.0 mm) from each mouse are mounted and stained in cresyl violet for 5 minutes at RT. The slices are then sequentially dehydrated in 50%, 70%, 95% (3 times) and 100% ethanol (twice) for 1 minute, then cleared in xylene for 4 minutes (twice), and cover slipped in cytoseal (Coon et al., 2007) (Thermo Fisher Scientific, 8310-16). The thickness of the CA1 pyramidal cell layer and dentate gyrus granular cell layer are measured by drawing a scale perpendicular to the cell layer at two spots in all 3 slices and taking the average value for each mouse.

RNASeq transcriptome analysis. Total RNA is extracted using the TRIzol method and subsequent clean-up was performed on RNeasy columns (Qiagen). RNA quantity was assessed by Nanodrop ND-1000 (Thermo Scientific) and RNA quality assessed by Bioanalyzer (Agilent Technologies) (Raman et al., 2009; Tumor Analysis, 2004). Total RNA is purified, amplified and loaded onto an Illumina flowcell for paired-end sequencing reactions using the Illumina HiSeq 2500 (Illumina) (Ryan et al., 2014). The library is prepared using (0.5 µg total RNA) TruSeq RNA Library Prep Kit v2. Illumina HiSeq paired-end reads are aligned to GRCh37/hg19 human reference genome and RefSeq gene definitions (2014-06-02) using STAR (2.3.1z13_r470). Cufflinks (2.2) is used to convert aligned reads into fragments per kilobase of exon per million fragments sequenced (FPKM) using RefSeq gene definitions. Genes with FPKM>0.125 are included in the analysis. The dysregulated genes are functionally annotated using Gene Ontology (GO) and the Human Protein Reference Data Base (www.hprd.org). A 2-tailed Student's t-test is used for comparison of numerical data and a chi-square test is used with Yates' correction is used for comparison of categorical data. The files are processed in Partek Genomics Suite software version 6.6, 2012 (Partek). A 1-way ANOVA is used to compare the matched groups, and a 2- or 3-way ANOVA is used to compare groups with parameters identified as a source of variation. A p value <0.05 is considered significant (p value was corrected for multiple testing using with Benjamini-Hochberg correction). Relevant to "general pathology," normal cell function genes and autophagy-related genes are assessed as detailed in the Shi et al. (2017) study.

Amyloid-related. Quantification of amyloid/Aβ burden is performed using standard methods (Zhao et al., 2016; Bales et al., 2009; Holtzman et al., 2000; Bales et al., 1997). Briefly, 4 brain sections per mouse, each separated by 300 µm, are selected for quantification. These sections correspond roughly to sections at Bregma −1.4, −1.7, −2.0, and −2.3 mm in the mouse brain atlas (Franklin et al., 2019). Quantification of brain Aβ burden is completed after immunostaining with the biotinylated 3D6 antibody (Zhao et al., 2016). Images are thresholded to highlight plaques and then analyzed by the "Analyze Particles" function of the ImageJ software (National Institutes of Health). After thresholding, identified objects are individually inspected to confirm each object quantified is a plaque. The percentage of surface area covered by AβIR (Aβ burden) or thioflavin-S (amyloid burden) is determined for specific areas of the hippocampal formation comprising the stratum oriens, pyramidal layer, stratum radiatum, and the dentate gyrus. Aβ or thioflavin-S burden is then represented as a % of the total area quantified. An average of 4 tissue sections is used to quantify the plaque load for each mouse. All analyses are performed in a blinded manner, with the examiner unaware of the treatment condition of any animal.

Aβ levels are assayed in brain homogenates from mice using a sandwich enzyme-linked immunosorbent assay (ELISA) using standard methods (Bales et al., 2009; Holtzman et al., 2000; Bales et al., 1997). Briefly, brain tissue is homogenated serially with RIPA and a 5.5-M guanidine buffer containing a cocktail of protease inhibitors (1:1000; Roche). Aβ measured after the RIPA extraction represents the soluble pool of Aβ, whereas Aβ measured after guanidine extraction represents the insoluble pool. The homogenates are diluted with a cold sample dilution buffer (1% bovine serum albumin in phosphate buffered saline-0.05% tween 20 [PBST]) before measurement of Aβ1-40 or Aβ1-42. Samples are loaded onto plates coated with an antibody that specifically recognizes the C-terminal domain of Aβ1-42 (21F12), or Aβ1-40 (2G3) as the capture antibody, and biotinylated 3D6 is used for detection. The IR signal after incubation with horseradish peroxidase (HRP)-conjugated streptavidin (Research Diagnostics) is developed with a TMB substrate (Thermo Scientific) and read on a Synergy H1 Hybrid plate reader (BioTek). Levels of Aβ are calculated using a standard curve generated with recombinant human Aβ (American Peptide Company). Levels of Aβ in brain homogenates are determined in triplicate, normalized to protein content, and expressed as the amount of Aβ/mg protein. Aβ oligomers are quantified with the 3D6/biotin-3D6 sandwich ELISA (Immuno-Biological Laboratories), in which the same N-terminal (residues 1-16) antibodies are used for both capture and detection.

Tau-related. ELISAs. Human total tau, and p-tau are quantitated by pS202/T205-tau (ATS) and pT212/pS214-tau (AT100) antibodies as sandwich ELISAs as described by Chai et al. (2011). Briefly, 96-well plates are precoated with 5 µg/ml ATS, or 2 µg/ml AT100 (Thermo Fisher Scientific) overnight at 4° C. followed by blocking with Starting Block blocking buffer (Thermo Fisher Scientific). Samples (S1 or P1) are diluted in Superblock buffer (Thermo Fisher Scientific) and loaded onto the plates together with biotinylated-HT7 antibody (1:300; Thermo Fisher Scientific). After incubation for 1 hour, 23° C., samples are washed 9 times with TBS/0.5% Tween 20 wash buffer followed by incubation with streptavidin-HRP (Jackson Immunoresearch) for 30 minutes. The plates are then developed by incubating with one-step 3,3,5,5-tetramethylbenzidine (TMB) substrate (Thermo Fisher Scientific) for 30 minutes and stopped with 2N $H_2SO_4$ and then read using a BioTek Synergy H1 Hybrid Reader at 450 nm. The amount of ATS or AT100 immunoreactive tau is determined using a standard curve derived from human AD brain homogenates.

Inflammation-related. The extent and characteristics of gene therapy on the inflammation associated with the 2 murine models are assessed as described by Shi et al. (2017), Immunohistochemistry is assessed by CD68-positive and Iba-1 microglial straining and astrocyte straining (GFAP). In addition, the RNAseq data are assessed using the same proinflammatory genes used by Shi et al. (2017), with particular focus on the proinflammatory gene cluster 1 and astrocyte A1-specific (inflammation only) genes (Shi et al., 2017).

Statistical considerations. For each measurement within the categories vector-derived APOE, general pathology, Amyloid-related, Tau-related, inflammation-related (Table II) a multi-way ANOVA model is applied. The main ANOVA model includes five factors: mouse model (APP.PS1/TRE4, P301S/E4), vector (AAVrh.10-APOE3ChC, -APOE3, AAVrh.10APOE2ChC, -APOE2, AAVrh.10Null), dose ($0.5 \times 10^{10}$ and $1 \times 10^{10}$ gc), time (5 and 9 months), and sex (M/F), where additional separate ANO-VAs comparing one vector at a time to no therapy-PBS (but otherwise the same factor) are used to explore impacts compared to the PBS control. The central hypotheses are assessed with the main ANOVA models with the following pre-hoc contrasts for the Amyloid-related and Tau-related measurements: AA Vrh.1 0-APOE3ChC vs AA Vrh.1 0Null (Aim 1) and AAVrh.10APOE2ChC vs AAVrh.10Null and AAVrh.10-APOE3ChC vs AAVrh.10APOE2ChC with each of these applied between mouse strains, between doses within each mouse strain, and between time points within each mouse strain. This comprises 45 (=vector compari-sons×factor comparisons×measurements) planned tests and a Bonferroni correction is used to assess significance con-trolling an overall 0.05 type I error. As an empirical bench-mark to approximate the lower bound on power of this design, differences in soluble Aβ1-42 of 27.2% and the observed standard deviation of each group when comparing AAVrh.10hAPOE2 to control in the PDAPP mouse brain amyloidosis experiments (FIG. 8) produces power >0.85, where considering the empirical differences and standard deviations for insoluble Aβ1-42 the power would be even greater, indicating the overall design is well-powered to assess the central hypotheses. As well as these prehoc comparisons, an exploratory post-hoc testing approach (with appropriate corrections) is additionally applied to assess the amount of brain vector derived APOE for different mouse models, doses, and time of measurement, as well as to explore how the broader vector impacts (e.g., AAVrh.10-APOE3ChC and AAVrh.10APOE2ChC in comparison to each other and to AAVrh.10-APOE3 and AAVrh.10-APOE2) on general pathology and inflammation related measure-ments (volume and RNA-Seq) and to estimate contributions of mouse model, vector, dose, time of measurement and sex to these impacts.

Example 2

Overview

Alzheimer's disease (AD), a degenerative brain disease and the most common cause of dementia, currently affects 5.8 million Americans and 50 million people worldwide. AD symptoms include progressive decline of cognitive and functional abilities and brain pathology, including extracel-lular beta-amyloid plaques, intracellular tau tangles, chronic inflammation, and brain atrophy. The strongest genetic risk factor for susceptibility to late-onset AD concerns polymor-phisms in the apolipoprotein E (APOE) allele. APOE4 is found at high frequency in AD patients and homozygous inheritance is associated with a 14.5-fold increased risk of developing AD. In contrast, APOE2 decreases risk of AD development and delays onset of disease, e.g., reducing the risk of developing AD by ≥50% and delaying the age of onset, Based on the epidemiologic data, APOE4 is associ-ated with increased brain amyloid load and greater memory impairment in AD, while APOE2 attenuates these effects. In humans, the odds ratio of developing AD with APOE4/4 homozygous genotype is 14.5 and is reduced to 2.6 in APOE2/4 heterozygotes. Thus, the presence of APOE4 still constitutes a risk even when supplemented by the protective APOE2. In addition, APOE4 is associated with increased innate immune activation, differential signaling in neurons, exacerbation of tau pathology, and abnormal brain function apart from its role in promoting β-amyloid production.

Delivery of APOE2 directly to the CNS of AD murine models using an adeno-associated virus (AAV) vector could provide significant APOE2 expression and decrease the levels of soluble and insoluble amyloid-β peptide and amy-loid burden. However, even with APOE2 supplementation, the presence of APOE4 still constitutes an increased risk as APOE2/4 heterozygotes have a 2.6-fold increased risk of developing AD. In one embodiment, an AAV-based gene therapy to introduce expression of the protective APOE2, a modified APOE2 or APOE3, while simultaneously decreas-ing the levels of deleterious endogenous APOE4 in APOE4 homozygotes is provided. In one embodiment, artificial microRNAs (miRNA) targeting the endogenous APOE4 are introduced into an AAV expression cassette along with the cDNA for the human APOE2 gene (hAPOE2-mirAPOE4). In one embodiment, the AAV9 serotype capsid is employed to package the expression cassette because it mediates efficient transduction of astrocytes, the main producers of APOE, as well as microglia and neurons. The established P301S/E4 AD mouse model that expresses mutant human tau and human APOE4 and has high phosphorylated tau burden, chronic inflammation, and extensive neurodegen-eration is used to assess therapy efficacy. To evaluate the strategy with AAV9-hAPOE2-mirAPOE4, an AAV con-struct is tested for silencing of endogenous APOE4 expres-sion and delivery of the APOE2 coding sequence in vitro. In addition, it is determined if augmentation of APOE2 with reduction of endogenous APOE4 protects against tau pathol-ogy, neurodegeneration, and neuroinflammation in vivo.

Adeno-associated virus (AAV) serotype rh.10 and sero-type 9 delivery of the human APOE2 coding sequence to the central nervous system (CNS) of two AD murine models by intrahippocampal or intrathalamic routes yielded significant levels of human APOE2 expression across the brain. Further, the amount of soluble and insoluble amyloid-β peptide and amyloid burden was reduced in portions of the brain. How-ever, genetically modifying the brain from APOE4/4 to APOE2/4 by only providing APOE2 does not completely mitigate the risk of the presence of APOE4. Decreasing expression of endogenous APOE4 along with delivering the protective APOE2 using AAV gene therapy can diminish the risk of APOE4 homozygotes than gene therapy with APOE2 alone.

The coding sequences for human APOE2 and APOE4 differ by two nucleotides. Artificial microRNA (miRNA) sequences were designed that target the endogenous APOE4 mRNA for suppression. Artificial miRNAs are screened in vitro for their ability to silence APOE expression in a human astroglioma cell line. Selected miRNAs are incorporated into the AAV expression cassette along with a modified human APOE2 cDNA that cannot be silenced by the miR-NAs. The selected AAV expression cassettes containing APOE2 and the artificial miRNAs targeting APOE4 are packaged into the AAV9 capsid in order to target expression to astrocytes, the main producers of APOE in the CNS.

P301S/E4 AD murine model mice express both human mutant tau and human APOE4 and develop high levels of phosphorylated tau, brain atrophy, and neuroinflammation from microglia activation. Because APOE in the CNS is expressed mainly from astrocytes. an AAV9 vector is used that efficiently transduces astrocytes as well as microglia and neurons in this study. AAV9-hAPOE2-mirAPOE4 and AAV9-hAPOE2 vectors are administered directly to the CNS of P301 S/E4 mice by the intracisternal route. Mice are evaluated for changes in behavior and cognitive function over time. After sacrifice, mice will be assessed for expression of vector-derived hAPOE2 and endogenous hAPOE4 in the brain as well as β-amyloid, total and phosphorylated tau levels and pathology, microglial activation, and brain atrophy.

Strategy. Alzheimer's symptoms include progressive decline of cognitive and functional abilities, including memory loss, confusion, personality and mood changes, and loss of ability to perform basic activities1. Brain pathology associated with AD includes the accumulation of extracellular beta-amyloid (Aβ) plaques and intracellular neurofibrillary tau tangles. Chronic neuroinflammation from glial activation and cell loss leading to brain atrophy are present in the advanced AD brain (Association As., 2019).

The strongest genetic risk factor for susceptibility to late-onset AD concerns polymorphisms in the apolipoprotein E (APOE) allele. APOE has three isoforms: APOE2, APOE3, and APOE4. APOE3 is the most common allele while the allelic frequency of APOE4 is approximately 15% and APOE2 8% (Farrer et al., 1997). However, the frequency of AD patients with APOE4 is 40-65% (Fairer et al., 1997; Corder et al., 1993; Ward et al., 2012). APOE4 is associated with accelerated rate and severity of cognitive decline and an earlier age of onset of AD. In contrast, APOE2 decreases the risk of AD development by 50% and delays onset by up to 10 years (Corder et al., 1993; Corder et al., 1997; Sando et al., 2008; Shinohara et al., 2016).

APOE is a secreted protein with a primary role in lipid transport in both the periphery and central nervous system (CNS). The APOE isoforms differ at only two amino acids positions 112 and 158 (APOE2: Cys/Cys, APOE3: Cys/Arg, APOE4: Arg/Arg). However, these differences profoundly affect the structure and function of APOE (Hatters & Peters-Libeu, 2006). Serum and brain concentration of APOE differ between isoforms (APOE2>APOE3>APOE4). There are differences in the lipidation status with APOE2 and APOE3 usually associating with high-density lipoproteins (HDL) and APOE4 with low- and very low-density lipoproteins (LDL, VLDL) (Hatters & Peters-Libeu, 2006; Dong et al., 1994). Additionally, APOE isoforms bind differentially to receptors including low-density lipoprotein receptor-related 1 (LRP1), heparan sulfate proteoglycans (HSPG), and LDL receptor (LDLR) with APOE2 having a lower affinity than APOE3 or APOE4 (Bu, 2009, Arboleda-Velasquez et al., 2019).

APOE plays numerous roles in the pathology and neurodegeneration found in AD. Extracellular Aβ plaques are a hallmark of AD pathology. Aβ deposition is more abundant in APOE4 carriers (Dorey et al., 2014). APOE4 enhances Aβ production, reduces Aβ clearance by impairing lysosomal degradation and transport across the blood brain barrier, and promotes Aβ aggregation and oligomer stabilization, representing a toxic gain-of-function (Jiang et al., 2008; Du et al., 2009; Nielsen et al., 2010; Rodriguez et al., 2014; Zekonyte et al., 2016; Lin et al., 2018; Wang et al., 2018). Hyperphosphorylated tau is the primary constituent of neurofibrillary tangles found in later stages of AD disease (Hampel et al., 2010). APOE4 expression exacerbates tau pathology (Shi et al., 2017). APOE4 shows weaker binding to tau than other isoforms (Strittmatter et al., 1994; Fleming et al., 1996), and expression of APOE4 in neurons can increase tau phosphorylation (Wang et al., 2018; Brecht et al., 2004; Harris et al., 2004). APOE also has immunomodulatory functions and greater immune response is associated with the APOE4 allele (Shi & Holtzman, 2018). Recent studies showed that innate immune activation in the CNS plays a key role in neuroinflammation and subsequent neuronal loss and brain atrophy in AD, and microglial activation is promoted by the presence of APOE4 (Rodriguez et al., 2014; Shi et al., 2017; Shi et al., 2019). APOE4 binds with higher affinity than APOE2 to receptors on neurons and stimulates enhanced activation of multiple signaling pathways including synapse formation and increased amyloid precursor protein (APP) transcription (Ohkubo et al., 2001; Huang et al., 2017; Huang et al., 2019), APOE4 binding to these receptors on damaged neurons also may act as an opsonin to promote neuronal phagocytosis by microglia via the interaction with the microglial expressed APOE binding partner 'triggering receptor expressed on myeloid cells-2' (TREM2) leading to enhanced neuronal loss and brain atrophy (Atagi et al., 2015; Bailey et al., 2015; Yeh et al., 2016; Jendresen et al., 2017). Further. APOE4 disrupts normal astrocyte and microglia homeostatic function (Fernandez et al., 2019). Clinically, APOE4 is associated with accelerated cognitive decline while APOE2 is protective (Shinohara et al., 2016; Helkala et al., 1996; Staehelin et al., 1999; Wilson et al., 2002). Thus, APOE4 plays a central role in multiple processes connected to AD development and is a prime target for intervention.

The human genetic data indicates that the APOE4 and APOE2 alleles have semi-dominant inheritance (Corder et al., 1994; Genin et al., 2011). While APOE4 homozygous individuals have a 14.5-fold increased risk of developing AD, APOE2/4 individuals have only a 2.6-fold increased risk, indicating that the presence of the protective APOE2 allele can partially mitigate the deleterious effects of the APOE4 allele. Although the risk of AD development is substantially reduced in APOE2/4 heterozygotes, it is still significantly higher than in individuals with APOE2/3 or APOE2/2 genotypes (1.8- and 7.7-fold decreased risk of AD development, respectively (Genin et al., 2011). This genetic data suggests that reduction in the level of APOE4 along with increasing APOE2 in the CNS would be beneficial for therapy for APOE4 carriers at high risk for AD development.

Human induced pluripotent stem cell derived neurons expressing APOE4 had increased Aβ production, higher levels of tau phosphorylation, and more degeneration that was corrected by converting APOE4 to APOE3 through gene editing (Lin et al., 2018; Wang et al., 2018). Previous studies from our group and others demonstrated that delivery of APOE2 to the CNS by viral vectors both increased the expression of APOE2 and decreased brain Aβ and amyloid burden in mouse models of AD41-43. The dose of APOE2 delivered and the amount of pre-existing Aβ1-42 deposition were important factors in determining the efficacy of the treatment (Zhao et al., 2016). However, in these previous studies, endogenous APOE4 was still present.

The disclosed therapies could be delivered to APOE4 homozygotes long before symptom onset to prevent or halt disease processes before they lead to AD.

Studies. Previous studies tested AAV serotype rh.10 and serotype 9 delivery of the human APOE2 coding sequence to the CNS of two AD murine models by intrahippocampal or intrathalmic routes. Human APOE2 was expressed to high levels across the brain using intrathalmic delivery of AAV9-APOE2 vector in the APP.PS1/TRE4 AD murine model of Aβ amyloidosis expressing human amyloid precursor protein (APP) and presenilin 1 (PS1) mutations and human APOE4 instead of murine APOE43 (FIG. 21A). Further, APOE2 augmentation reduced Aβ and amyloid loads in this AD mouse (Zhao et al., 2016) (FIG. 21B). One strategy is to encode artificial microRNAs (miRNA) targeting the endogenous APOE4 into the AAV expression cassette along with the cDNA for human APOE2 gene.

Target sequence selection. The APOE4 sequence was evaluated for the best targeting sequences for small interfering RNAs (siRNAs) using multiple algorithms and screened to minimize the potential for off-target interactions. Knockdown ability of the selected siRNAs was tested in vitro for endogenous APOE in the U87 human astroglioma cell line (FIG. 22). The siRNA sequences are not specific for APOE4 and will inhibit expression of all APOE isoforms. The best siRNA sequence was selected for incorporation into an artificial miRNA cassette for expression in the AAV vector.

The effect of the gene therapy focuses on tau pathology, neuroinflammation, and neurodegeneration. The AAV vector delivers persistent expression of human APOE2 along with artificial miRNAs targeting the endogenous APOE4 mRNA to downregulate expression (hAPOE2-mirAPOE4). AAV9 efficiently transduces astrocytes, which are the primary producers of APOE in the brain, as well as microglia and neurons and will be used for this study (Xu et al., 2006; Foust et al., 2009; Gray et al., 2011; Gong et al., 2015; Vagner et al., 2016; Zhang et al., 2014; Zhang et al., 2-2014). This AAV gene therapy provides enhanced APOE2 expression relative to APOE4 in APOE4 homozygotes, reduce neurofibrillary tau tangles, decrease microglial activation, reduce hippocampus and cortex pathology, and improve behavior.

AAV construct to silence endogenous APOE4 expression and deliver the APOE2 coding sequence in vitro. siRNA sequences were identified that effectively knockdown the expression of APOE in U87 human astroglioma cells. These sequences target segments of APOE that are common to all allele sequences. The most effective siRNA sequences are selected and incorporated into an enhanced mir155 artificial miRNA backbone to yield mirAPOE4 (Fowler et al., 2016) (FIG. 23A). As the placement of the mismatches in the hairpin stem and GC content can affect the processing of miRNAs in cells (Fowler et al., 2016; Fang & Bartel, 2015), several iterations of the mirAPOE4s are tested for ability to knockdown APOE in vitro to ensure the most effective design. Two to four tandem copies of the optimized mirAPOE4 are cloned into either the intron present in the AAV expression cassette promoter (hybrid CMV/Chicken β-actin; CAG) or into the intervening sequence between the transgene (mCherry or hAPOE2-HA) stop codon and the polyadenylation signal to determine the optimal number and positioning of mirAPOE4 in the expression cassette (Mueller et al., 2012) (FIG. 23B). The AAV mirAPOE4 expression cassette plasmids are tested in vitro for their ability to reduce expression of APOE by transfecting U87 cells for 72 hours before harvesting the culture media and cells. Expression of APOE mRNA is evaluated by RT-qPCR and secreted APOE protein by western blot and ELISA.

In parallel, silent mutations are made in the coding sequence of the human APOE2 cDNA at the recognition sites for the chosen mirAPOE4s to ensure that vector derived APOE2 expression cannot be silenced. Vector-derived human APOE2 has a C-terminal hemagglutinin (HA) tag to facilitate detection. Expression of vector-derived hAPOE2-HA in the presence of mirAPOE4 is confirmed by co-transfection and analysis of hAPOE2-HA expression by western blotting with an anti-HA antibody. The optimized hAPOE2-mirAPOE4 cassette is packaged into an AAV9 serotype capsid. AAV9 efficiently transduces astrocytes, which are the primary producers of APOE in the brain, as well as microglia and neurons. Functionality of the AAV9 vectors to express hAPOE2-HA and mirAPOE4 is confirmed in vitro before proceeding to in vivo experiments.

Figure 21:
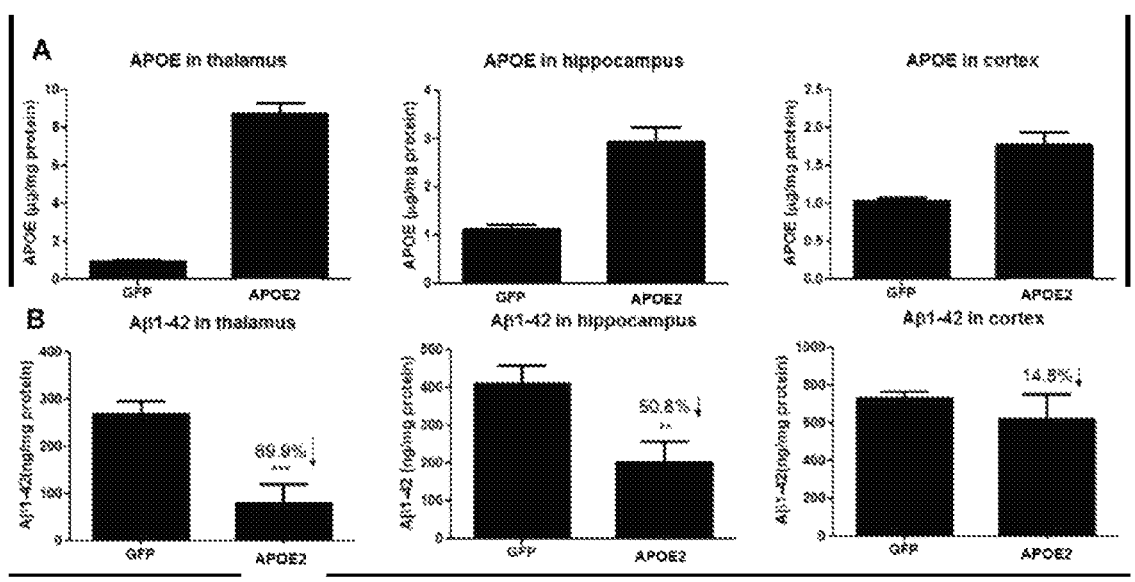

Augmentation of APOE2 may correlate with reduction of endogenous APOE4 protects against tau pathology, neurodegeneration. and neuroinflammation in vivo. Administration of AAV9-hAPOE2 to the CNS increased APOE levels across the brain and reduced Aβ1-42 levels in the APP.PS1/TRE4 AD mouse model of Aβ amyloidosis in the context of human APOE4 (Zhao et al., 2016; Kim et al, 2011) (FIG. 21). Because of the importance of neurofibrillary tau tangles and innate immune response in AD brain atrophy and cognitive dysfunction independent of Aβ load (Arboleda-Velasquez et al., 2019; Shi et al., 2017; Shi et al., 2019; Josephs et al., 2008; Mattsson et al., 2018), tau pathology, microglial activation, and neurodegeneration are determined. P301S/E4 mice overexpress 1N4R human tau containing the P301S mutation, linked to frontotemporal dementia, and human APOE4 replacing the mouse APOE (Shi et al., 2017; Yoshiyama et al., 2007). The P301S/E4 mice have higher brain phosphorylated tau burdens and more extensive neurodegeneration and neuroinflammation than mice expressing human APOE3 or APOE2 (Shi et al., 2017; Shi et al., 2019), but do not show amyloid plaque formation (Shi et al., 2017; Yoshiyama et al., 2007; Haurigot et al., 2013). P3015 1N4R tau B6/C3 mice (Jackson Laboratories 008169) and human APOE4 knockin mice (TRE4—Taconic 1549: B6.129P2-Apoetm3 (APOE*4)Mae N8) can recreate the published model by crossing the P3015 and TRE4 mice. C57B1/8 mice are used as wild-type controls.

The impact of vector-mediated delivery of AAV9-hAPOE2-mirAPOE4 expressing human APOE2 plus miRNA against endogenous APOE4 is assessed after administration by the intracisternal (IC) route in the P30151E4 mice. The IC route provides wide vector distribution throughout the brain with the least invasive administration (Haurigot et al., 2013; Hinderer et al., 2018; Rosenberg et al., 2018; Markmann et al., 2018). AAV9-hAPOE2, AAV9-mCherry-mirAPOE4, AAV9-null, and no therapy (PBS) are used as controls. Mice are evaluated for behavior and neurologic assessment monthly. After sacrifice, mice are evaluated for vector-derived hAPOE2 and endogenous APOE4 expression, Aβ peptide burden, total soluble and insoluble tau burden, hyperphosphorylated tau tangles, microglial activation, and brain neurodegeneration at 1 and 7 months post-administration (total age: 3 and 9 months, respectively) (Table 3).

TABLE 3

| Mouse Study | | | |
|---|---|---|---|
| Mouse model (genotype) | Vector | Administration dose and route | Parameters to be evaluated |
| P301S/E4 | AAV9-hAPOE2 AAV9-hAPOE2-mirAPOE4 AAV9-mCherry-mirAPOE4 $10^{11}$ gc, via intracisternal (IC) route | | Behavior and neurologic assessment (monthly) Brain expression of hAPOE4 and hAPOE2 Soluble and |
| | No therapy (PBS) | None (PBS, IC) | insoluble Aβ levels Assessment of |

TABLE 3-continued

| | | | Mouse Study |
|---|---|---|---|
| Mouse model (genotype) | Vector | Administration dose and route | Parameters to be evaluated |
| C57BI/6 (controls) | No therapy (PBS) | None (PBS, IC) | phosphorylated tau and total tau levels in brain homogenates CNS assessment of neurofibrillary tangles Microglial activation Pathology of hippocampus and cortex[13, 14] |
| 2 strains | 5 vectors | 1 route | Necropsy @ 3 and 9 months of age |

Eight wk old adult mice, n = 16 males and n = 16 females per treatment cohort (n = 192 total). All mice are randomly assigned to cohort groups, to avoid potential study bias, with staggered dosing of animals across all groups. Cages are numbered without treatment qualifiers to keep researchers blinded to treatment status.
Treatment cohorts involve double mutant mouse lines (P301S/E4) with human tau and APOE4 gene replacements. Wild-type controls with the same genetic background, C57Bl/6 strain, are used for 'No therapy' controls.
Vectors tested include: AAV9-hAPOE2, AAV9-hAPOE2-mirAPOE4, AAV9-mCherry-mirAPOE4, AAV9-null, or no therapy (PBS).
All vectors are administered at $10^{11}$ genome copies (gc) or PBS (10 μl) into the CSF via the IC route. This dose scales to a dose ($10^{14}$ gc) that is safe to deliver in humans (Sharma & McNeill, 2009).
Health checks are performed 3 times/weeks for the first two weeks, and then weekly afterwards on all surviving mice, with observation for any unusual or altered behavior. As part of the weekly health checks, the mice are weighed and recorded by personnel blinded to the treatment cohorts.
Mice are sacrificed at 2 time points (3 and 9 months of age, 1 and 7 months post-vector administration), half of each cohort is sacrificed (n = 8M/8F). During necropsy, the mouse CSF is sampled first from the cisterna magna, then the mice are perfused with cold PBS and the brain is collected and flash-frozen in liquid nitrogen and stored at −80° C. Half of the brain is used for vector DNA, mRNA, and protein assays. The remaining hemisphere is fixed and sectioned coronally at 50 μM slices for immunohistochemistry (IHC), immunofluorescence (IF), or pathology.
At monthly intervals, mice are subjected to a behavior and neurologic assessment. Mouse locomotor activity and ability to stand/rear are evaluated in the open field chamber equipped with infrared beam arrays to monitor and record mouse movements64. Second, the mice are tested for cognitive abilities by use of novel object recognition 24 hours after introduction of a new object. The test is performed inside of the open field chamber and the amount of time exploring the new object will be recorded (Webster et al., 2013). AD mice show decreased performance in this test with age. All testing is videotaped for examination of altered behavior by blinded personnel.

TABLE 3-continued

Mouse Study hAPOE2-HA and hAPOE4 protein are detected in brain tissue samples from multiple regions by western blotting/ELISA with antibodies specific for hAPOE4 and the hAPOE2 HA tag; mRNA are detected by RTqPCR using allele specific probes (Zhong et al., 2016). Microdissected sections of the hippocampus, thalmus, and cerebral cortex are homogenized and sequentially extracted with RIPA (soluble Aβ) and 5.5M guanidine (insoluble Aβ). Aβ1-42/1-40 levels are quantified by ELISA (Zhao et al., 2016).
Brain lysates are probed with antibodies against total tau (BT2) and phosphorylated-tau (CP13) by western blotting (Sacramento et al., 2020).
Brain slices are stained by anti-phospho-tau antibody AT8 for IHC/IF (Shi et al., 2017; Sacramento et al., 2020).
Microglia activation is assessed in brain sections by staining for CD68 positive cells by IHC (Shi et al., 2017).
Multiple brain slices, 300 μM apart, are stained with 0.1% Sudan black for brain volume analysis. The areas of interest, including hippocampus, posterior lateral ventricles, and piriform/entorhinal cortex, are traced and measured in the imaging software. Three sections are stained with cresyl violet for neuronal layer thickness measurements of the CA1 pyramidal cell layer and dentate gyrus granular cell layer for observational changes in the hippocampal region. Measurements are recorded using ImageJ software at all sites and averaged (Shi et al., 2017).
Neuronal toxicity of the AAV9 vector itself is evaluated in the cresyl violet stained brain sections by assessing the percentage of positively stained cells for each of the three sections.

Statistics. Studies are performed in triplicate for three independent experiments, and data will be presented as means±standard deviation (SD) unless otherwise stated. Differences between groups are analyzed using a one-way analysis of variance (ANOVA) for multiple comparisons. Aim 2 studies will be performed with n=8 mice per cohort (8M/8F). If the coefficient of variation is 35% for both groups, then the use of n=8 per group allows for a 2.8-fold difference between groups (p<0.05, power=0.95). Differences between groups for biochemical measurements are analyzed by ANOVA for multiple comparisons. Behavioral assessments are analyzed by two-way repeated measures ANOVA with multiple comparisons.

Exemplary Modified APOE2 sequences:

```
                                              (SEQ ID NO: 34)
ATGAAGGTTCTGTGGGCTGCGTTGCTGGTCACATTCCTGGCAGGATGCCAGGCCAAGGTGG

AGCAAGCGGTGGAGACAGAGCCGGAGCCCGAGCTGCGCCAGCAGACCGAGTGGCAGAGCGGCCA

GCGCTGGGAACTGGCACTGGGTCGCTTTTGGGATTACCTGCGCTGGGTGCAGACACTGTCTGAGCA

GGTGCAGGAGGAGCTGCTCAGCTCCCAGGTCACCCAGGAACTGAGGGCGCTGATGGACGAGACCA

TGAAAGAACTCAAAGCTTATAAGAGCGAGCTGGAGGAACAACTGACCCCGGTGGCGGAGGAGACG

CGGGCACGGCTGTCCAAGGAGCTGCAGGCGGCGCAGGCCCGGCTGGGCGCGGACATGGAGGACG

TGTGCGGCCGCCTGGTGCAGTACCGCGGCGAGGTGCAGGCCATGCTCGGCCAGAGCACCGAGGA

GCTGCGGGTGCGCCTCGCCTCCCACCTGCGCAAGCTGCGTAAGCGGCTCCTCCGCGATGCCGATG

ACCTGCAGAAGTGCCTGGCAGTGTACCAGGCCGGGGCCCGCGAGGGCGCCGAGCGCGGCCTCAG

CGCCATCCGCGAGCGCCTGGGGCCCCTGGTGGAACAGGGCCGCGTGCGGGCCGCCACTGTGGGC

TCCCTGGCCGGCCAGCCGCTACAGGAGCGGGCCCAGGCCTGGGGCGAGCGGCTGCGCGCGCGGA

TGGAGGAGATGGGCAGCCGGACCCGCGACCGCCTGGACGAGGTGAAGGAGCAGGTGGCGGAGGT

GCGCGCCAAGCTGGAGGAGCAGGCCCAGCAGATACGCCTGCAGGCCGAGGCCTTCCAGGCCCGC

CTCAAGAGCTGGTTCGAGCCCCTGGTGGAAGACATGCAGCGCCAGTGGGCCGGGCTGGTGGAGAA

GGTGCAGGCTGCCGTGGGCACCAGCGCCGCCCCTGTGCCCAGCGACAATCAC;

(SEQ ID NO: 27)
ATGAAGGTTCTGTGGGCTGCGTTGCTGGTCACATTCCTGGCAGGATGCCAGGCCAAGGTGG

AGCAAGCGGTGGAGACAGAGCCGGAGCCCGAGCTGCGCCAGCAGACCGAGTGGCAGAGCGGCCA
```

GCGCTGGGAACTGGCACTGGGTCGCTTTTGGGATTACCTGCGCTGGGTGCAGACACTGTCTGAGCA

GGTGCAGGAGGAGCTGCTCAGCTCCCAGGTCACCCAGGAACTGAGGGCGCTGATGGACGAGACCA

TGAAAGAACTTAAAGCATATAAGAGTGAGCTGGAGGAACAACTGACCCCGGTGGCGGAGGAGACGC

GGGCACGGCTGTCCAAGGAGCTGCAGGCGGCGCAGGCCCGGCTGGGCGCGGACATGGAGGACGT

GTGCGGCCGCCTGGTGCAGTACCGCGGCGAGGTGCAGGCCATGCTCGGCCAGAGCACCGAGGAG

CTGCGGGTGCGCCTCGCCTCCCACCTGCGCAAGCTGCGTAAGCGGCTCCTCCGCGATGCCGATGA

CCTGCAGAAGTGCCTGGCAGTGTACCAGGCCGGGGCCCGCGAGGGCGCCGAGCGCGGCCTCAGC

GCCATCCGCGAGCGCCTGGGGCCCCTGGTGGAACAGGGCCGCGTGCGGGCCGCCACTGTGGGCT

CCCTGGCCGGCCAGCCGCTACAGGAGCGGGCCCAGGCCTGGGGCGAGCGGCTGCGCGCGCGGAT

GGAGGAGATGGGCAGCCGGACCCGCGACCGCCTGGACGAGGTGAAGGAGCAGGTGGCGGAGGTG

CGCGCCAAGCTGGAGGAGCAGGCCCAGCAGATACGCCTGCAGGCCGAGGCCTTCCAGGCCCGCCT

CAAGAGCTGGTTCGAGCCCCTGGTGGAAGACATGCAGCGCCAGTGGGCCGGGCTGGTGGAGAAGG

TGCAGGCTGCCGTGGGCACCAGCGCCGCCCCTGTGCCCAGCGACAATCAC;

(SEQ ID NO: 28)
ATGAAGGTTCTGTGGGCTGCGTTGCTGGTCACATTCCTGGCAGGATGCCAGGCCAAGGTGGAGCAA

GCGGTGGAGACAGAGCCGGAGCCCGAGCTGCGCCAGCAGACCGAGTGGCAGAGCGGCCAGCGCT

GGGAACTGGCACTGGGTCGCTTTTGGGATTACCTGCGCTGGGTGCAGACACTGTCTGAGCAGGTGC

AGGAGGAGCTGCTCAGCTCCCAGGTCACCCAGGAACTGAGGGCGCTGATGGACGAGACCATGAAA

GAACTCAAAGCATATAAGAGTGAGCTGGAGGAACAACTGACCCCGGTGGCGGAGGAGACGCGGGC

ACGGCTGTCCAAGGAGCTGCAGGCGGCGCAGGCCCGGCTGGGCGCGGACATGGAGGACGTGTGC

GGCCGCCTGGTGCAGTACCGCGGCGAGGTGCAGGCCATGCTCGGCCAGAGCACCGAGGAGCTGC

GGGTGCGCCTCGCCTCCCACCTGCGCAAGCTGCGTAAGCGGCTCCTCCGCGATGCCGATGACCTG

CAGAAGTGCCTGGCAGTGTACCAGGCCGGGGCCCGCGAGGGCGCCGAGCGCGGCCTCAGCGCCA

TCCGCGAGCGCCTGGGGCCCCTGGTGGAACAGGGCCGCGTGCGGGCCGCCACTGTGGGCTCCCT

GGCCGGCCAGCCGCTACAGGAGCGGGCCCAGGCCTGGGGCGAGCGGCTGCGCGCGCGGATGGA

GGAGATGGGCAGCCGGACCCGCGACCGCCTGGACGAGGTGAAGGAGCAGGTGGCGGAGGTGCGC

GCCAAGCTGGAGGAGCAGGCCCAGCAGATACGCCTGCAGGCCGAGGCCTTCCAGGCCCGCCTCAA

GAGCTGGTTCGAGCCCCTGGTGGAAGACATGCAGCGCCAGTGGGCCGGGCTGGTGGAGAAGGTGC

AGGCTGCCGTGGGCACCAGCGCCGCCCCTGTGCCCAGCGACAATCAC;

(SEQ ID NO: 29)
ATGAAGGTTCTGTGGGCTGCGTTGCTGGTCACATTCCTGGCAGGATGCCAGGCCAAGGTGGAGCAA

GCGGTGGAGACAGAGCCGGAGCCCGAGCTGCGCCAGCAGACCGAGTGGCAGAGCGGCCAGCGCT

GGGAACTGGCACTGGGTCGCTTTTGGGATTACCTGCGCTGGGTGCAGACACTGTCTGAGCAGGTGC

AGGAGGAGCTGCTCAGCTCCCAGGTCACCCAGGAACTGAGGGCGCTGATGGACGAGACCATGAAA

GAACTTAAAGCTTAAAGAGTGAGCTGGAGGAACAACTGACCCCGGTGGCGGAGGAGACGCGGGC

ACGGCTGTCCAAGGAGCTGCAGGCGGCGCAGGCCCGGCTGGGCGCGGACATGGAGGACGTGTGC

GGCCGCCTGGTGCAGTACCGCGGCGAGGTGCAGGCCATGCTCGGCCAGAGCACCGAGGAGCTGC

GGGTGCGCCTCGCCTCCCACCTGCGCAAGCTGCGTAAGCGGCTCCTCCGCGATGCCGATGACCTG

CAGAAGTGCCTGGCAGTGTACCAGGCCGGGGCCCGCGAGGGCGCCGAGCGCGGCCTCAGCGCCA

TCCGCGAGCGCCTGGGGCCCCTGGTGGAACAGGGCCGCGTGCGGGCCGCCACTGTGGGCTCCCT

GGCCGGCCAGCCGCTACAGGAGCGGGCCCAGGCCTGGGGCGAGCGGCTGCGCGCGCGGATGGA

-continued

GGAGATGGGCAGCCGGACCCGCGACCGCCTGGACGAGGTGAAGGAGCAGGTGGCGGAGGTGCGC

GCCAAGCTGGAGGAGCAGGCCCAGCAGATACGCCTGCAGGCCGAGGCCTTCCAGGCCCGCCTCAA

GAGCTGGTTCGAGCCCCTGGTGGAAGACATGCAGCGCCAGTGGGCCGGGCTGGTGGAGAAGGTGC

AGGCTGCCGTGGGCACCAGCGCCGCCCCTGTGCCCAGCGACAATCAC;

(SEQ ID NO: 30)
ATGAAGGTTCTGTGGGCTGCGTTGCTGGTCACATTCCTGGCAGGATGCCAGGCCAAGGTGGAGCAA

GCGGTGGAGACAGAGCCGGAGCCCGAGCTGCGCCAGCAGACCGAGTGGCAGAGCGGCCAGCGCT

GGGAACTGGCACTGGGTCGCTTTTGGGATTACCTGCGCTGGGTGCAGACACTGTCTGAGCAGGTGC

AGGAGGAGCTGCTCAGCTCCCAGGTCACCCAGGAACTGAGGGCGCTGATGGACGAGACCATGAAA

GAACTTAAAGCATATAAGAGCGAGCTGGAGGAACAACTGACCCCGGTGGCGGAGGAGACGCGGGC

ACGGCTGTCCAAGGAGCTGCAGGCGGCGCAGGCCCGGCTGGGCGCGGACATGGAGGACGTGTGC

GGCCGCCTGGTGCAGTACCGCGGCGAGGTGCAGGCCATGCTCGGCCAGAGCACCGAGGAGCTGC

GGGTGCGCCTCGCCTCCCACCTGCGCAAGCTGCGTAAGCGGCTCCTCCGCGATGCCGATGACCTG

CAGAAGTGCCTGGCAGTGTACCAGGCCGGGGCCCGCGAGGGCGCCGAGCGCGGCCTCAGCGCCA

TCCGCGAGCGCCTGGGGCCCCTGGTGGAACAGGGCCGCGTGCGGGCCGCCACTGTGGGCTCCCT

GGCCGGCCAGCCGCTACAGGAGCGGGCCCAGGCCTGGGGCGAGCGGCTGCGCGCGCGGATGGA

GGAGATGGGCAGCCGGACCCGCGACCGCCTGGACGAGGTGAAGGAGCAGGTGGCGGAGGTGCGC

GCCAAGCTGGAGGAGCAGGCCCAGCAGATACGCCTGCAGGCCGAGGCCTTCCAGGCCCGCCTCAA

GAGCTGGTTCGAGCCCCTGGTGGAAGACATGCAGCGCCAGTGGGCCGGGCTGGTGGAGAAGGTGC

AGGCTGCCGTGGGCACCAGCGCCGCCCCTGTGCCCAGCGACAATCAC;

(SEQ ID NO: 31)
ATGAAGGTTCTGTGGGCTGCGTTGCTGGTCACATTCCTGGCAGGATGCCAGGCCAAGGTGGAGCAA

GCGGTGGAGACAGAGCCGGAGCCCGAGCTGCGCCAGCAGACCGAGTGGCAGAGCGGCCAGCGCT

GGGAACTGGCACTGGGTCGCTTTTGGGATTACCTGCGCTGGGTGCAGACACTGTCTGAGCAGGTGC

AGGAGGAGCTGCTCAGCTCCCAGGTCACCCAGGAACTGAGGGCGCTGATGGACGAGACCATGAAA

GAACTCAAAGCTTATAAGAGTGAGCTGGAGGAACAACTGACCCCGGTGGCGGAGGAGACGCGGGC

ACGGCTGTCCAAGGAGCTGCAGGCGGCGCAGGCCCGGCTGGGCGCGGACATGGAGGACGTGTGC

GGCCGCCTGGTGCAGTACCGCGGCGAGGTGCAGGCCATGCTCGGCCAGAGCACCGAGGAGCTGC

GGGTGCGCCTCGCCTCCCACCTGCGCAAGCTGCGTAAGCGGCTCCTCCGCGATGCCGATGACCTG

CAGAAGTGCCTGGCAGTGTACCAGGCCGGGGCCCGCGAGGGCGCCGAGCGCGGCCTCAGCGCCA

TCCGCGAGCGCCTGGGGCCCCTGGTGGAACAGGGCCGCGTGCGGGCCGCCACTGTGGGCTCCCT

GGCCGGCCAGCCGCTACAGGAGCGGGCCCAGGCCTGGGGCGAGCGGCTGCGCGCGCGGATGGA

GGAGATGGGCAGCCGGACCCGCGACCGCCTGGACGAGGTGAAGGAGCAGGTGGCGGAGGTGCGC

GCCAAGCTGGAGGAGCAGGCCCAGCAGATACGCCTGCAGGCCGAGGCCTTCCAGGCCCGCCTCAA

GAGCTGGTTCGAGCCCCTGGTGGAAGACATGCAGCGCCAGTGGGCCGGGCTGGTGGAGAAGGTGC

AGGCTGCCGTGGGCACCAGCGCCGCCCCTGTGCCCAGCGACAATCAC;

(SEQ ID NO: 32)
ATGAAGGTTCTGTGGGCTGCGTTGCTGGTCACATTCCTGGCAGGATGCCAGGCCAAGGTGGAGCAA

GCGGTGGAGACAGAGCCGGAGCCCGAGCTGCGCCAGCAGACCGAGTGGCAGAGCGGCCAGCGCT

GGGAACTGGCACTGGGTCGCTTTTGGGATTACCTGCGCTGGGTGCAGACACTGTCTGAGCAGGTGC

AGGAGGAGCTGCTCAGCTCCCAGGTCACCCAGGAACTGAGGGCGCTGATGGACGAGACCATGAAA

GAACTCAAAGCATATAAQAGCGAQCTGGAGGAACAACTGACCCCGGTGGCGGAGGAGACGCGGGC

-continued
```
ACGGCTGTCCAAGGAGCTGCAGGCGGCGCAGGCCCGGCTGGGCGCGGACATGGAGGACGTGTGC

GGCCGCCTGGTGCAGTACCGCGGCGAGGTGCAGGCCATGCTCGGCCAGAGCACCGAGGAGCTGC

GGGTGCGCCTCGCCTCCCACCTGCGCAAGCTGCGTAAGCGGCTCCTCCGCGATGCCGATGACCTG

CAGAAGTGCCTGGCAGTGTACCAGGCCGGGGCCCGCGAGGGCGCCGAGCGCGGCCTCAGCGCCA

TCCGCGAGCGCCTGGGGCCCCTGGTGGAACAGGGCCGCGTGCGGGCCGCCACTGTGGGCTCCCT

GGCCGGCCAGCCGCTACAGGAGCGGGCCCAGGCCTGGGGCGAGCGGCTGCGCGCGCGGATGGA

GGAGATGGGCAGCCGGACCCGCGACCGCCTGGACGAGGTGAAGGAGCAGGTGGCGGAGGTGCGC

GCCAAGCTGGAGGAGCAGGCCCAGCAGATACGCCTGCAGGCCGAGGCCTTCCAGGCCCGCCTCAA

GAGCTGGTTCGAGCCCCTGGTGGAAGACATGCAGCGCCAGTGGGCCGGGCTGGTGGAGAAGGTGC

AGGCTGCCGTGGGCACCAGCGCCGCCCCTGTGCCCAGCGACAATCAC;
or
```

```
                                                    (SEQ ID NO: 33)
ATGAAGGTTCTGTGGGCTGCGTTGCTGGTCACATTCCTGGCAGGATGCCAGGCCAAGGTGGAGCAA

GCGGTGGAGACAGAGCCGGAGCCCGAGCTGCGCCAGCAGACCGAGTGGCAGAGCGGCCAGCGCT

GGGAACTGGCACTGGGTCGCTTTTGGGATTACCTGCGCTGGGTGCAGACACTGTCTGAGCAGGTGC

AGGAGGAGCTGCTCAGCTCCCAGGTCACCCAGGAACTGAGGGCGCTGATGGACGAGACCATGAAA

GAACTTAAAGCTTATAAGAGCGAGCTGGAGGAACAACTGACCCCGGTGGCGGAGGAGACGCGGGC

ACGGCTGTCCAAGGAGCTGCAGGCGGCGCAGGCCCGGCTGGGCGCGGACATGGAGGACGTGTGC

GGCCGCCTGGTGCAGTACCGCGGCGAGGTGCAGGCCATGCTCGGCCAGAGCACCGAGGAGCTGC

GGGTGCGCCTCGCCTCCCACCTGCGCAAGCTGCGTAAGCGGCTCCTCCGCGATGCCGATGACCTG

CAGAAGTGCCTGGCAGTGTACCAGGCCGGGGCCCGCGAGGGCGCCGAGCGCGGCCTCAGCGCCA

TCCGCGAGCGCCTGGGGCCCCTGGTGGAACAGGGCCGCGTGCGGGCCGCCACTGTGGGCTCCCT

GGCCGGCCAGCCGCTACAGGAGCGGGCCCAGGCCTGGGGCGAGCGGCTGCGCGCGCGGATGGA

GGAGATGGGCAGCCGGACCCGCGACCGCCTGGACGAGGTGAAGGAGCAGGTGGCGGAGGTGCGC

GCCAAGCTGGAGGAGCAGGCCCAGCAGATACGCCTGCAGGCCGAGGCCTTCCAGGCCCGCCTCAA

GAGCTGGTTCGAGCCCCTGGTGGAAGACATGCAGCGCCAGTGGGCCGGGCTGGTGGAGAAGGTGC

AGGCTGCCGTGGGCACCAGCGCCGCCCCTGTGCCCAGCGACAATCAC.
```

REFERENCES

2020 Alzheimer's disease facts and figures. Alzheimers Dement. 2020.
Abner et al., *J. Alzheimers Dis.*, 64:1307 (2018).
Acosta-Baena et al., *Lancet. Neural.*, 10:213 (2011).
Allen et al., *J. Neurosci.*, 22:9340 (2002).
Arboleda-Velasquez et al., *Nat. Med.*, 25:1680 (2019).
Association As. 2019 Alzheimer's disease facts and figures. Alzheimer's & Dementia. 2019; 15:321-387.
Atagi et al., *J. Biol. Chem.*, 290:26043 (2015).
Bailey et al., *J. Biol. Chem.*, 290:26033 (2015).
Bales et al., *J. Neurosci.*, 29:6771 (2009).
Bales et al., *Nat. Genet.*, 17:263 (1997).
Benjamin et al., *Psychol. Aging*, 19:592 (2004).
Brecht et al., *J. Neurosci.*, 24:2527 (2004).
Bu, *Nat. Rev. Neurosci.*, 10:333 (2009).
Campion et al., *Am. J. Hum. Genet.*, 65:664 (1999).
Carmona et al., *Handb. Clin. Neural.*, 148:395 (2018).
Castellano et al., *Sci. Transl. Med.*, 3:89ra57 (2011).
Chaff et al., *J. Biol. Chem.*, 286:34457 (2011).
Chiang et al., *AJNR Am. J. Neuroradiol.*, 33:1392 (2012).
Chiang et al., *Neurology.* 75:1976 (2010).
Collaborators GBDD, *Lancet Neural.*, 18:88 (2019).
Conejero-Goldberg et al., *Mol. Psychiatry.*, 19:1243 (2014).
Conrado et al., *Clin. Pharmacol. Ther.*, 107:796 (2020).
Coon et al., *J. Clin. Psychiatry*, 68:613 (2007).
Corder et al., *Nat. Genet.*, 7:180 (1994).
Corder et al., *Science*, 261:921 (1993).
Dai et al., *Oncotarget.*, 9:15132 (2018).
Deane et al., *J. Clin. Invest.*, 118:4002 (2008).
DeTure & Dickson, *Mol. Neurodegener.*, 14:32 (2019).
Dodart et al., *Proc. Natl. Acad. Sci. U.S.A.*, 102:1211 (2005).
Dong et al., *J. Biol. Chem.*, 269:22358 (1994).
Dorey et al., *Neurosci. Bull.*, 30:317 (2014).
Du et al., *Neurosci. Lett.*, 464:140 (2009).
Exceptionally low likelihood of alzheimer's dementia in APOE2 homozygotes [Internet]. 2019.
Fagan et al., *Neurobiol. Dis.*, 9:305 (2002).
Fang and Bartel, *Mol. Cell.*, 60:131 (2015).
Fann et al., *Lancet. Psychiatry.*, 5:424 (2018).
Farrer et al., *JAMA*, 278:1349 (1997).
Fernandez et al., *Front Aging Neurosci.*, 11:14 (2019).
Fernandez et al., *Neurosci.*, 11:14 (2019).
Fleming et al., *Exp. Neural.*, 138:252 (1996).
Flowers & Rebeck, *Neurobiol. Dis.*, 136:104724 (2020).

Foust et al., *Nat. Biotechnol.*, 27:59 (2009).

Fowler et al., *Nucleic Acids Res.*, 44:e48 (2016).

Franklin K, Paxinos G. Paxinos and Franklin's the Mouse Brain in Stereotaxic Coordinates, Compact Academic Press; 2019.

Gale et al., *J. Allergy Clin. Immunol.*, 134:127 (2014).

Games et al., *Nature*, 373:523 (1995).

Gatz et al., *Nat. Rev. Neurosci.*, 19:583 (2018).

Genin et al., *Mol. Psychiatry.*, 16:903 (2011).

Gong et al., *Mol. Ther.*, 23:824 (2015).

Gray et al., *Mol. Ther.*, 19:1058 (2011).

Hampel et al., *Exp. Gerontol.*, 45:30 (2010).

Harris et al., *J. Biol. Chem.*, 279:44795 (2004).

Hashimoto et al., *J. Neurosci.*, 32:15181 (2012).

Hatters et al., *J. Mol. Biol.*, 361:932 (2006b).

Hatters et al., *Trends Biochem. Sci.*, 31:445 (2006a).

Haurigot et al., *J. Clin. Invest.*, 123:3254 (2013).

Hebert et al., *Neurology*, 80:1778 (2013).

Heffernan et al., *J. Mol. Neurosci.*, 60:316 (2016).

Helkala et al., *Neurosci. Lett.*, 204:177 (1996).

Hinderer et al., *Hum. Gene. Ther.*, 29:15 (2018).

Holtzman et al., *Cold Spring Harb. Perspect Med.*, 2:a006312 (2012).

Holtzman et al., *Proc. Natl. Acad. Sci. U.S.A.*, 97:2892 (2000).

Hu et al., *Mol. Neurodegener.*, 10:6 (2015).

Huang et al., *Cell.* 168:427 (2017).

Huang et al., *J. Neurosci.*, 39:7408 (2019).

Hudry et al., *Sci. Transl. Med.*, 5:212ra161 (2013).

Jankowsky et al., *Biomol. Eng.*, 17:157 (2001).

Jendresen et al., *J. Neuroinflammation*, 14:59 (2017).

Jiang et al., *Neuron.*, 58:681 (2008).

Josephs et al., *Ann. Neurol.*, 63:204 (2008).

Kim et al., *J. Neurosci.*, 31:18007 (2011).

Li et al., *J. Biol. Chem.*, 287:44593 (2012).

Liao et al., *Curr. Opin. Lipidol.*, 28:60 (2017).

Lin et al., *Neuron.*, 98:1141 (2018).

Liu et al., *J. Neurosci.*, 36:12425 (2016).

Liu et al., *Nat. Rev. Neural.*, 9:106 (2013).

Liu et al., *Sci. Transl. Med.*, 8:332ra344 (2016).

Lopera et al., *JAMA*, 277:793 (1997).

Mahley et al., *Ann. NY Acad. Sci.*, 777:139 (1996).

Mahley et al., *J. Lipid, Res.*, 40:1933 (1999).

Mahley, *Arterioscler. Thromb. Vase. Biol.*, 36:1305 (2016).

Manelli et al., *J. Mol. Neurosci.*, 23:235 (2004).

Markmann et al. *Exp. Neurol.*, 306:22 (2018).

Mattsson et al., *Alzheimers Res. Ther.*, 10:77 (2018).

Mondadori et al., *Cereb. Cortex.*, 17:1934 (2007).

Mueller et al., *Mol. Ther.*, 20:590 (2012).

Nagy et al., *Neuroscience*, 69:757 (1995).

Naj et al., *Nat. Genet.*, 43:436 (2011).

Nielsen et al., *Gila.*, 58:1235 (2010).

O'Callaghan et al., *J. Histochem. Cytochem.*, 66:305 (2018).

Ohkubo et al., *J. Biol. Chem.*, 276:3046 (2001).

Phillips, *IUBMB Life*, 66:616 (2014).

Pitas et al., *Biochim. Biophys. Acta.*, 917:148 (1987).

Prince et al., *Alzheimers Dement.*, 9:63 (2013).

Puglielli et al., *Nat. Neurosci.*, 6:345 (2003).

Raber et al., *Neurobiol. Aging*, 25:641 (2004).

Raman et al., *BMC Genomics*, 10:493 (2009).

Rauch et al., *Sci. Rep.*, 8:6382 (2018).

Rebeck et al., *J. Alzheimers Dis.*, 4:145 (2002).

Reiman et al., *Nat. Commun.*, 11:667 (2020).

Reiman et al., *Proc. Natl. Acad. Sci, U.S.A.*, 106:6820 (2009).

Rodriguez et al. *J. Neuroinflammation.*, 11:111 (2014).

Rosenberg et al., *Hum. Gene Ther. Clin. Dev.*, 25:164 (2014).

Rosenberg et al., *Hum. Gene. Ther. Clin. Dev.*, 29:24 (2018).

Ryan et al., *PLoS One*, 9:e88051 (2014).

Sacramento et al., *Hum. Gene. Ther.*, 31:57 (2020).

Safieh et al., *BMC Med.*, 17:64 (2019).

Sando et al., *BMC Neurol.*, 8:9 (2008).

Schenk et al., *Nature*, 400:173 (1999).

Schmechel et al., *Proc. Natl. Acad. Sol. U.S.A.*, 90:9649 (1993).

Sharma & McNeill, *Br. J. Pharmacol.*, 157:907 (2009).

Shi & Holtzman, *Nat. Rev. Immunol.*, 18:759 (2018).

Shi et al., *J. Exp. Med.*, 216:2546 (2019).

Shi et al., *Nature*, 549:523 (2017).

Shinohara et al., *Ann. Neurol.*, 79:758 (2016).

Snow et al., *Am. J. Pathol.*, 133:456 (1988).

Sondhi et al., *Hum. Gene Ther. Methods*, 23:324 (2012).

Sondhi et al., *Mol. Ther.*, 15:481 (2007).

Staehelin et al., *Acta. Neurol. Scand.*, 100:53 (1999).

Strittmatter et al., *Proc. Natl. Acad. Sci, U.S.A.*, 91:11183 (1994).

Sullivan et al., *J. Stroke Cerebrovasc. Dis.*, 17:303 (2008).

Tardieu et al., *Hum. Gene Ther.*, 25:506 (2014).

Tatem et al., *J. Visualized Exp., JoVE.*: 51785 (2014).

Tumor Analysis Best Practices Working G. Expression profiling—best practices for data generation and interpretation in clinical trials, *Nat, Rev. Genet.*, 5:229 (2004).

Tzioras et al., *Neuropathol. Appl. Neurobiol.*, 45:327 (2019).

Vagner et al., *Mol. Cell. Neurosci.*, 77:76 (2016).

Vitek et al., *Neurobiol. Aging*, 30:1350 (2009).

Walker et al., *Acta. Neuropathol.*, 100:36 (2000).

Wang et al., *Nat. Med.*, 24:647 (2018).

Ward et al., *Neuroepidemiology*, 38:1 (2012).

Webster et al., *Alzheimer's research & therapy*, 5:28 (2013).

Wildsmith et al., Anal. Biochem., 395:116 (2009).

Williams et al., *Mol. Neurodegener.*, 15:8 (2020).

Wilson et al., *J. Neurol. Neurosurg. Psychiatry.*, 73:672 (2002).

Wolters et al., *PLoS One.*, 14:e0219668 (2019).

World Health Organization. The Epidemiology and impact of dementia current state and future trends. 2015 https://www.who.int/mental_health/neurology/dementia/dementia_thematicbrief_epidemiology.pdf [last accessed Jun. 3, 2020]

Xu et al., *J. Neurosci.*, 26:4985 (2006).

Yeh et al., i Neuron., 91:328 (2016).

Yoshiyama et al., *Neuron.*, 53:337 (2007).

Yu et al., *Annu. Rev. Neurosci.*, 37:79 (2014).

Zannis & Breslow, *Biochemistry*, 20:1033 (1981).

Zekonyte et al., *Biochim. Biophys. Acta.*, 1862:1047 (2016).

Zerah et al., *Hum. Gene Ther. Clin. Dev.*, 26:113 (2015).

Zhang et al., *Genet. Test Mol, Biomarkers.*, 17:47 (2013).

Zhang et al., *J. Neurosci.*, 34:11929 (2014).

Zhang et al., *Neuron.*, 89:37 (2016).

Zhao et al., *Angew. Chem. Int. Ed. Engl.*, (2019).

Zhao et al., *J. Neurosci.*, 29:3603 (2009).

Zhao et al., *Neurobiol. Aging*, 44:159 (2016).

Zhong et al., *Mol. Neurodegener.*, 11:2 (2016).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An adeno-associated virus (AAV) vector comprising in the 5' to 3' direction:
   - a first AAV2 ITR sequence;
   - a CMV enhancer sequence;
   - a chicken beta-actin promoter sequence;
   - a nucleic acid sequence encoding an apolipoprotein 2 (APOE2) polypeptide comprising a Christchurch mutation, wherein the Christchurch mutation is R136S of APOE2;
   - a polyA sequence; and
   - a second AAV2 ITR sequence.

2. The AAV vector of claim 1 wherein the APOE2 polypeptide is a human APOE2 polypeptide.

3. The AAV vector of claim 1 wherein the APOE2 polypeptide comprises substitutions R136S and R158C in the mature form of the amino acid sequence set forth in SEQ ID NO: 1.

4. The AAV vector of claim 1 wherein the AAV vector is packaged as an AAV viral vector comprising an AAV capsid protein.

5. The AAV vector of claim 4 wherein the AAV capsid protein is an AAV1 capsid protein, an AAV2 capsid protein, an AAV4 capsid protein, an AAV5 capsid protein, an AAV7 capsid protein, an AAV8 capsid protein, an AAV9 capsid protein, or an AAVrh10 capsid protein.

6. The AAV vector of claim 4, wherein the capsid protein is an AAVrh10 capsid protein.

* * * * *